US012279768B2

(12) United States Patent
Witte

(10) Patent No.: US 12,279,768 B2
(45) Date of Patent: *Apr. 22, 2025

(54) SURGICAL INSTRUMENTS WITH DOUBLE SPHERICAL ARTICULATION JOINTS WITH PIVOTABLE LINKS

(71) Applicant: Cilag GmbH International, Zug (CH)

(72) Inventor: Spencer J. Witte, Los Altos, CA (US)

(73) Assignee: Cilag GmbH International, Zug (CH)

( * ) Notice: Subject to any disclaimer, the term of this patent is extended or adjusted under 35 U.S.C. 154(b) by 0 days.

This patent is subject to a terminal disclaimer.

(21) Appl. No.: 18/346,427

(22) Filed: Jul. 3, 2023

(65) Prior Publication Data

US 2023/0338020 A1 Oct. 26, 2023

Related U.S. Application Data

(63) Continuation of application No. 17/360,176, filed on Jun. 28, 2021, now Pat. No. 11,737,748.

(Continued)

(51) Int. Cl.
*A61B 17/072* (2006.01)
*A61B 17/00* (2006.01)
(Continued)

(52) U.S. Cl.
CPC .... *A61B 17/0686* (2013.01); *A61B 17/00234* (2013.01); *A61B 17/068* (2013.01);
(Continued)

(58) Field of Classification Search
CPC .......... A61B 17/0686; A61B 17/00234; A61B 17/068; A61B 17/072; A61B 17/07207;
(Continued)

(56) References Cited

U.S. PATENT DOCUMENTS 2,425,809 A * 8/1947 Johnson .................... F16D 3/16
464/157
5,007,300 A * 4/1991 Siva ................... G05G 9/04737
74/471 XY (Continued)

FOREIGN PATENT DOCUMENTS

EP 2036505 A1 * 3/2009 ....... A61B 17/00234
EP 3241506 A1 * 11/2017 ....... A61B 17/07207
(Continued)

OTHER PUBLICATIONS

Extended European Search Report dated Mar. 6, 2023, for Application No. 22213205.2, 7 pages.
(Continued)

*Primary Examiner* — Robert F Long
(74) *Attorney, Agent, or Firm* — Frost Brown Todd LLP

(57) ABSTRACT

Surgical instruments with articulation joints that include an articulation linkage assembly comprising a plurality of links configured to operably interface with a proximal joint member for movable travel relative thereto in a first proximal travel path and a second proximal travel path that are transverse to each other. The plurality of links are further configured to operably interface with a distal joint member for movable travel relative thereto in a first distal travel path and a second distal travel path that are transverse each other.

20 Claims, 63 Drawing Sheets

Related U.S. Application Data

(60) Provisional application No. 63/057,430, filed on Jul. 28, 2020, provisional application No. 63/057,432, filed on Jul. 28, 2020.

(51) Int. Cl.
*A61B 17/068* (2006.01)
*A61B 17/29* (2006.01)
*A61B 17/32* (2006.01)
*A61B 34/30* (2016.01)

(52) U.S. Cl.
CPC ...... *A61B 17/072* (2013.01); *A61B 17/07207* (2013.01); *A61B 17/29* (2013.01); *A61B 17/320092* (2013.01); *A61B 34/30* (2016.02); *A61B 2017/00314* (2013.01); *A61B 2017/00323* (2013.01); *A61B 2017/00336* (2013.01); *A61B 2017/00367* (2013.01); *A61B 2017/00389* (2013.01); *A61B 2017/00398* (2013.01); *A61B 2017/00477* (2013.01); *A61B 2017/07214* (2013.01); *A61B 2017/07257* (2013.01); *A61B 2017/07271* (2013.01); *A61B 2017/07278* (2013.01); *A61B 2017/07285* (2013.01); *A61B 2017/2927* (2013.01); *A61B 2017/320071* (2017.08); *A61B 2017/320093* (2017.08); *A61B 2017/320094* (2017.08); *A61B 2017/320095* (2017.08); *A61B 2017/320097* (2017.08); *A61B 2034/301* (2016.02)

(58) Field of Classification Search
CPC . A61B 17/29; A61B 17/320092; A61B 34/30; A61B 2017/00314; A61B 2017/00323; A61B 2017/00336; A61B 2017/00367; A61B 2017/00389; A61B 2017/00398; A61B 2017/00477; A61B 2017/07214; A61B 2017/07257; A61B 2017/07271; A61B 2017/07278; A61B 2017/07285; A61B 2017/2927; A61B 2017/320071; A61B 2017/320093; A61B 2017/320094; A61B 2017/320095; A61B 2017/320097; A61B 2034/301; A61B 34/71; A61B 2017/00327; A61B 2017/0069; A61B 2017/00845; A61B 2017/2903; A61B 2034/302
USPC ......... 227/175.1–182.1, 8, 19; 606/139, 142, 606/143, 205–208
See application file for complete search history.

(56) References Cited

U.S. PATENT DOCUMENTS

| | | | |
|---|---|---|---|
| 5,142,931 A * | 9/1992 | Menahem | G05G 9/047 244/236 |
| 5,316,435 A * | 5/1994 | Mozingo | G05G 9/047 74/529 |
| 5,403,312 A | 4/1995 | Yates et al. | |
| 5,455,997 A * | 10/1995 | Nasiell | B25B 13/481 29/888.011 |
| 5,607,449 A * | 3/1997 | Tontarra | A61B 17/29 606/208 |
| 5,632,432 A * | 5/1997 | Schulze | A61B 17/07207 227/176.1 |
| 5,704,534 A * | 1/1998 | Huitema | A61B 17/07207 227/176.1 |
| 5,851,208 A * | 12/1998 | Trott | A61B 17/32002 606/80 |
| 6,582,451 B1 * | 6/2003 | Marucci | A61B 17/29 606/207 |
| 6,985,133 B1 * | 1/2006 | Rodomista | G06F 3/016 345/161 |
| 7,000,818 B2 | 2/2006 | Shelton, IV et al. | |
| 7,273,488 B2 | 9/2007 | Nakamura et al. | |
| 7,422,139 B2 | 9/2008 | Shelton, IV et al. | |
| 7,464,849 B2 | 12/2008 | Shelton, IV et al. | |
| 7,561,141 B2 * | 7/2009 | Shahoian | G06F 3/0338 345/184 |
| 7,670,334 B2 | 3/2010 | Hueil et al. | |
| 7,753,245 B2 | 7/2010 | Boudreaux et al. | |
| 7,780,577 B2 * | 8/2010 | Arnold | A63B 22/001 482/52 |
| 7,845,537 B2 | 12/2010 | Shelton, IV et al. | |
| 7,980,443 B2 | 7/2011 | Scheib et al. | |
| 8,210,411 B2 | 7/2012 | Yates et al. | |
| 8,220,688 B2 | 7/2012 | Laurent et al. | |
| 8,308,040 B2 | 11/2012 | Huang et al. | |
| 8,393,514 B2 | 3/2013 | Shelton, IV et al. | |
| 8,495,934 B2 * | 7/2013 | Schneider | B25B 23/0021 81/177.75 |
| 8,561,870 B2 | 10/2013 | Baxter, III et al. | |
| 8,608,045 B2 | 12/2013 | Smith et al. | |
| 8,733,613 B2 | 5/2014 | Huitema et al. | |
| 9,050,083 B2 | 6/2015 | Yates et al. | |
| 9,072,535 B2 | 7/2015 | Shelton, IV et al. | |
| 9,101,358 B2 | 8/2015 | Kerr et al. | |
| 9,161,807 B2 * | 10/2015 | Garrison | A61B 18/1447 |
| 9,345,481 B2 | 5/2016 | Hall et al. | |
| 9,572,628 B2 * | 2/2017 | Zubiate | A61B 34/30 |
| 9,777,459 B2 * | 10/2017 | Zuritis | E02F 3/3414 |
| 10,292,701 B2 * | 5/2019 | Scheib | A61B 17/07292 |
| 11,331,106 B2 * | 5/2022 | Fenn | A61B 17/1757 |
| 11,399,836 B2 * | 8/2022 | Cabrera | A61B 17/1155 |
| 11,607,219 B2 * | 3/2023 | Shelton, IV | A61B 17/07207 |
| 11,638,582 B2 | 5/2023 | Bakos et al. | |
| 11,660,090 B2 | 5/2023 | Bakos et al. | |
| 12,000,280 B2 * | 6/2024 | King | E21B 7/026 |
| 2002/0193809 A1 * | 12/2002 | Meade | A61B 17/0469 606/222 |
| 2006/0074407 A1 * | 4/2006 | Padget | A61B 17/3201 606/1 |
| 2007/0152014 A1 * | 7/2007 | Gillum | A61B 17/07207 227/175.1 |
| 2007/0175955 A1 | 8/2007 | Shelton et al. | |
| 2008/0035701 A1 * | 2/2008 | Racenet | A61B 17/07207 227/176.1 |
| 2008/0064572 A1 * | 3/2008 | Nardone | A63B 22/0064 482/52 |
| 2008/0093517 A1 * | 4/2008 | Chen | A63B 22/0605 482/57 |
| 2008/0161174 A1 * | 7/2008 | Lo | A63B 21/00178 482/142 |
| 2008/0177283 A1 * | 7/2008 | Lee | A61B 34/77 606/130 |
| 2008/0280736 A1 * | 11/2008 | D'Eredita | A63B 69/06 482/72 |
| 2008/0305934 A1 * | 12/2008 | Medina | A63B 22/0076 482/72 |
| 2008/0308607 A1 * | 12/2008 | Timm | A61B 17/07207 227/176.1 |
| 2009/0181832 A1 * | 7/2009 | Bell | A63B 21/154 482/72 |
| 2010/0009818 A1 * | 1/2010 | Simonson | A63B 23/03541 482/97 |
| 2010/0030018 A1 * | 2/2010 | Fortier | A61B 18/1445 600/104 |
| 2010/0076461 A1 * | 3/2010 | Viola | A61B 17/0469 606/144 |
| 2010/0294089 A1 * | 11/2010 | Lai | B25G 1/043 81/177.85 |
| 2011/0172648 A1 * | 7/2011 | Jeong | A61B 34/71 606/1 |
| 2011/0197719 A1 * | 8/2011 | Neitzell | B25F 5/001 81/177.75 |
| 2011/0276057 A1 * | 11/2011 | Conlon | A61B 17/3421 606/130 |

(56) References Cited

U.S. PATENT DOCUMENTS

| | | | |
|---|---|---|---|
| 2012/0010616 A1* | 1/2012 | Huang | A61B 18/1445 606/52 |
| 2012/0083770 A1* | 4/2012 | Paik | A61B 17/29 606/1 |
| 2012/0197239 A1 | 8/2012 | Smith et al. | |
| 2012/0277762 A1* | 11/2012 | Lathrop | A61B 34/70 606/130 |
| 2012/0310220 A1* | 12/2012 | Malkowski | A61B 17/29 606/1 |
| 2014/0005681 A1* | 1/2014 | Gee | A61B 17/320092 606/130 |
| 2014/0025046 A1* | 1/2014 | Williams | A61B 17/07207 606/1 |
| 2014/0166718 A1* | 6/2014 | Swayze | A61B 17/1155 227/175.1 |
| 2014/0263552 A1 | 9/2014 | Hall et al. | |
| 2015/0014392 A1* | 1/2015 | Williams | A61B 17/072 227/180.1 |
| 2015/0150574 A1* | 6/2015 | Richard | A61B 17/068 606/205 |
| 2015/0173755 A1* | 6/2015 | Baxter, III | A61B 17/07207 227/180.1 |
| 2015/0289873 A1* | 10/2015 | Shelton, IV | A61B 17/0682 227/176.1 |
| 2017/0021507 A1* | 1/2017 | Jackson | F16H 19/001 |
| 2017/0095922 A1* | 4/2017 | Licht | A61B 34/71 |
| 2017/0105746 A1* | 4/2017 | O'Keefe | A61B 17/00234 |
| 2017/0135695 A1* | 5/2017 | Shelton, IV | A61B 34/30 |
| 2017/0202545 A1* | 7/2017 | Nicholas | A61B 17/00 |
| 2017/0224334 A1* | 8/2017 | Worthington | A61B 17/32 |
| 2017/0224342 A1* | 8/2017 | Worthington | A61B 17/105 |
| 2017/0311944 A1* | 11/2017 | Morgan | A61B 34/73 |
| 2018/0168649 A1* | 6/2018 | Shelton, IV | A61B 17/07207 |
| 2018/0310935 A1* | 11/2018 | Wixey | F16D 3/32 |
| 2018/0353178 A1* | 12/2018 | Shelton, IV | A61B 17/068 |
| 2019/0125358 A1* | 5/2019 | Shelton, IV | A61B 17/2909 |
| 2019/0247048 A1* | 8/2019 | Gasparovich | A61B 34/71 |
| 2020/0330126 A1* | 10/2020 | Sgroi, Jr. | A61B 17/3468 |
| 2021/0052332 A1* | 2/2021 | Saulenas | A61B 34/71 |
| 2021/0052333 A1* | 2/2021 | Johnson | A61B 34/37 |
| 2021/0186506 A1* | 6/2021 | Shelton, IV | A61B 17/07207 |
| 2021/0196356 A1* | 7/2021 | Shelton, IV | A61B 17/320092 |
| 2022/0031315 A1 | 2/2022 | Bakos et al. | |
| 2022/0031319 A1 | 2/2022 | Witte et al. | |
| 2022/0031320 A1 | 2/2022 | Hall et al. | |
| 2022/0031322 A1 | 2/2022 | Parks | |
| 2022/0031323 A1 | 2/2022 | Witte | |
| 2022/0031324 A1 | 2/2022 | Hall et al. | |
| 2022/0031345 A1 | 2/2022 | Witte | |
| 2022/0031346 A1 | 2/2022 | Parks | |
| 2022/0031350 A1 | 2/2022 | Witte | |
| 2022/0031351 A1 | 2/2022 | Moubarak et al. | |
| 2022/0167958 A1* | 6/2022 | Au | A61B 34/71 |
| 2022/0304683 A1* | 9/2022 | Shelton, IV | A61B 17/0686 |

FOREIGN PATENT DOCUMENTS

| | | |
|---|---|---|
| JP | 2018-531694 A | 11/2018 |
| JP | 6502115 B2 | 4/2019 |
| WO | WO 2006/073581 A2 | 7/2006 |

OTHER PUBLICATIONS

International Search Report and Written Opinion dated Nov. 2, 2021, for International Application No. PCT/IB2021/056761, 11 pages.

U.S. Appl. No. 12/031,573, entitled "Surgical Cutting and Fastening Instrument Having RF Electrodes," filed Feb. 14, 2008.

* cited by examiner

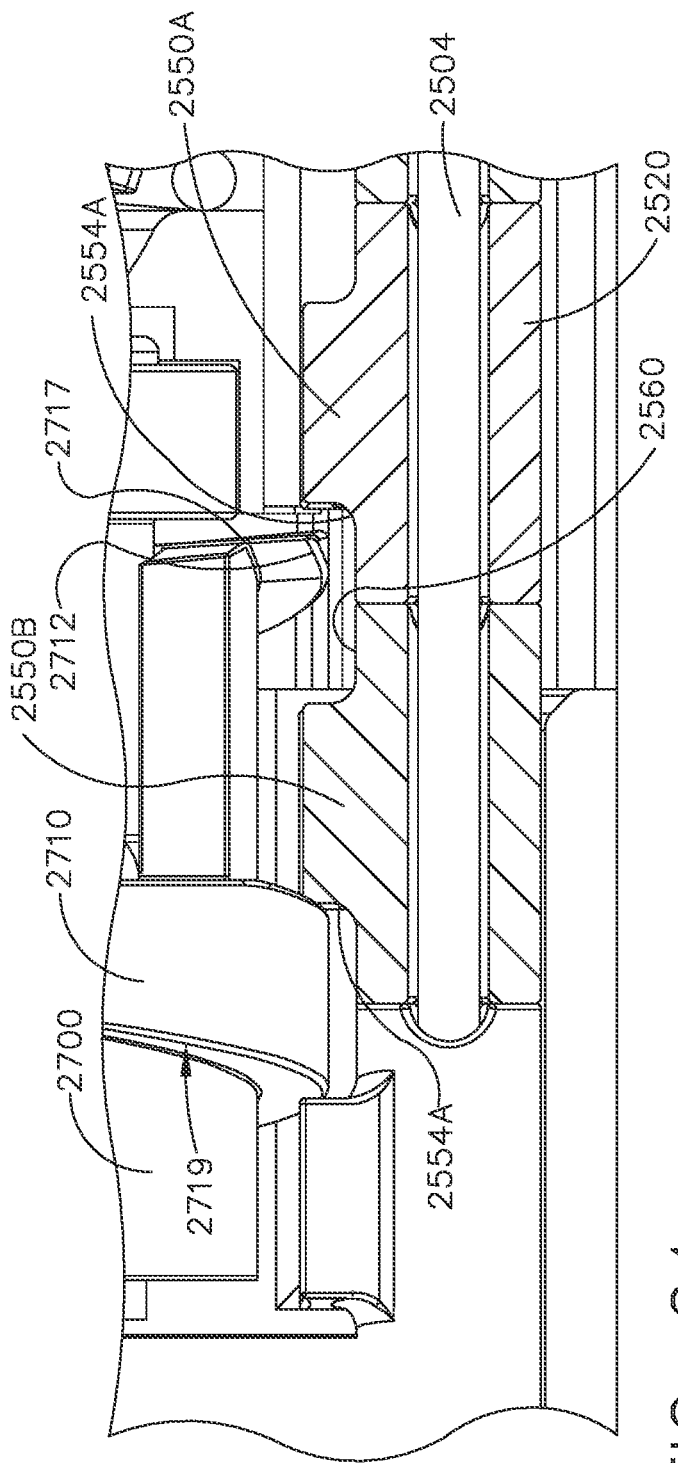
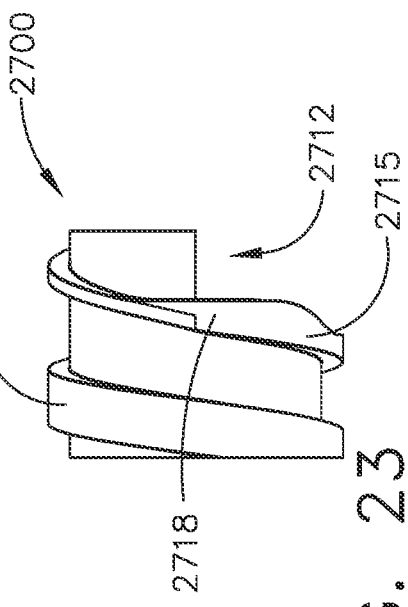
FIG. 24
FIG. 23

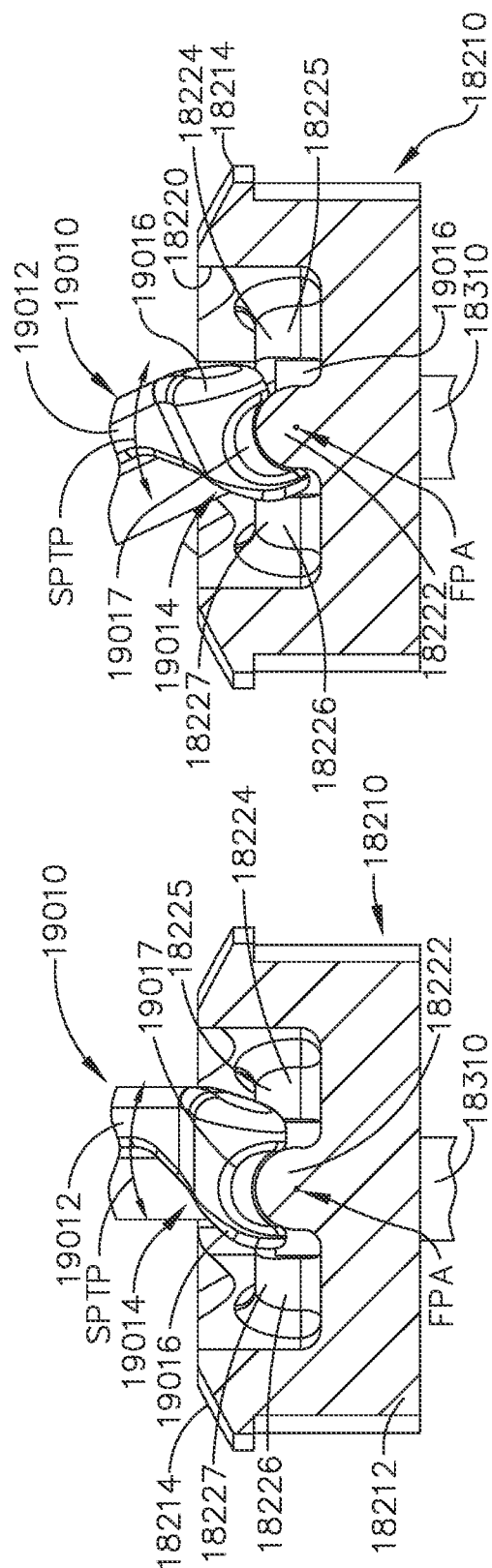

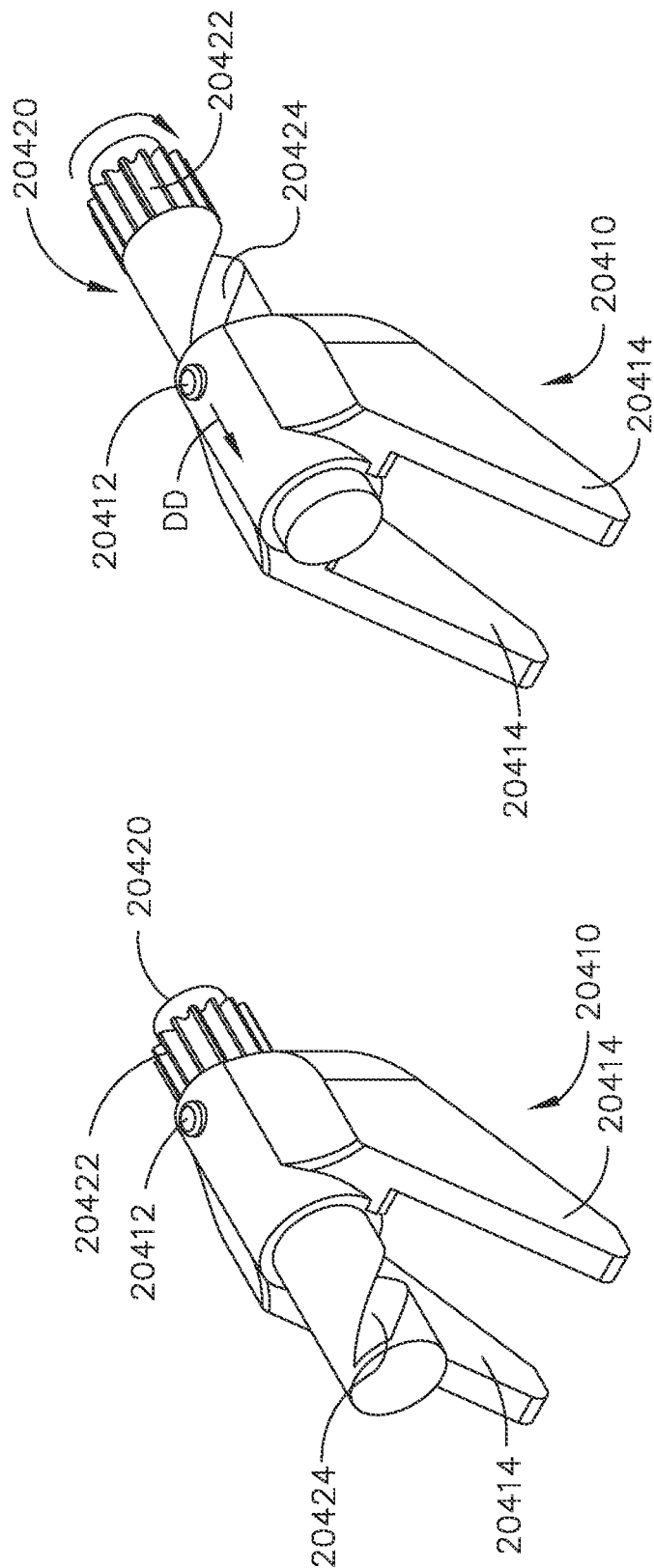

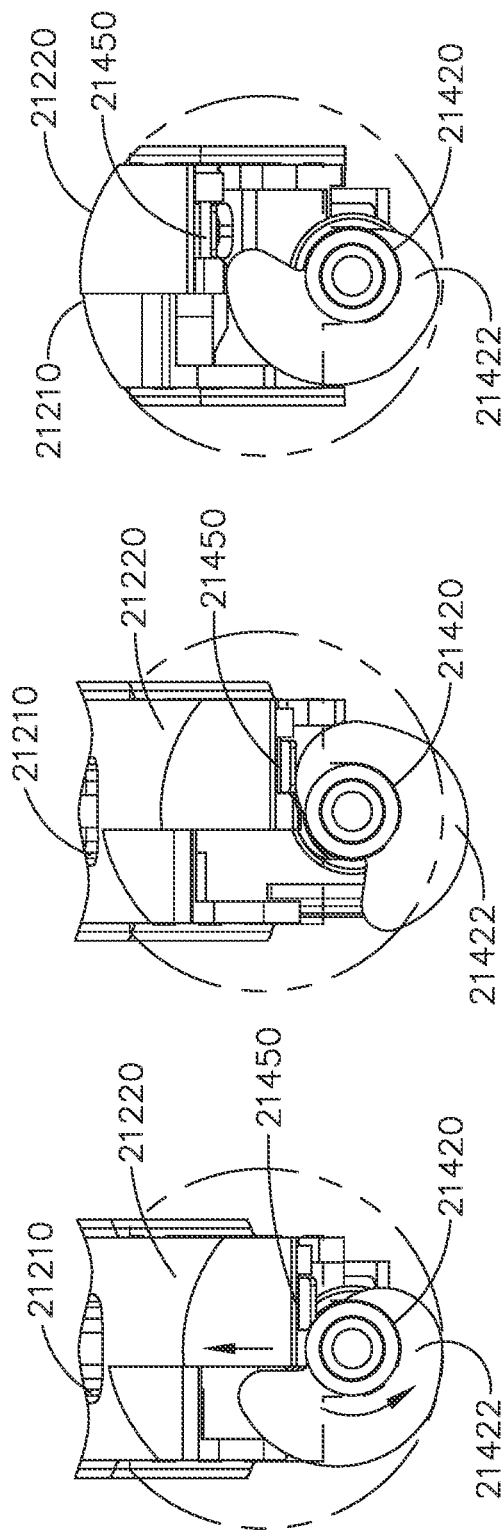

SURGICAL INSTRUMENTS WITH DOUBLE SPHERICAL ARTICULATION JOINTS WITH PIVOTABLE LINKS

CROSS-REFERENCE TO RELATED APPLICATIONS

This non-provisional application is a continuation of U.S. Non-Provisional patent application Ser. No. 17/360,176, entitled SURGICAL INSTRUMENTS WITH DOUBLE SPHERICAL ARTICULATION JOINTS WITH PIVOTABLE LINKS, filed Jun. 28, 2021, issued as U.S. Pat. No. 11,737,748, on Aug. 29, 2023, which claims the benefit under 35 U.S.C. § 119(e) of U.S. Provisional Patent Application Ser. No. 63/057,430, entitled SURGICAL INSTRUMENTS WITH TORSION SPINE DRIVE ARRANGEMENTS, filed Jul. 28, 2020, and of U.S. Provisional Patent Application Ser. No. 63/057,432, entitled ARTICULATION JOINT ARRANGEMENTS FOR SURGICAL INSTRUMENTS, filed Jul. 28, 2020, the disclosures of which are incorporated by reference herein in their entireties.

BACKGROUND

The present invention relates to surgical instruments and, in various arrangements, to surgical stapling and cutting instruments and staple cartridges for use therewith that are designed to staple and cut tissue. The surgical instruments may be configured for use in open surgical procedures, but have applications in other types of surgery, such as laparoscopic, endoscopic, and robotic-assisted procedures and may include end effectors that are articulatable relative to a shaft portion of the instrument to facilitate precise positioning within a patient.

BRIEF DESCRIPTION OF THE DRAWINGS

The novel features of the various aspects are set forth with particularity in the appended claims. The described aspects, however, both as to organization and methods of operation, may be best understood by reference to the following description, taken in conjunction with the accompanying drawings in which:

FIG. 23 is a side view of the rotary drive screw of FIG. 22;

FIG. 24 is a partial cross-sectional side view of a portion of the lower flexible spine assembly and a portion of the firing member of FIG. 21 in driving engagement with a portion of the rotary drive screw;

FIG. 51 is a cross-sectional view of the proximal joint member of FIG. 49 and a portion of a first link of the articulation joint in a first position;

FIG. 52 is another cross-sectional view of the proximal joint member of FIG. 49 with the first link in another position;

FIG. 61 is a perspective view of a closure cam member in a starting position on a rotatable cam shaft corresponding to an open position of the anvil of the surgical end effector of FIG. 59;

FIG. 62 is another perspective view of the closure cam member in an ending position on the rotatable cam shaft that corresponds to the closed position of the anvil as shown in FIG. 60;

FIG. 72 is a partial end view of a portion of a rotary cam shaft and cam follower of the rotary drive system of FIG. 69 in a position when the anvil is in the open position;

FIG. 73 is another partial end view of the rotary cam shaft and cam follower of FIG. 72 after the closure process has started;

FIG. 74 is another partial end view of the rotary cam shaft and cam follower of FIG. 72 after a cam lobe on the rotary cam shaft has cammed the cam follower into a position wherein the anvil is pivoted to an open position;

DETAILED DESCRIPTION

Figure 1:
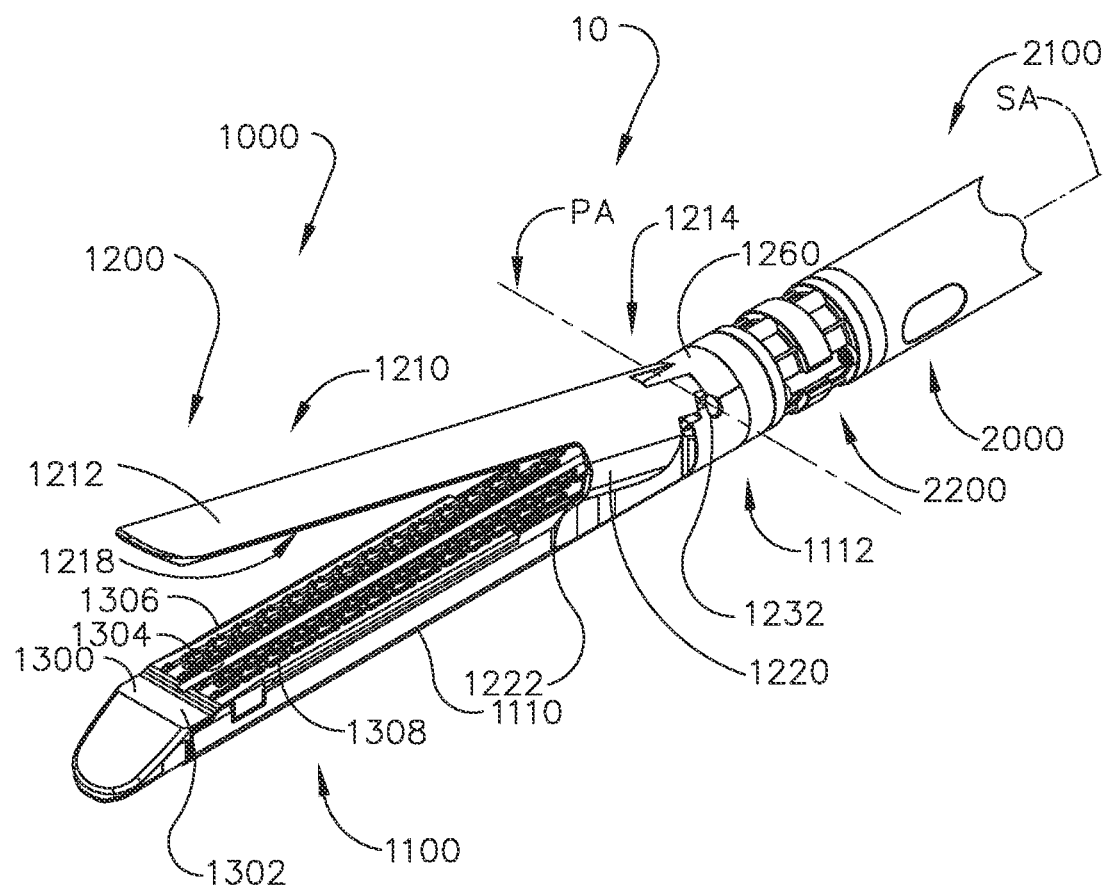
FIG. 1 is a perspective view of a surgical end effector portion of a surgical instrument in accordance with at least one aspect of the present disclosure.
Figure 2:
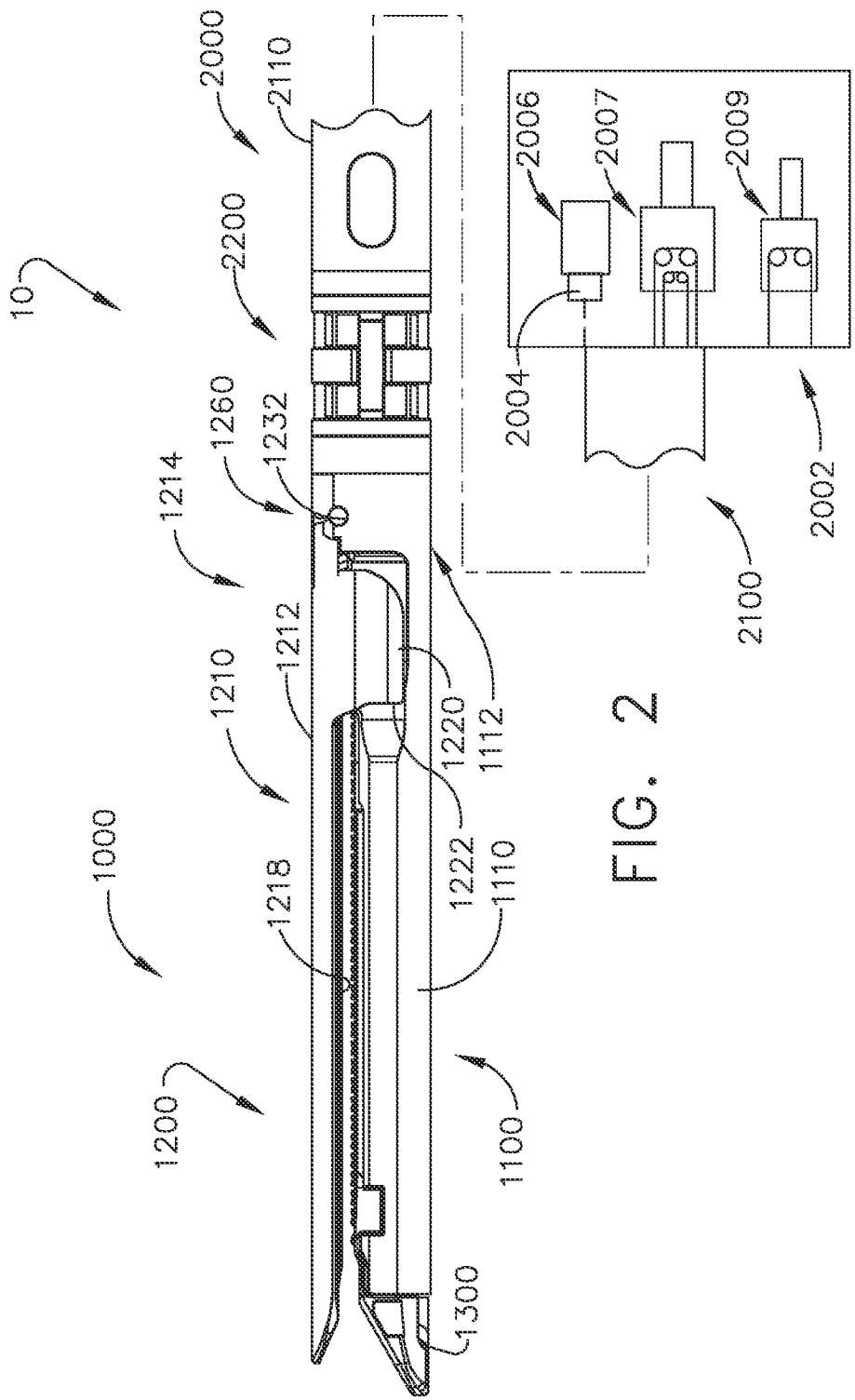
FIG. 2 is a side view of the surgical end effector portion instrument of FIG. 1 in a closed orientation.
Figure 3:
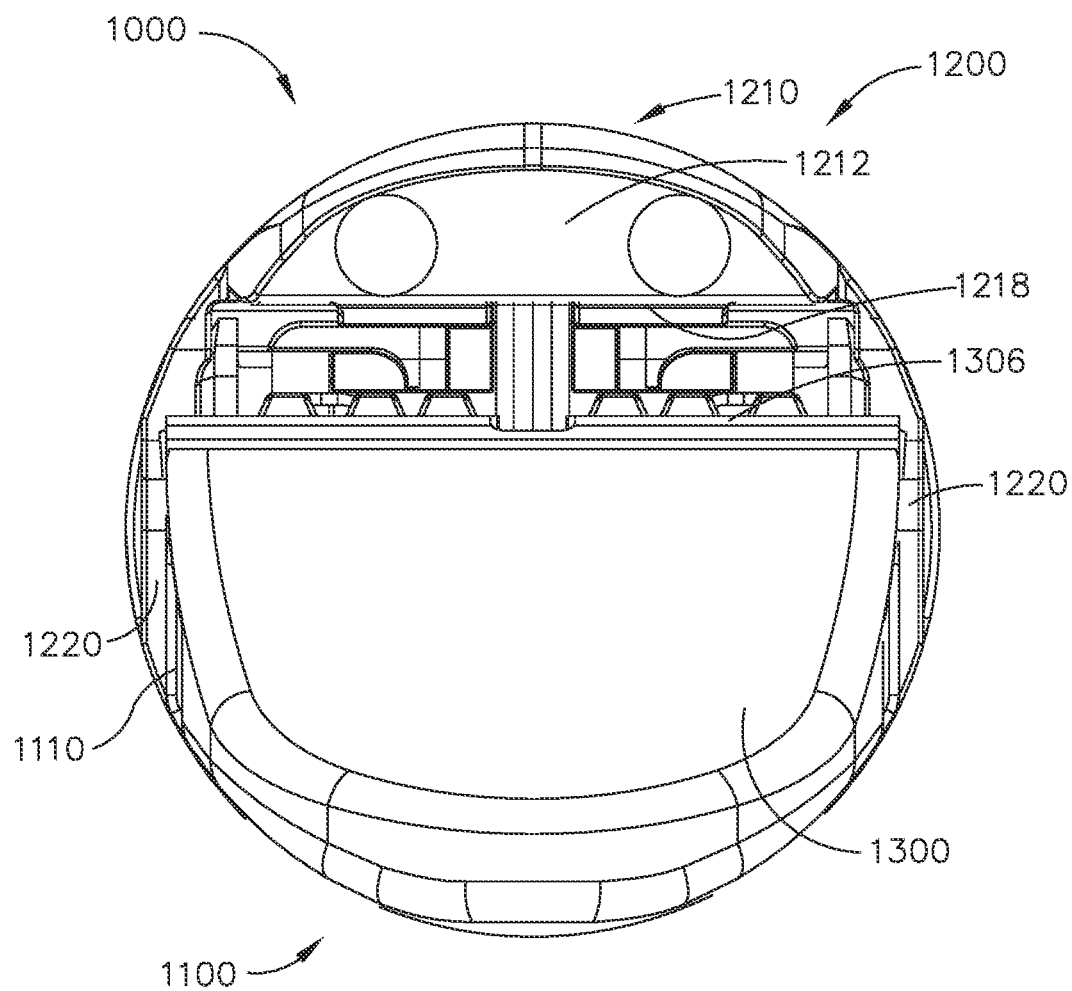
FIG. 3 is an end view of the surgical end effector of FIG. 2.
Figure 4:
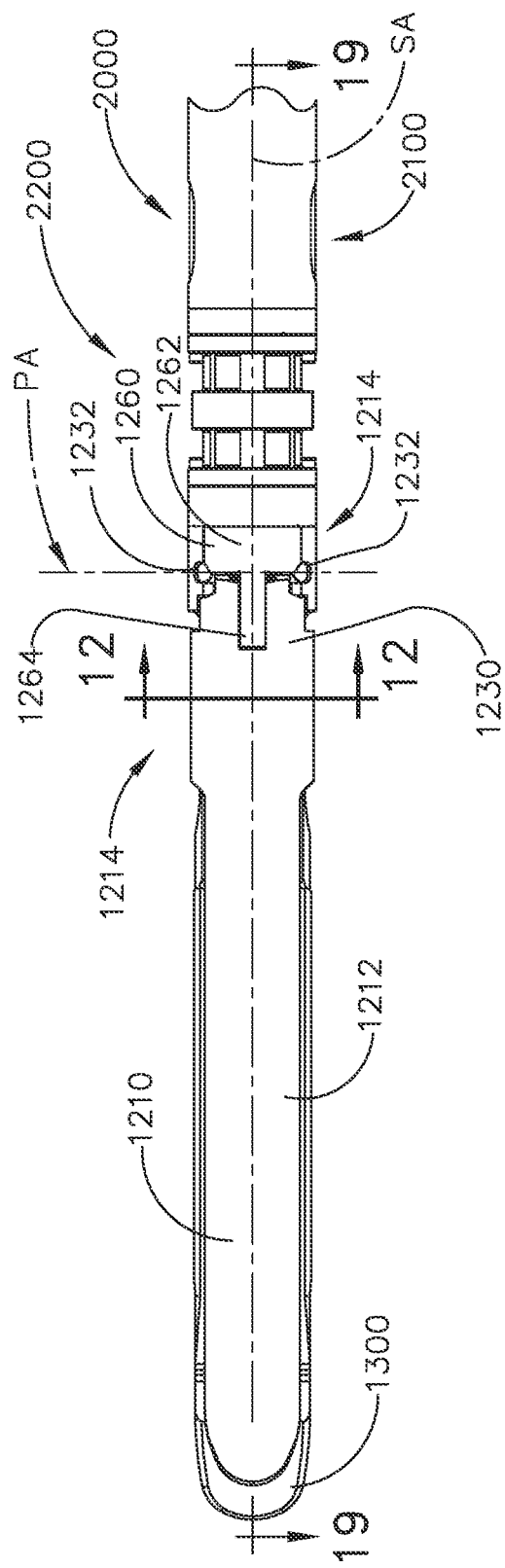
FIG. 4 is a top view of the surgical end effector of FIG. 2.

Applicant of the present application owns the following U.S. Patent Applications that were filed on even date herewith and which are each herein incorporated by reference in their respective entireties:

U.S. Patent Application entitled SURGICAL INSTRUMENTS WITH TORSION SPINE DRIVE ARRANGEMENTS, U.S. patent application Ser. No. 17/360,133 filed on Jun. 28, 2021, issued as U.S. Pat. No. 11,638,582 on May 2, 2023;

U.S. Patent Application entitled SURGICAL INSTRUMENTS WITH FIRING MEMBER CLOSURE FEATURES, U.S. patent application Ser. No. 17/360,139 filed on Jun. 28, 2021, published as 2022/0031322 on Feb. 3, 2022;

U.S. Patent Application entitled SURGICAL INSTRUMENTS WITH SEGMENTED FLEXIBLE DRIVE ARRANGEMENTS, U.S. patent application Ser. No. 17/360,149 filed on Jun. 28, 2021, issued as U.S. Pat. No. 11,660,090 on May 30, 2023;

U.S. Patent Application entitled SURGICAL INSTRUMENTS WITH FLEXIBLE BALL CHAIN DRIVE ARRANGEMENTS, U.S. patent application Ser. No. 17/360,162 filed on Jun. 28, 2021, published as U.S. Pub. No. 2022/0031319 on Feb. 3, 2022;

U.S. Patent Application entitled SURGICAL INSTRUMENTS WITH DOUBLE PIVOT ARTICULATION JOINT ARRANGEMENTS, U.S. patent application Ser. No. 17/360,192 filed on Jun. 28, 2021, published as U.S. Pub. No. 2022/0031350 on Feb. 3, 2023;

U.S. Patent Application entitled SURGICAL INSTRUMENTS WITH COMBINATION FUNCTION ARTICULATION JOINT ARRANGEMENTS, U.S. patent application Ser. No. 17/360,197 filed on Jun. 28, 2021, published as U.S. Pub. No. 2022/0031323 on Feb. 3, 2023;

U.S. Patent Application entitled METHOD OF OPERATING A SURGICAL INSTRUMENT, U.S. patent Ser. No. 17/360,199 filed on Jun. 28, 2021, published as U.S. Pub. No. 2022/0031315 on Feb. 3, 2023;

U.S. Patent Application entitled SURGICAL INSTRUMENTS WITH DUAL SPHERICAL ARTICULATION JOINT ARRANGEMENTS, U.S. patent Ser. No. 17/360,211 filed on Jun. 28, 2021, published as U.S. Pub. No. 2022/0031324 on Feb. 3, 2023;

U.S. Patent Application entitled SURGICAL INSTRUMENTS WITH FLEXIBLE FIRING MEMBER ACTUATOR CONSTRAINT ARRANGEMENTS, U.S. patent Ser. No. 17/360,220 filed on Jun. 28, 2021, published as U.S. Pub. No. 2022/0031320 on Feb. 3, 2023;

U.S. Patent Application entitled ARTICULATABLE SURGICAL INSTRUMENTS WITH ARTICULATION JOINTS COMPRISING FLEXIBLE EXOSKELETON ARRANGEMENTS, U.S. patent Ser. No. 17/360,244 filed on Jun. 28, 2021, published as U.S. Pub. No. 2022/0031346 on Feb. 3, 2023; and U.S. Patent Application entitled SURGICAL INSTRUMENTS WITH DIFFERENTIAL ARTICULATION JOINT ARRANGEMENTS FOR ACCOMMODATING FLEXIBLE ACTUATORS, U.S. patent Ser. No. 17/360,249 filed on Jun. 28, 2021, published as U.S. Pub. No. 2022/0031351 on Feb. 3, 2023.

Numerous specific details are set forth to provide a thorough understanding of the overall structure, function, manufacture, and use of the embodiments as described in the specification and illustrated in the accompanying drawings. Well-known operations, components, and elements have not been described in detail so as not to obscure the embodiments described in the specification. The reader will understand that the embodiments described and illustrated herein are non-limiting examples, and thus it can be appreciated that the specific structural and functional details disclosed herein may be representative and illustrative. Variations and changes thereto may be made without departing from the scope of the claims.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a surgical system, device, or apparatus that "comprises," "has," "includes" or "contains" one or more elements possesses those one or more elements, but is not limited to possessing only those one or more elements. Likewise, an element of a system, device, or apparatus that "comprises," "has," "includes" or "contains" one or more features possesses those one or more features, but is not limited to possessing only those one or more features.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

References to items in the singular should be understood to include items in the plural, and vice versa, unless explicitly stated otherwise or clear from the text. Grammatical conjunctions are intended to express any and all disjunctive and conjunctive combinations of conjoined clauses, sentences, words, and the like, unless otherwise stated or clear from the context. Thus, the term "or" should generally be understood to mean "and/or", etc.

Recitation of ranges of values herein are not intended to be limiting, referring instead individually to any and all values falling within the range, unless otherwise indicated herein, and each separate value within such a range is incorporated into the disclosure as if it were individually recited herein. The words "about," "approximately" or the like, when accompanying a numerical value, are to be construed as indicating a deviation as would be appreciated by one of ordinary skill in the art to operate satisfactorily for an intended purpose. Similarly, words of approximation such as "approximately" or "substantially" when used in reference to physical characteristics, should be construed to contemplate a range of deviations that would be appreciated by one of ordinary skill in the art to operate satisfactorily for a corresponding use, function, purpose or the like.

The use of any and all examples, or exemplary language ("e.g.," "such as," or the like) provided herein, is intended merely to better illuminate the embodiments and does not pose a limitation on the scope of the embodiments. No language in the specification should be construed as indicating any unclaimed element as essential to the practice of the embodiments.

Various exemplary devices and methods are provided for performing laparoscopic and minimally invasive surgical procedures. However, the reader will readily appreciate that the various methods and devices disclosed herein can be used in numerous surgical procedures and applications including, for example, in connection with open surgical procedures. As the present Detailed Description proceeds, the reader will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongate shaft of a surgical instrument can be advanced.

It is common practice during various laparoscopic surgical procedures to insert a surgical end effector portion of a surgical instrument through a trocar that has been installed in the abdominal wall of a patient to access a surgical site located inside the patient's abdomen. In its simplest form, a trocar is a pen-shaped instrument with a sharp triangular point at one end that is typically used inside a hollow tube, known as a cannula or sleeve, to create an opening into the body through which surgical end effectors may be introduced. Such arrangement forms an access port into the body cavity through which surgical end effectors may be inserted. The inner diameter of the trocar's cannula necessarily limits the size of the end effector and drive-supporting shaft of the surgical instrument that may be inserted through the trocar.

Regardless of the specific type of surgical procedure being performed, once the surgical end effector has been inserted into the patient through the trocar cannula, it is often necessary to move the surgical end effector relative to the shaft assembly that is positioned within the trocar cannula in order to properly position the surgical end effector relative to the tissue or organ to be treated. This movement or positioning of the surgical end effector relative to the portion of the shaft that remains within the trocar cannula is often referred to as "articulation" of the surgical end effector. A variety of articulation joints have been developed to attach a surgical end effector to an associated shaft in order to facilitate such articulation of the surgical end effector. As one might expect, in many surgical procedures, it is desirable to employ a surgical end effector that has as large a range of articulation as possible.

Due to the size constraints imposed by the size of the trocar cannula, the articulation joint components must be sized so as to be freely insertable through the trocar cannula. These size constraints also limit the size and composition of various drive members and components that operably interface with the motors and/or other control systems that are supported in a housing that may be handheld or comprise a portion of a larger automated system. In many instances, these drive members must operably pass through the articulation joint to be operably coupled to or operably interface with the surgical end effector. For example, one such drive member is commonly employed to apply articulation control motions to the surgical end effector. During use, the articulation drive member may be unactuated to position the surgical end effector in an unarticulated position to facilitate insertion of the surgical end effector through the trocar and then be actuated to articulate the surgical end effector to a desired position once the surgical end effector has entered the patient.

Thus, the aforementioned size constraints form many challenges to developing an articulation system that can effectuate a desired range of articulation, yet accommodate a variety of different drive systems that are necessary to operate various features of the surgical end effector. Further, once the surgical end effector has been positioned in a desired articulated position, the articulation system and articulation joint must be able to retain the surgical end effector in that locked position during the actuation of the end effector and completion of the surgical procedure. Such articulation joint arrangements must also be able to withstand external forces that are experienced by the end effector during use.

A variety of surgical end effectors exist that are configured to cut and staple tissue. Such surgical end effectors commonly include a first jaw feature that supports a surgical staple cartridge and a second jaw that comprises an anvil. The jaws are supported relative to each other such that they can move between an open position and a closed position to position and clamp target tissue therebetween. Many of these surgical end effectors employ an axially moving firing member. In some end effector designs, the firing member is configured to engage the first and second jaws such that as the firing member is initially advanced distally, the firing member moves the jaws to the closed position. Other end effector designs employ a separate closure system that is independent and distinct from the system that operates the firing member.

The staple cartridge comprises a cartridge body. The cartridge body includes a proximal end, a distal end, and a deck extending between the proximal end and the distal end. In use, the staple cartridge is positioned on a first side of the tissue to be stapled and the anvil is positioned on a second side of the tissue. The anvil is moved toward the staple cartridge to compress and clamp the tissue against the deck. Thereafter, staples removably stored in the cartridge body can be deployed into the tissue. The cartridge body includes staple cavities defined therein wherein staples are removably stored in the staple cavities. The staple cavities are arranged in six longitudinal rows. Three rows of staple cavities are positioned on a first side of a longitudinal slot and three rows of staple cavities are positioned on a second side of the longitudinal slot. Other arrangements of staple cavities and staples may be possible.

The staples are supported by staple drivers in the cartridge body. The drivers are movable between a first, or unfired position, and a second, or fired, position to eject the staples from the staple cavities. The drivers are retained in the cartridge body by a retainer which extends around the bottom of the cartridge body and includes resilient members configured to grip the cartridge body and hold the retainer to the cartridge body. The drivers are movable between their unfired positions and their fired positions by a sled. The sled is movable between a proximal position adjacent the proximal end and a distal position adjacent the distal end. The sled comprises a plurality of ramped surfaces configured to slide under the drivers and lift the drivers, and the staples supported thereon, toward the anvil.

Further to the above, in these surgical end effectors, the sled is moved distally by the firing member. The firing member is configured to contact the sled and push the sled toward the distal end. The longitudinal slot defined in the cartridge body is configured to receive the firing member. The anvil also includes a slot configured to receive the firing member. The firing member further comprises a first cam which engages the first jaw and a second cam which engages the second jaw. As the firing member is advanced distally, the first cam and the second cam can control the distance, or tissue gap, between the deck of the staple cartridge and the anvil. The firing member also comprises a knife configured to incise the tissue captured intermediate the staple cartridge and the anvil. It is desirable for the knife to be positioned at least partially proximal to the ramped surfaces such that the staples are ejected ahead of the knife.

Many surgical end effectors employ an axially movable firing beam that is attached to the firing member and is used to apply axial firing and retraction motions to the firing member. Many of such firing beams comprise a laminated construction that affords the firing beam with some degree of flexure about the articulation joint. As the firing beam traverses the articulation joint, the firing beam can apply de-articulation forces to the joint and can cause the beam to buckle. To prevent the firing beam from buckling under pressure, the articulation joint is commonly provided with lateral supports or "blow-out" plate features to support the portion of the beam that traverses the articulation joint. To advance the firing beam through an angle of greater than sixty degrees, for example, a lot of axial force is required. This axial force must be applied to the firing member in a balanced manner to avoid the firing member from binding with the jaws as the firing member moves distally. Any binding of the firing member with the jaws can lead to component damage and wear as well as require an increased amount of axial drive force to drive the firing member through the clamped tissue.

Other end effector designs employ a firing member that is rotary powered. In many of such designs, a rotary drive shaft extends through the articulation joint and interfaces with a rotatable firing member drive shaft that is rotatably supported within one of the jaws. The firing member threadably engages the rotatable firing member drive shaft and, as the rotatable firing member drive shaft is rotated, the firing member is driven through the end effector. Such arrangements require the supporting jaw to be larger to accommodate the firing member drive shaft. In such devices, a lower end of the firing member commonly operably interfaces with the drive shaft which can also result in an application of forces that tend to unbalance the firing member as it is driven distally.

FIGS. 1-4 illustrate one form of a surgical instrument 10 that may address many of the challenges facing surgical instruments with articulatable end effectors that are configured to cut and fasten tissue. In various embodiments, the surgical instrument 10 may comprise a handheld device. In other embodiments, the surgical instrument 10 may comprises an automated system sometimes referred to as a robotically-controlled system, for example. In various forms, the surgical instrument 10 comprises a surgical end effector 1000 that is operably coupled to an elongate shaft assembly 2000. The elongate shaft assembly 2000 may be operably attached to a housing 2002. In one embodiment, the housing 2002 may comprise a handle that is configured to be grasped, manipulated, and actuated by the clinician. In other embodiments, the housing 2002 may comprise a portion of a robotic system that houses or otherwise operably supports at least one drive system that is configured to generate and apply at least one control motion which could be used to actuate the surgical end effectors disclosed herein and their respective equivalents. In addition, various components may be "housed" or contained in the housing or various components may be "associated with" a housing. In such instances, the components may not be contained with the housing or supported directly by the housing. For example, the surgical instruments disclosed herein may be employed with various robotic systems, instruments, components and methods disclosed in U.S. Pat. No. 9,072,535, entitled SURGICAL STAPLING INSTRUMENTS WITH ROTATABLE STAPLE DEPLOYMENT ARRANGEMENTS, which is incorporated by reference herein in its entirety.

In one form, the surgical end effector 1000 comprises a first jaw 1100 and a second jaw 1200. In the illustrated arrangement, the first jaw 1100 comprises an elongate channel 1110 that comprises a proximal end 1112 and a distal end 1114 and is configured to operably support a surgical staple cartridge 1300 therein. The surgical staple cartridge 1300 comprises a cartridge body 1302 that has an elongate slot 1304 therein. A plurality of surgical staples or fasteners (not shown) are stored therein on drivers (not shown) that are arranged in rows on each side of the elongate slot 1304. The drivers are each associated with corresponding staple cavities 1308 that open through a cartridge deck surface 1306. The surgical staple cartridge 1300 may be replaced after the staples/fasteners have been discharged therefrom. Other embodiments are contemplated wherein the elongate channel 1110 and/or the entire surgical end effector 1000 may is discarded after the surgical staple cartridge 1300 has been used. Such end effector arrangements may be referred to as "disposable loading units", for example.

In the illustrated arrangement, the second jaw 1200 comprises an anvil 1210 that comprises an elongate anvil body 1212 that comprises a proximal end 1214 and a distal end 1216. In one arrangement, a pair of stiffening rods or members 1213 may be supported in the anvil body 1212 to provide the anvil body 1212 with added stiffness and rigidity. The anvil body 1212 comprises a staple-forming undersurface 1218 that faces the first jaw 1100 and may include a series of staple-forming pockets (not shown) that corresponds to each of the staples or fasteners in the surgical staple cartridge 1300. The anvil body 1212 may further include a pair of downwardly extending tissue stop features 1220 that are formed adjacent the proximal end 1214 of the anvil body 1212. One tissue stop feature 1220 extends from each side of the anvil body 1212 such that a distal end 1222 on each tissue stop corresponds to the proximal-most staples/fasteners in the surgical staple cartridge 1300. When the anvil 1210 is moved to a closed position onto tissue positioned between the staple-forming undersurface 1218 of the anvil 1210 and the cartridge deck surface 1306 of the surgical staple cartridge 1300, the tissue contacts the distal ends 1222 of the tissue stop features 1220 to prevent the tissue from migrating proximally past the proximal-most staples/fasteners to thereby ensure that the tissue that is cut is also stapled. When the surgical staple cartridge is "fired" as will be discussed in further detail below, the staples/fasteners supported within each staple cavity are driven out of the staple cavity 1308 through the clamped tissue and into forming contact with the staple-forming undersurface 1218 of the anvil 1210.

Figure 5:
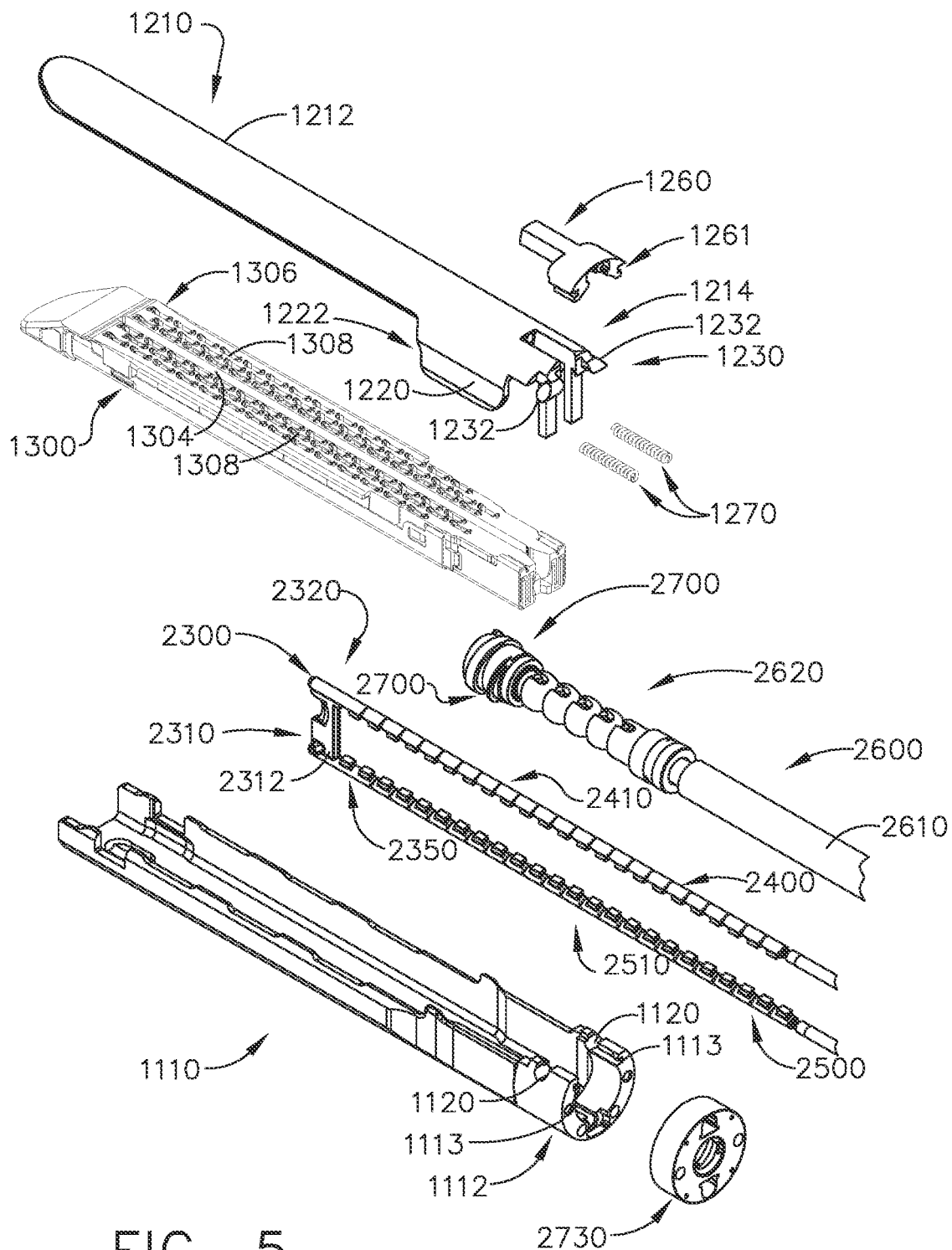
FIG. 5 is an exploded assembly view of a portion of the surgical instrument of FIG. 1.
Figure 6:
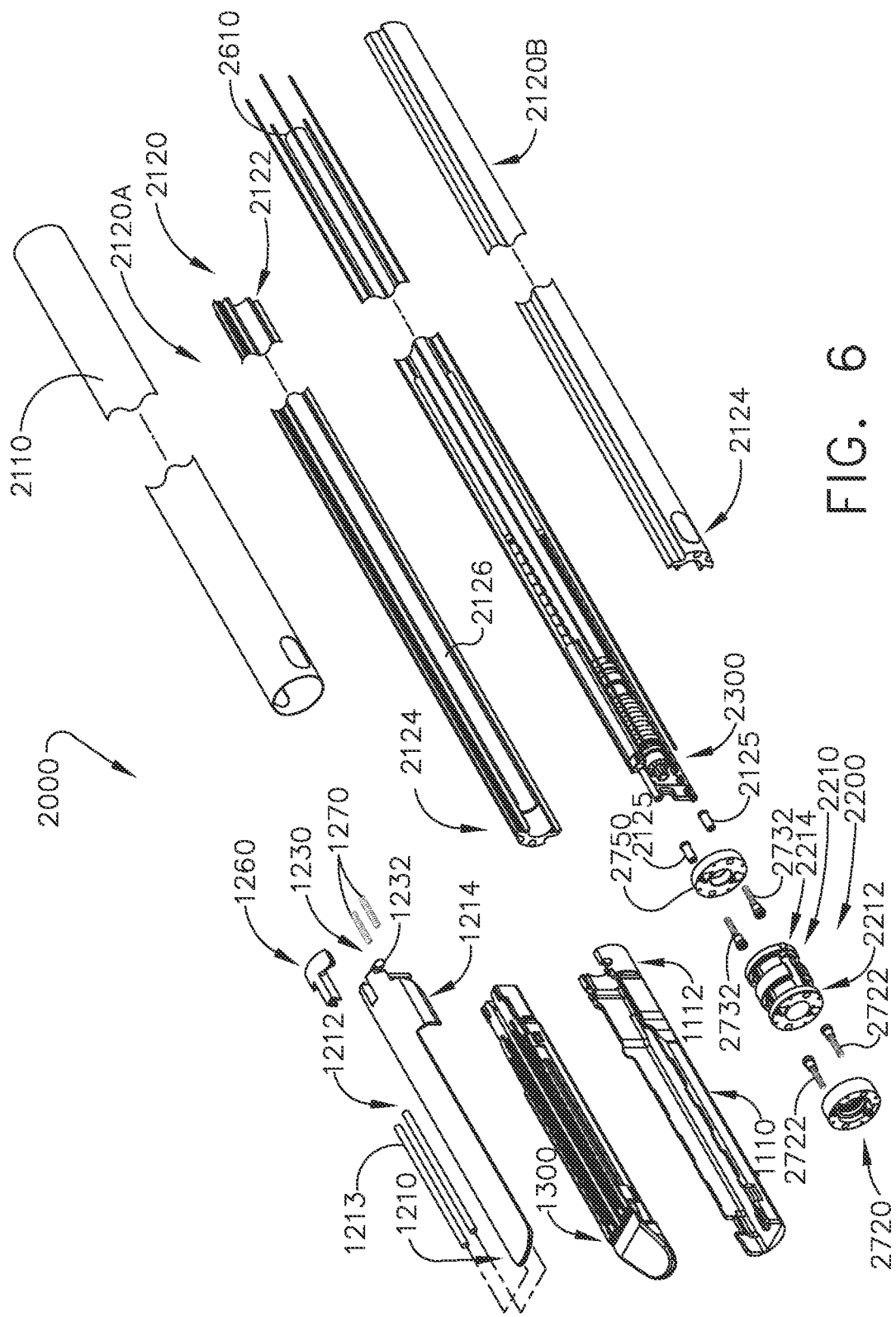
FIG. 6 is an exploded assembly view of an elongate shaft assembly of the surgical instrument of FIG. 1.

As can be seen in FIGS. 5 and 6, the proximal end 1214 of the anvil body 1212 comprises an anvil mounting portion 1230 that includes a pair of laterally extending mounting pins 1232 that are configured to be received in corresponding mounting cradles or pivot cradles 1120 formed in the proximal end 1112 of the elongate channel 1110. The mounting pins 1232 are pivotally retained within the mounting cradles 1120 by an anvil cap 1260 that may be attached to the proximal end 1112 of the elongate channel 1110 by mechanical snap features 1261 that are configured to engage retention formations 1113 on the elongate channel 1110. See FIG. 5. In other arrangements, the anvil cap 1260 may be attached to the elongate channel 1110 by welding, adhesive, etc. Such arrangement facilitates pivotal travel of the anvil 1210 relative to the surgical staple cartridge 1300 mounted in the elongate channel 1110 about a pivot axis PA between an open position (FIG. 1) and a closed position (FIGS. 2-5). Such pivot axis PA may be referred to herein as being "fixed" in that the pivot axis does not translate or otherwise move as the anvil 1200 is pivoted from an open position to a closed position.

In the illustrated arrangement, the elongate shaft assembly 2000 defines a shaft axis SA and comprises a proximal shaft portion 2100 that may operably interface with a housing of the control portion (e.g., handheld unit, robotic tool driver, etc.) of the surgical instrument 10. The elongate shaft assembly 2000 further comprises an articulation joint 2200 that is attached to the proximal shaft portion 2100 and the surgical end effector 1000. In various instances, the proximal shaft portion 2100 comprises a hollow outer tube 2110 that may be operably coupled to a housing 2002. See FIG. 2. As can be seen in FIG. 6, the proximal shaft portion 2100 may further comprise a rigid proximal support shaft 2120 that is supported within the hollow outer tube 2110 and extends from the housing to the articulation joint 2200. The proximal support shaft 2120 may comprise a first half 2120A and a second half 2120B that may be coupled together by, for example, welding, adhesive, etc. The proximal support member 2120 comprises a proximal end 2122 and a distal end 2124 and includes an axial passage 2126 that extends therethrough from the proximal end 2122 to the distal end 2124.

As was discussed above, many surgical end effectors employ a firing member that is pushed distally through a surgical staple cartridge by an axially movable firing beam. The firing beam is commonly attached to the firing member in the center region of the firing member body. This attachment location can introduce an unbalance to the firing member as it is advanced through the end effector. Such unbalance can lead to undesirable friction between the firing member and the end effector jaws. The creation of this additional friction may require an application of a higher firing force to overcome such friction as well as can cause undesirable wear to portions of the jaws and/or the firing member. An application of higher firing forces to the firing beam may result in unwanted flexure in the firing beam as it traverses the articulation joint. Such additional flexure may cause the articulation joint to de-articulate—particularly when the surgical end effector is articulated at relatively high articulation angles. The surgical instrument 10 employs a firing system 2300 that may address many if not all of these issues as well as others.

As can be seen in FIGS. 5-11, in at least one embodiment, the firing system 2300 comprises a firing member 2310 that includes a vertically-extending firing member body 2312 that comprises a top firing member feature 2320 and a bottom firing member feature 2350. A tissue cutting blade 2314 is attached to or formed in the vertically-extending firing member body 2312. See FIGS. 9 and 11. In at least one arrangement, it is desirable for the firing member 2310 to pass through the anvil body 1212 with low friction, high strength and high stiffness. In the illustrated arrangement, the top firing member feature 2320 comprises a top tubular body 2322 that has a top axial passage 2324 extending therethrough. See FIG. 10. The bottom firing member feature 2350 comprises a bottom tubular body 2352 that has a bottom axial passage 2354 extending therethrough. In at least one arrangement, the top firing member feature 2320 and the bottom firing member feature 2350 are integrally formed with the vertically-extending firing member body 2312. As can be seen in FIG. 12, the anvil body 1212 comprises an axially extending anvil slot 1240 that has a cross-sectional shape that resembles a "keyhole". Similarly, the elongate channel 1110 comprises an axially extending channel slot 1140 that also has a keyhole cross-sectional shape.

Traditional firing member arrangements employ long flexible cantilever wings that extend from a top portion and a bottom portion of the firing member. These cantilever wings slidably pass through slots in the anvil and channel that are commonly cut with a rectangular t-cutter which tended to produce higher friction surfaces. Such long cantilever wings have minimum surface area contact with the anvil and channel and can result in galling of those components. The keyhole-shaped channel slot 1140 and keyhole-shaped anvil slot 1240 may be cut with a round t-cutter and may be finished with a reamer/borer which will result in the creation of a lower friction surface. In addition, the top tubular body 2322 and the bottom tubular body 2352 tend to be stiffer than the prior cantilever wing arrangements and have increased surface area contact with the anvil and channel, respectively which can reduce galling and lead to a stronger sliding connection. Stated another way, because the anvil slot 1240 and the channel slot 1140 are keyhole-shaped and have less material removed than a traditional rectangular slot, the geometry and increased material may result in a stiffer anvil and channel when compared to prior arrangements.

Figure 9:
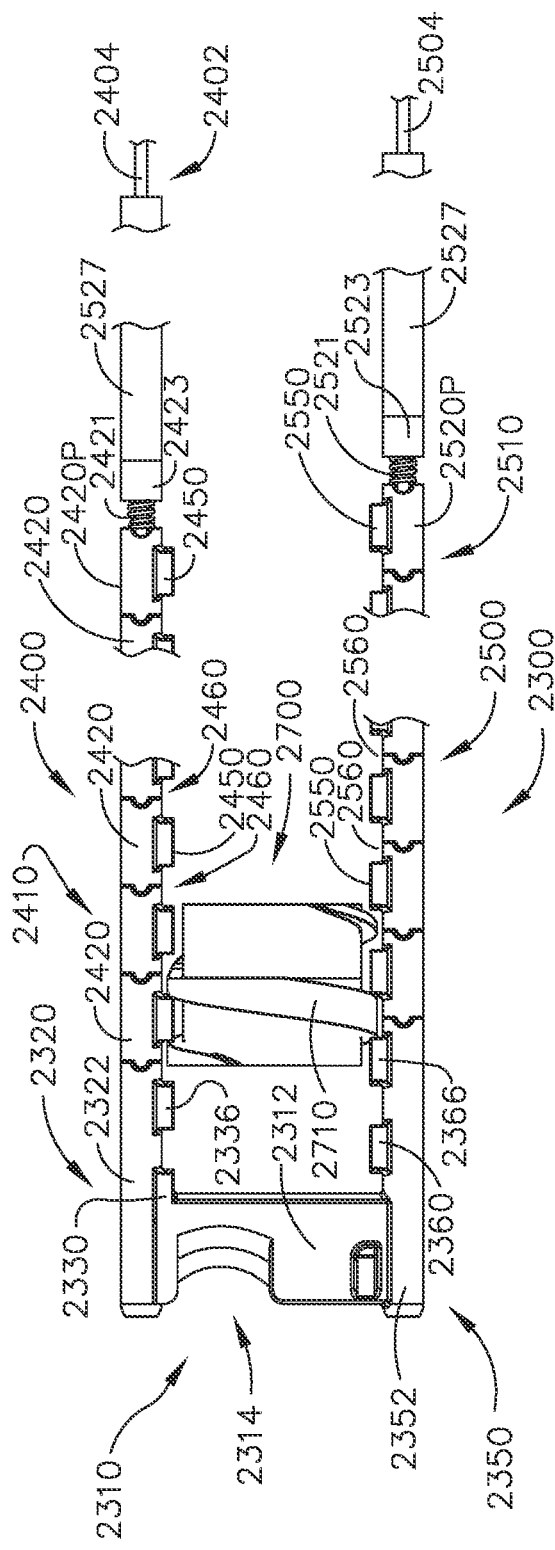
FIG. 9 is a side view of a firing member and upper and lower flexible spine assemblies of the firing system in engagement with a rotary drive screw of the rotary drive system of FIG. 8.
Figure 10:
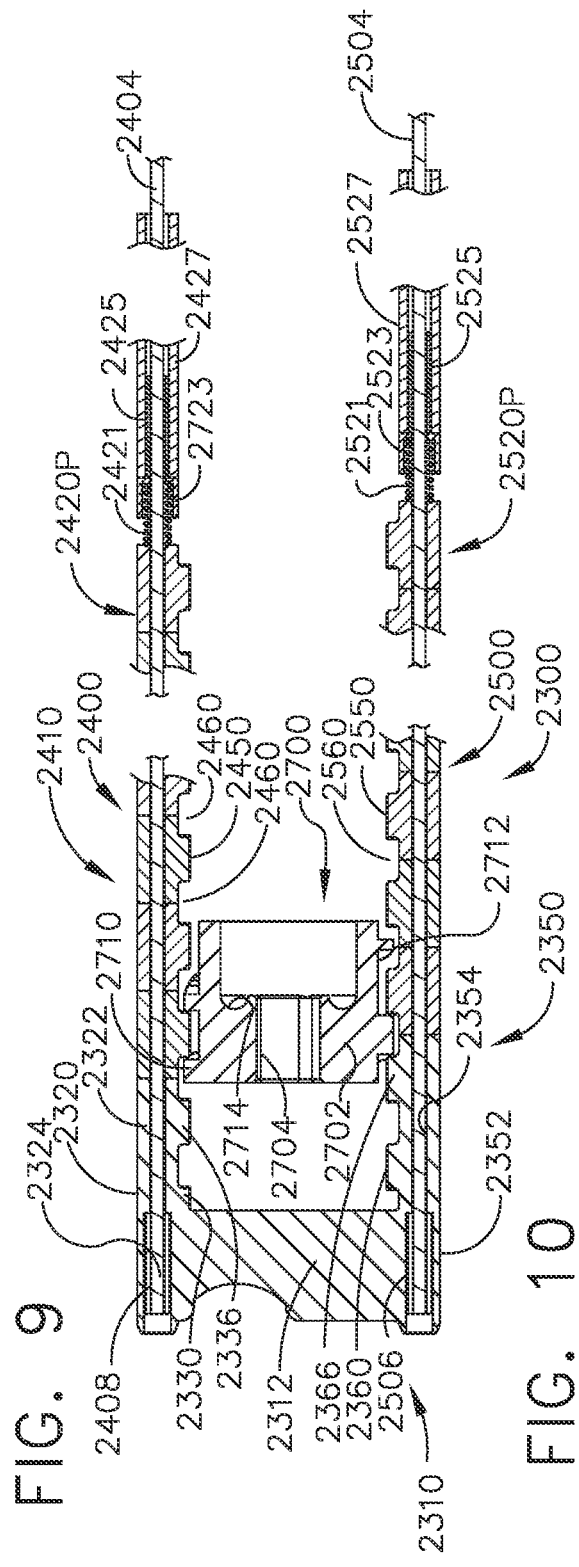
FIG. 10 is a cross-sectional view of the firing member and upper and lower flexible spine assemblies of FIG. 9.
Figure 11:
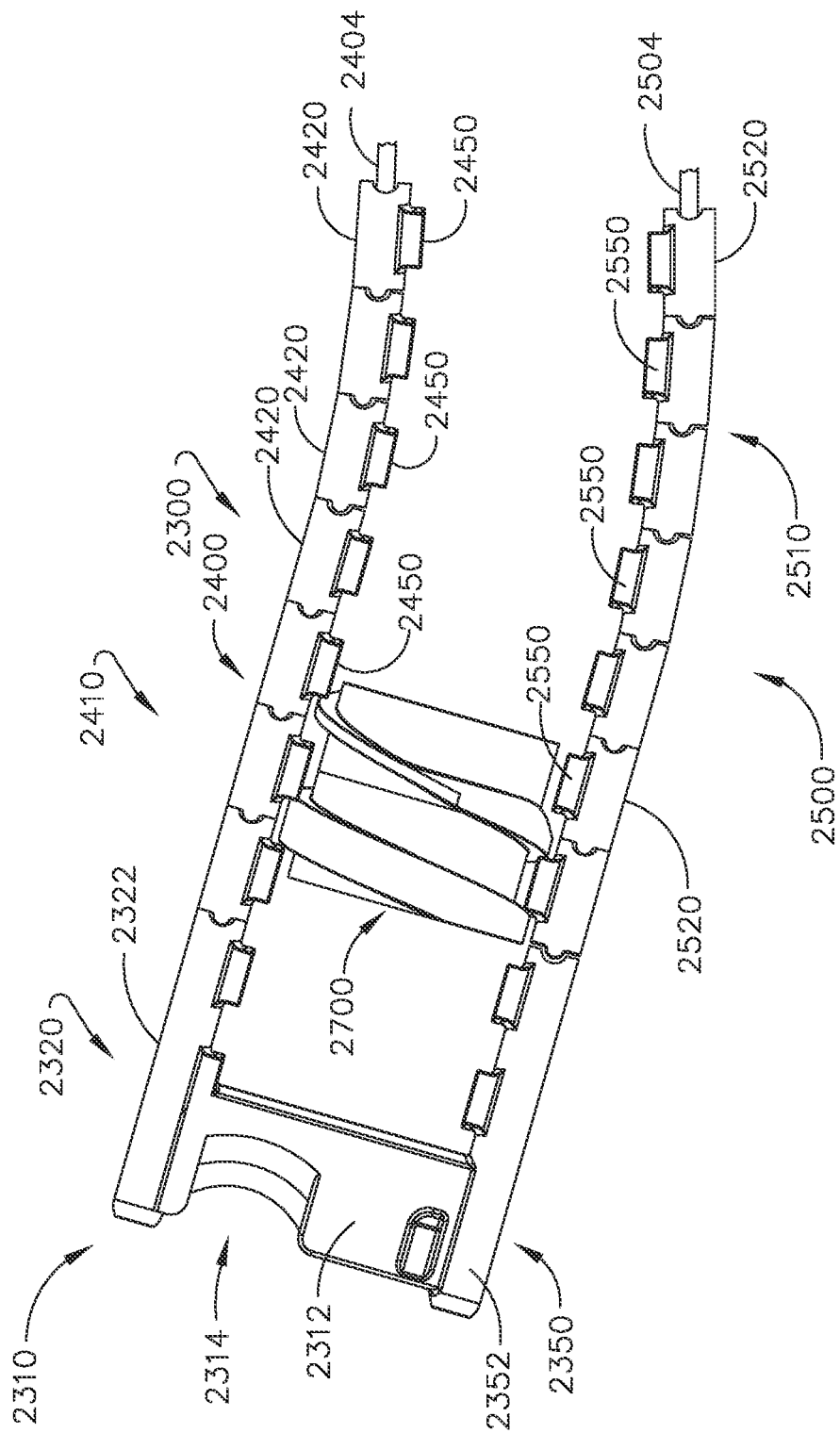
FIG. 11 is a side elevational view of the firing member and upper and lower flexible spine assemblies in engagement with the rotary drive screw of FIG. 9.
Figure 12:
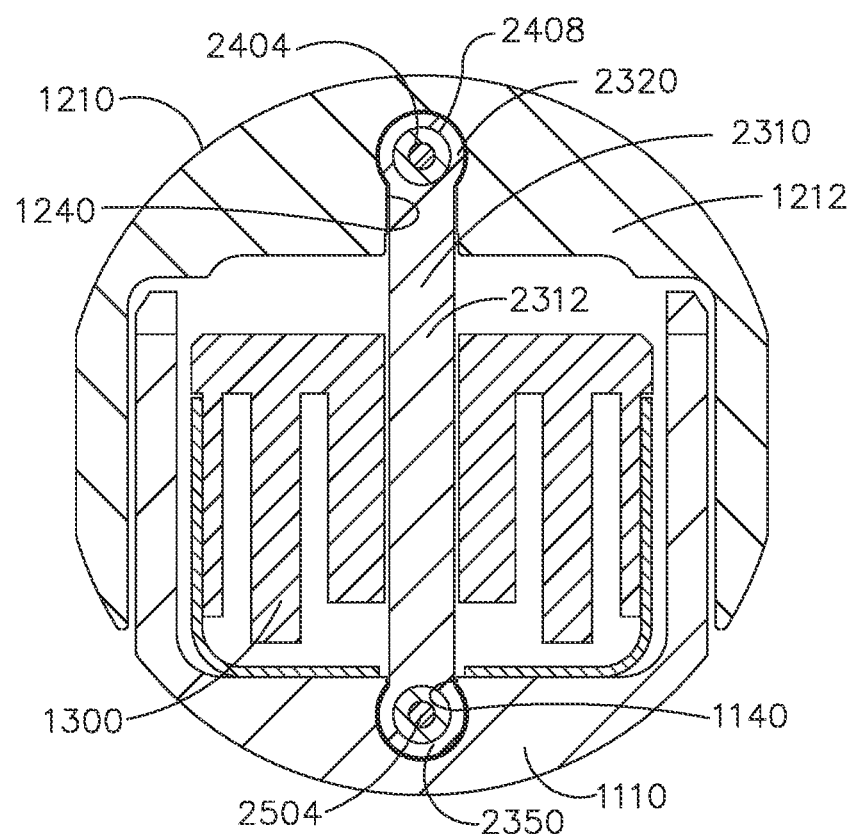
FIG. 12 is a cross-sectional end view of the surgical end effector of FIG. 4 taken along line 12-12 in FIG. 4.

Turning to FIGS. 9-11, in one arrangement, the firing system 2300 further comprises an upper flexible spine assembly 2400 that is operably coupled to the top firing member feature 2320 and a lower flexible spine assembly 2500 that is operably coupled to the bottom firing member feature 2350. In at least one embodiment, the upper flexible spine assembly 2400 comprises an upper series 2410 of upper vertebra members 2420 that are loosely coupled together by an upper flexible coupler member 2402 that is attached to the top firing member feature 2320. The upper flexible coupler member 2402 may comprises a top cable 2404 that extends through the top axial passage 2324 in the top firing member feature 2320 and a distal end 2406 of the top cable 2404 is attached to a retainer ferrule 2408 that is secured with the top axial passage 2324.

Figure 13:
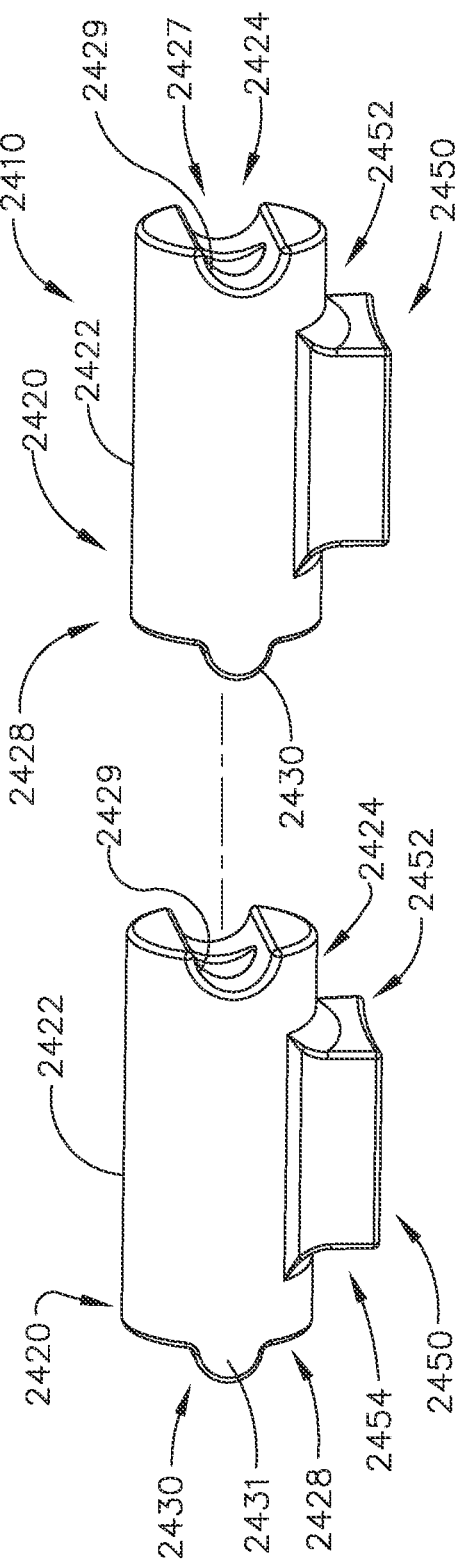
FIG. 13 is an exploded perspective view of two adjacent upper vertebra members of the upper flexible spine assembly of FIG. 10.

As can be seen in FIG. 13, each upper vertebra member 2420 comprises an upper vertebra body portion 2422 that has a proximal end 2424 and a distal end 2428. An upper hollow passage 2429 extends through the upper vertebra body portion 2422 to accommodate passage of the upper flexible coupler member 2402 therethrough. Each upper vertebra member 2420 further comprises a downwardly extending upper drive feature or upper vertebra member tooth 2450 that protrudes from the upper vertebra body portion 2422. Each upper vertebra member tooth 2450 has a helix-shaped proximal upper face portion 2452 and a helix-shaped distal upper face portion 2454. Each proximal end 2424 of the upper vertebra body portions 2422 has an upper proximal mating feature 2426 therein and each distal end 2428 has an upper distal mating feature 2430 formed therein. In at least one embodiment, the upper proximal mating feature 2426 comprises a concave recess 2427 and each upper distal mating feature 2430 comprises a convex mound 2431. When arranged in the upper series 2410, the convex mound 2431 on one upper vertebra member 2420 contacts and mates with the concave recess 2427 on an adjacent upper vertebra member 2420 in the upper series 2410 to maintain the upper vertebra members 2420 roughly in alignment so that the helix-shaped proximal upper face portion 2452 and a helix-shaped distal upper face portion 2454 on each respective upper tooth 2450 can be drivingly engaged by a rotary drive screw 2700 as will be discussed in further detail below.

Similarly, in at least one embodiment, the lower flexible spine assembly 2500 comprises a lower series 2510 of lower vertebra members 2520 that are loosely coupled together by a lower flexible coupler member 2502 that is attached to the bottom firing member feature 2350. The lower flexible coupler member 2502 may comprises a lower cable 2504 that extends through the bottom axial passage 2354 in the bottom firing member feature 2350 and a distal end 2506 of the bottom cable 2504 is attached to a retainer ferrule 2508 that is secured with the bottom axial passage 2354.

Figure 14:
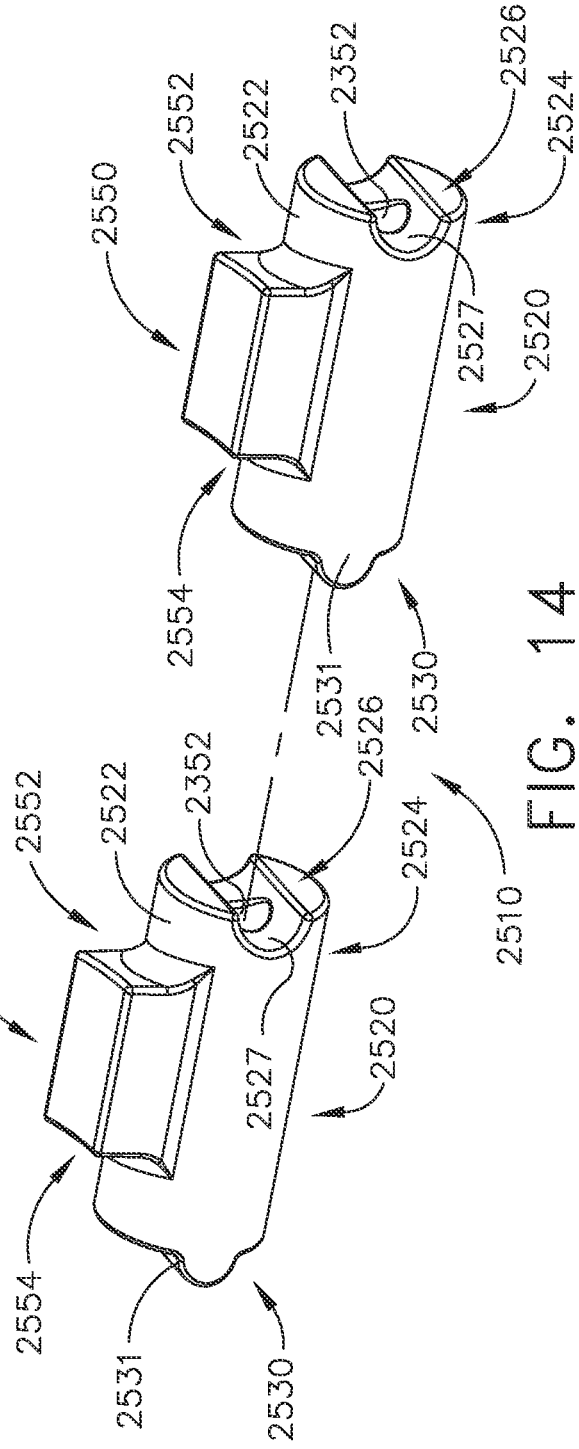
FIG. 14 is an exploded perspective view of two adjacent lower vertebra members of the lower flexible spine assembly of FIG. 10.

As can be seen in FIG. 14, each lower vertebra member 2520 comprises a lower vertebra body portion 2522 that has a proximal end 2524 and a distal end 2528. A lower hollow passage 2529 extends through the lower vertebra body portion 2522 to accommodate passage of the lower flexible coupler member 2502 therethrough. Each lower vertebra member 2520 further comprises an upwardly extending lower drive feature or lower vertebra member tooth 2550 that protrudes upward from the lower vertebra body portion 2522. Each lower vertebra member tooth 2550 has a helix-shaped proximal lower face portion 2552 and a helix-shaped distal lower face portion 2554. Each proximal end 2524 of the lower vertebra body portions 2522 has a lower proximal mating feature 2526 therein and each distal end 2528 has a lower distal mating feature 2530 formed therein. In at least one embodiment, the lower proximal mating feature 2526 comprises a concave recess 2527 and each lower distal mating feature 2530 comprises a convex mound 2531. When arranged in the lower series 2510, the convex mound 2531 on one lower vertebra member 2520 contacts and mates with the concave recess 2527 on an adjacent lower vertebra member 2520 in the lower series 2510 to maintain the lower vertebra members 2520 roughly in alignment so that the helix-shaped proximal lower face portion 2552 and a helix-shaped distal lower face portion 2554 on each respective lower vertebra member tooth 2550 can be drivingly engaged by a rotary drive screw 2700 as will be discussed in further detail below.

Figure 7:
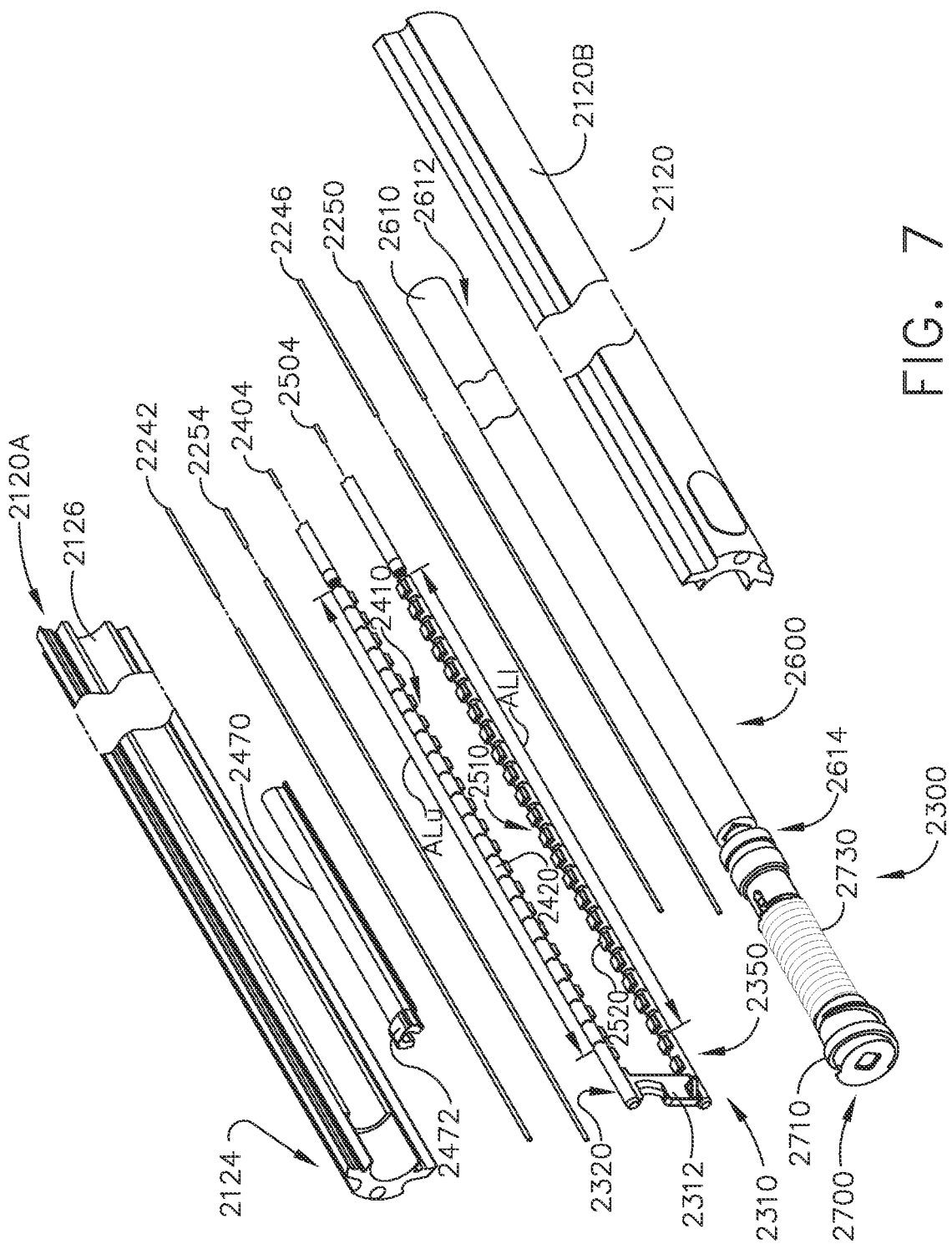
FIG. 7 is another exploded assembly view of the elongate shaft assembly of FIG. 6.
Figure 8:
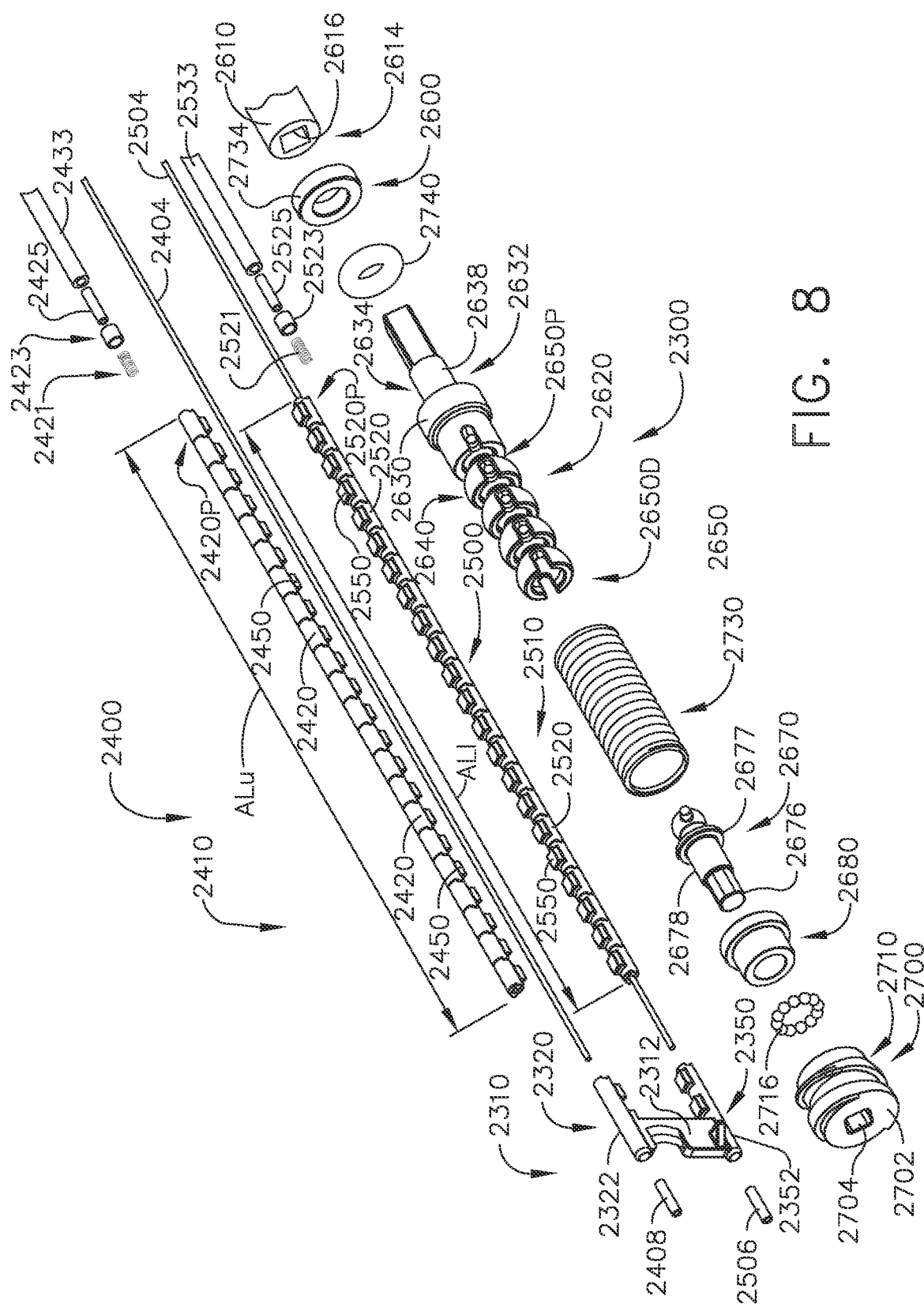
FIG. 8 is an exploded assembly view of a firing system and a rotary drive system according to at least one aspect of the present disclosure.

Now turning to FIGS. 5, 7, and 8, in at least one arrangement, the firing drive system 2300 further comprises a rotary drive screw 2700 that is configured to drivingly interface with the upper series 2410 of upper vertebra members 2420 and the lower series 2510 of lower vertebra members 2520. In the illustrated arrangement, the rotary drive screw 2700 is driven by a rotary drive system 2600 that comprises a proximal rotary drive shaft 2610 that is rotatably supported within the axial passage 2126 within the proximal support shaft 2120. See FIG. 7. The proximal rotary drive shaft 2610 comprises a proximal end 2612 and a distal end 2614. The proximal end 2612 may interface with a gear box 2004 or other arrangement that is driven by a motor 2006 or other source of rotary motion housed in the housing of the surgical instrument. See FIG. 2. Such source of rotary motion causes the proximal rotary drive shaft to rotate about the shaft axis SA within the axial passage 2126 in the proximal support shaft 2120.

Figure 16:
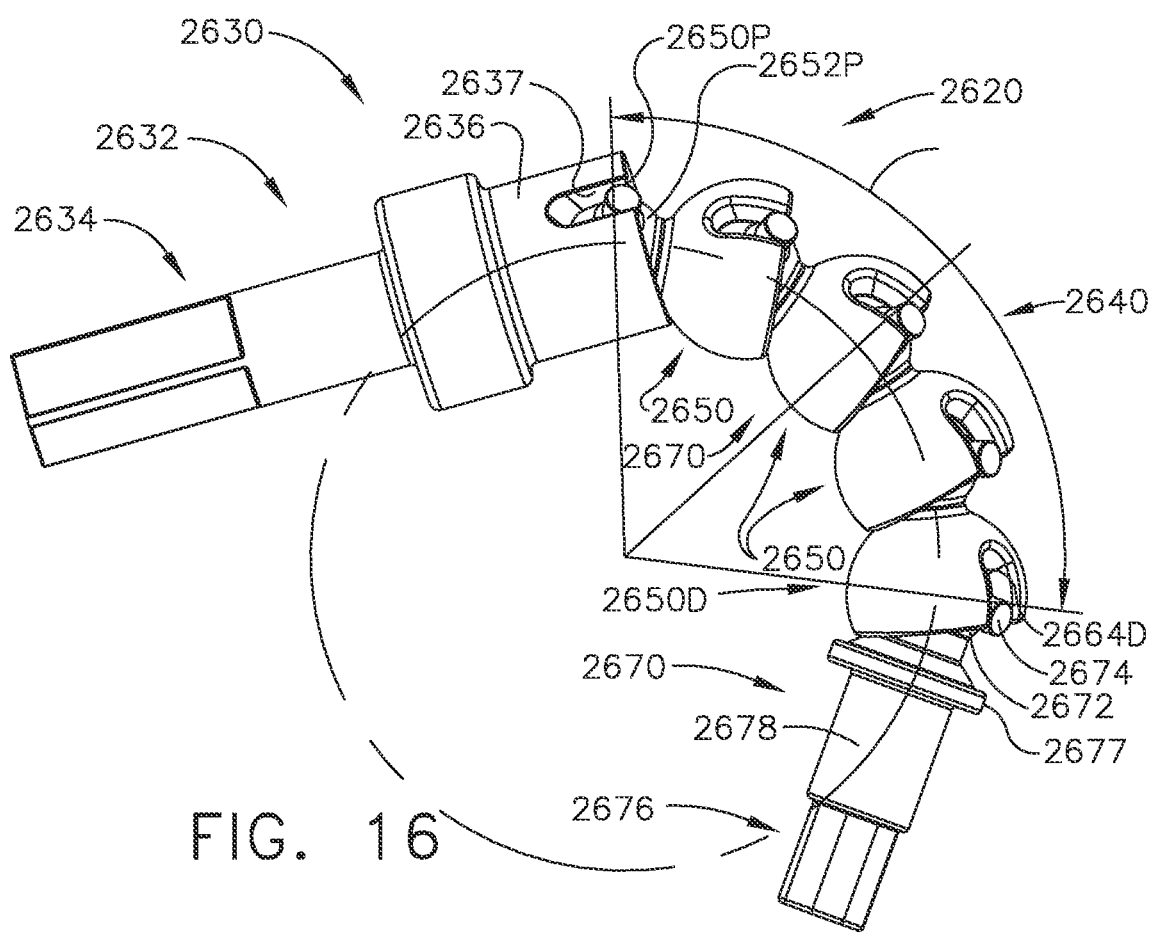
FIG. 16 is a perspective view of a CV drive shaft assembly of the rotary drive system of FIG. 8 in an articulated orientation.
Figure 17:
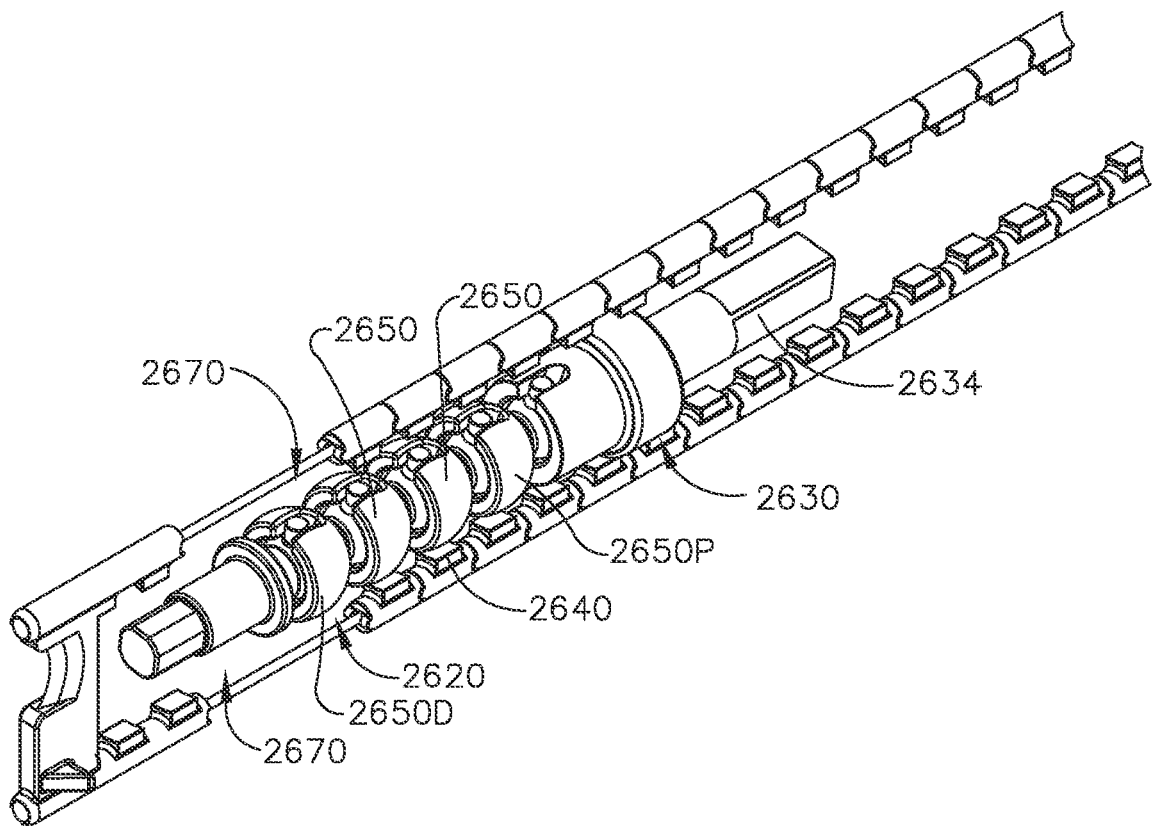
FIG. 17 is a perspective view of the firing system of FIG. 8 in driving engagement with the CV drive shaft assembly of FIG. 16 in accordance with at least one aspect of the present disclosure.

The proximal rotary drive shaft 2610 is operably supported within the elongate shaft assembly 2000 in a location that is proximal to the articulation joint 2200 and operably interfaces with a constant velocity (CV) drive shaft assembly 2620 that spans or extends axially through the articulation joint 2200. As can be seen in FIGS. 8, 16, and 17, in at least one arrangement, the CV drive shaft assembly 2620 comprises a proximal CV drive assembly 2630 and a distal CV drive shaft 2670. The proximal CV drive assembly 2630 comprises a proximal shaft segment 2632 that consists of an attachment shaft 2634 that is configured to be non-rotatably received within a similarly-shaped coupler cavity 2616 in the distal end 2614 of the proximal rotary drive shaft 2610. The proximal shaft segment 2632 operably interfaces with a series 2640 of movably coupled drive joints 2650.

Figure 18:
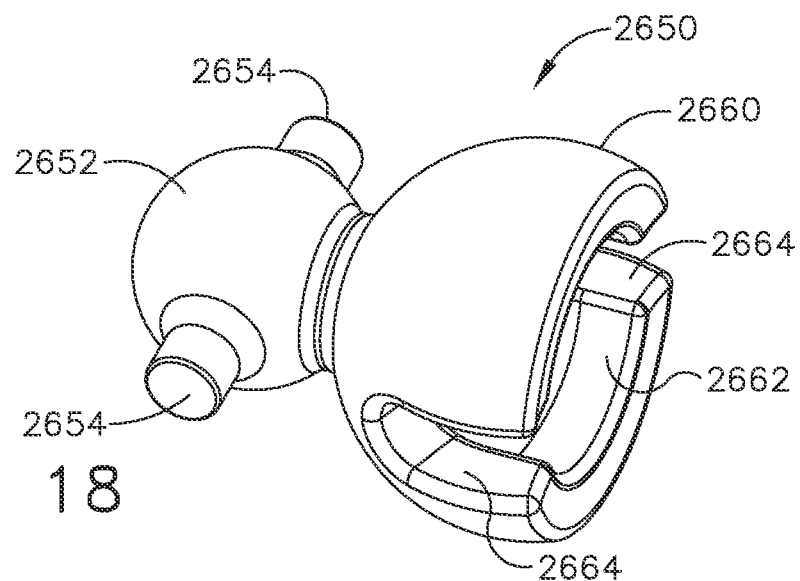
FIG. 18 is a perspective view of a drive joint of the CV drive shaft assembly of FIG. 16.

As can be seen in FIG. 18, in at least one arrangement, each drive joint 2650 comprises a first or distal sphere portion 2660 and a second or proximal sphere portion 2652. The distal sphere portion 2660 is larger than the proximal sphere portion 2652. The distal sphere portion 2660 comprises a socket cavity 2662 that is configured to rotatably receive a proximal sphere portion 2652 of an adjacent drive joint 2650 therein. Each proximal sphere portion 2652 comprises a pair of diametrically opposed joint pins 2654 that are configured to be movably received in corresponding pin slots 2664 in the distal sphere portion 2660 of an adjacent drive joint 2650 as can be seen in FIG. 16. A proximal sphere portion 2652P of a proximal-most drive joint 2650P is rotatably received in a distal socket portion 2636 of the proximal shaft segment 2632 as shown in FIG. 16. The joint pins 2654P are received within corresponding pin slots 2637 in the distal socket portion 2636. As can be further seen in FIG. 16, a distal-most drive joint 2650D in the series 2640 of movably coupled drive joints 2650 is movably coupled to a distal CV drive shaft 2670.

In at least one arrangement, the distal CV drive shaft 2670 comprises a proximal sphere portion 2672 that is sized to be movably received in the socket cavity 2662D in the distal-most drive joint 2650D. The proximal sphere portion 2672 includes joint pins 2674 that are movably received in the pin slots 2664D in the distal-most drive joint 2650D. The distal CV drive shaft 2670 further comprises a distally extending shaft stem 2676 that is configured to be non-rotatably coupled to the rotary drive screw 2700 that is positioned distal to the articulation joint 2200. The distal CV drive shaft 2670 includes a flange 2677 and a mounting barrel portion 2678 for receiving a thrust bearing housing 2680 thereon.

In the illustrated arrangement, when the series 2640 of movably coupled drive joints 2650 articulates, the joint pins 2674 remain in the corresponding pin slots 2664 of an adjacent drive joint 2650. In the example illustrated in FIG. 18, each drive joint may be capable of approximately eighteen degrees of articulation in the pitch and yaw directions. FIG. 16 illustrates an angle of the series of 2640 of drive joints 2650 when each drive joint 2650 in the series are fully articulated ninety degrees in pitch and yaw which yields an angle α of approximately 100.9 degrees. In such arrangement, the outer surface of each distal sphere portion 2660 clears the outer surface of the adjacent or adjoining proximal sphere portion 2652 allowing for unrestricted motion until the eighteen degree limit is reached. The rigid design and limited small angles allow the series 2640 of movably coupled drive joints 2650 to carry high loads torsionally at an overall large angle.

In the illustrated arrangement, the articulation joint 2200 comprises an articulation joint spring 2230 that is supported within an outer elastomeric joint assembly 2210. The outer elastomeric joint assembly 2210 comprises a distal end 2212 that is attached to the proximal end 1112 of the elongate channel 1110. For example, as can be seen in FIG. 6, the distal end 2212 of the outer elastomeric joint assembly 2210 is attached to the proximal end 1112 of the elongate channel 1110 by a pair of cap screws 2722 that extend through a distal mounting bushing 2720 to be threadably received in the proximal end 1112 of the elongate channel 1110. A proximal end 2214 of the elastomeric joint assembly 2210 is attached to the distal end 2124 of the proximal support shaft 2120. The proximal end 2214 of the elastomeric joint assembly 2210 is attached to the distal end 2124 of the proximal support member 2120 by a pair of cap screws 2732 that extend through a proximal mounting bushing 2750 to be threadably received in threaded inserts 2125 mounted within the distal end 2124 of the proximal support shaft 2120.

To prevent the drive joints 2650 from buckling during articulation, the series 2640 of movably coupled drive joints 2650 extend through at least one low friction articulation joint spring 2730 that is supported within the outer elastomeric joint assembly 2210. See FIG. 19. The articulation joint spring 2730 is sized relative to the drive joints 2650 such that a slight radial clearance is provided between the articulation joint spring 2730 and the drive joints 2650. The articulation joint spring 2730 is designed to carry articulation loads axially which may be significantly lower than the torsional firing loads. The joint spring(s) is longer than the series 2640 of drive joints 2650 such that the drive joints are axially loose. If the "hard stack" of the series 2640 of drive joints 2650 is longer than the articulation joint spring(s) 2730 hard stack, then the drive joints 2650 may serve as an articulation compression limiter causing firing loads and articulation loads to resolve axially through the series 2640 of the drive joints 2650. When the firing loads resolve axially through the series 2640 of the drive joints 2650, the loads may try to straighten the articulation joint 2200 or in other words cause de-articulation. If the hard stack of the articulation joint spring(s) 2730 is longer than the hard stack of the series 2640 of the drive joints 2650, the firing loads will then be contained within the end effector and no firing loads will resolve through the drive joints 2650 or through the springs(s) 2730.

Figure 19:
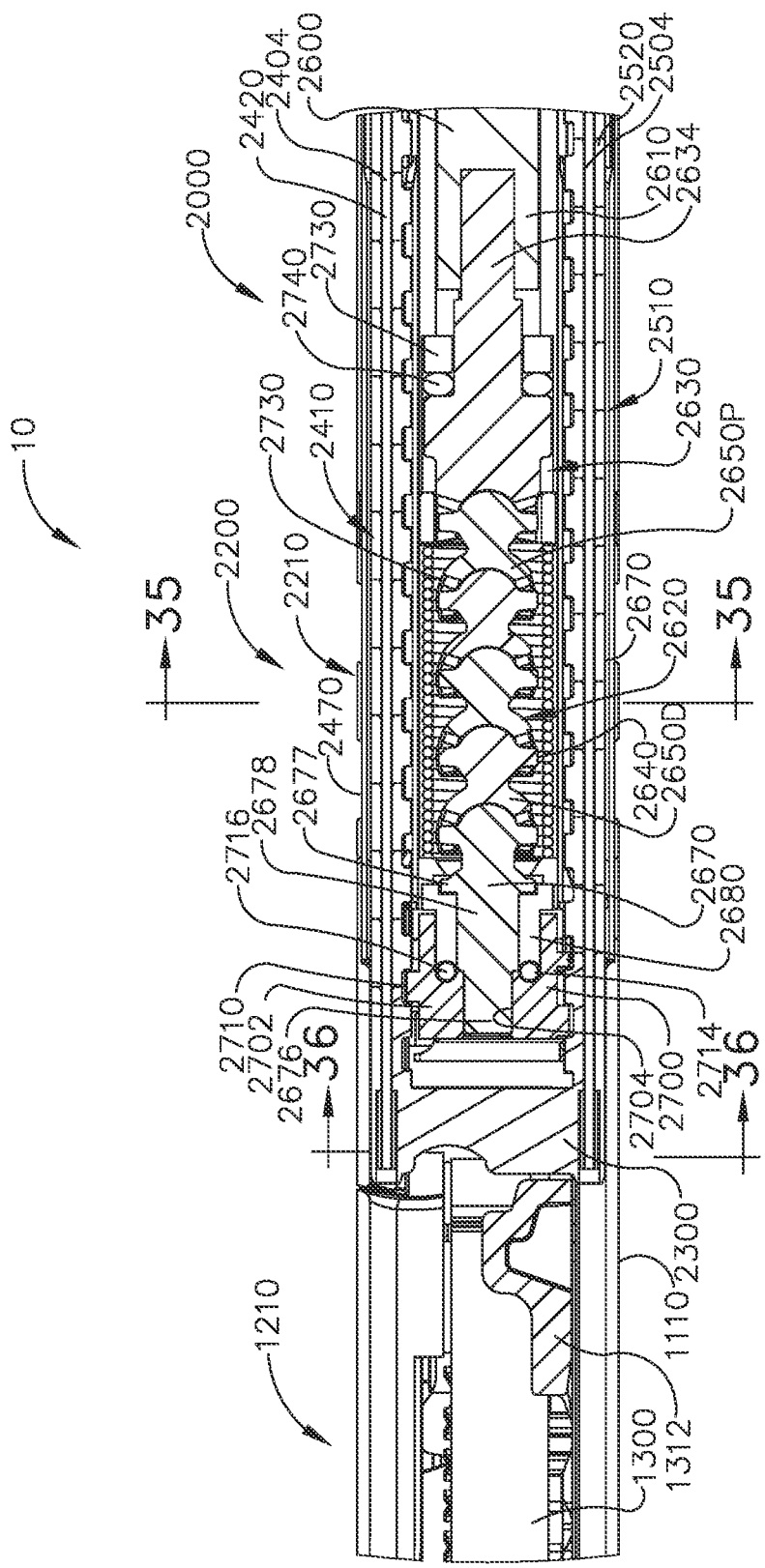
FIG. 19 is a cross-sectional view of a portion of the surgical instrument of FIG. 4 taken along line 19-19 in FIG. 4.
Figure 20:
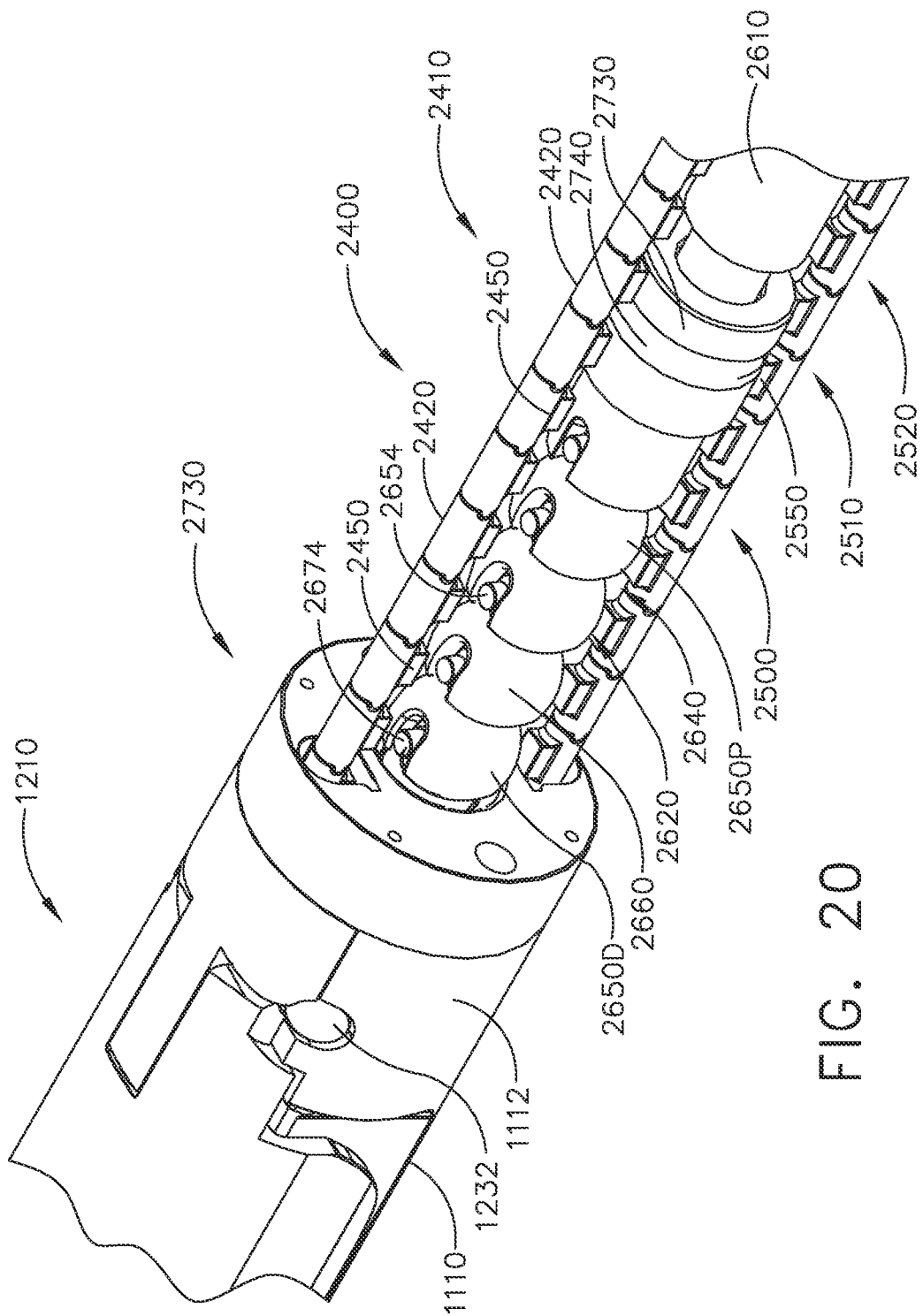
FIG. 20 is a partial perspective view of a proximal end portion of the surgical end effector and portions of the firing system and the rotary drive system of the surgical instrument of FIG. 1.
Figure 21:
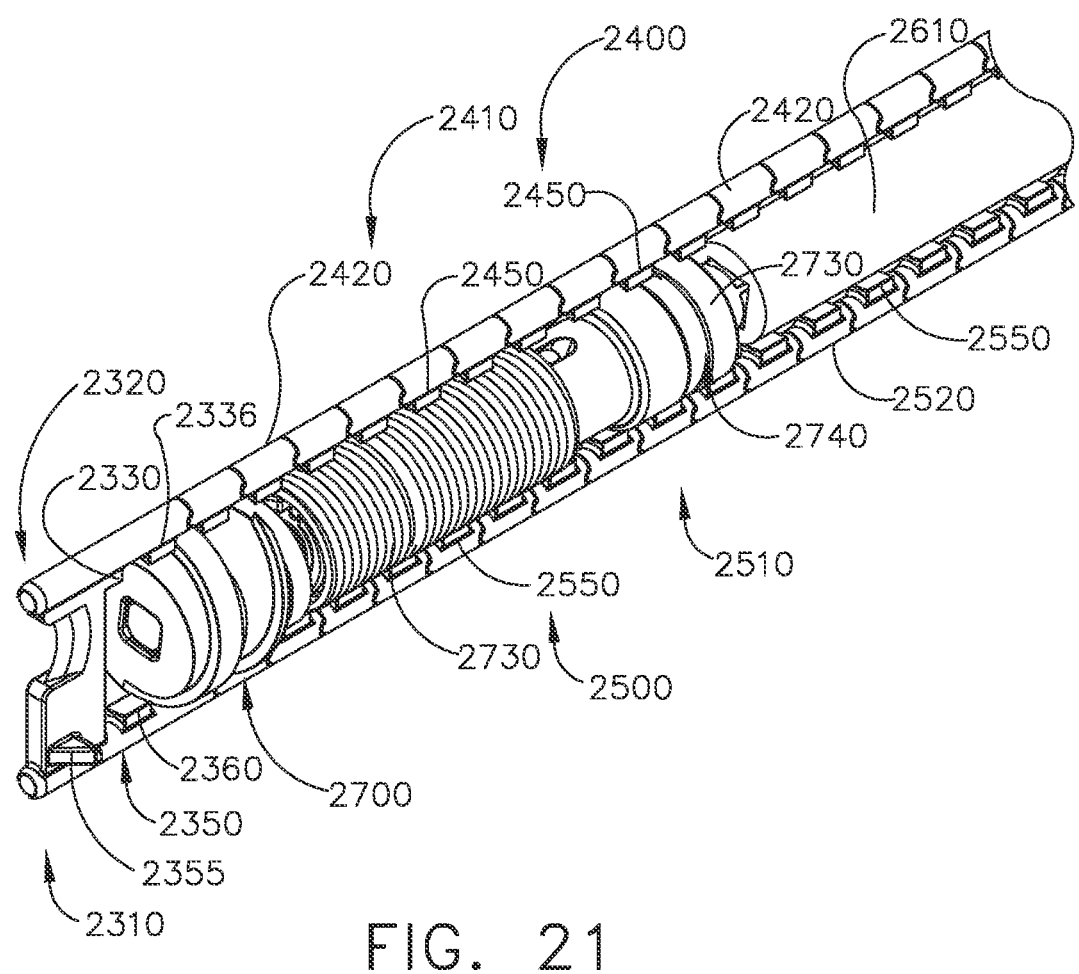
FIG. 21 is a perspective view of the rotary drive system of the surgical instrument of FIG. 1 in driving engagement with the firing system thereof in accordance with at least one aspect of the present disclosure.

To further ensure that the drive joints 2650 are always engaged with each other, a proximal drive spring 2740 is employed to apply an axial biasing force to the series 2640 of drive joints 2650. For example, as can be seen in FIGS. 8, 19, and 20, the proximal drive spring 2740 is positioned between the proximal mounting bushing 2734 and a support flange that is formed between the distal socket portion 2636 and a proximal barrel portion 2638 of the proximal shaft segment 2632. In one arrangement, the proximal drive spring 2740 may comprise an elastomeric O-ring/bushing received on the proximal barrel portion 2638 of the proximal shaft segment 2632. The proximal drive spring 2740 lightly biases the drive joints 2650 together to decrease any gaps that may occur during articulation. This ensures that the drive joints 2650 transfer loads torsionally. It will be appreciated, however, that in at least one arrangement, the proximal drive spring 2740 does not apply a high enough axial load to cause firing loads to translate through the articulation joint 2200.

As can be seen in FIGS. 9 and 10, the top firing member feature 2320 on the firing member 2310 comprises a distal upper firing member tooth segment 2330 that is equivalent to one half of an upper tooth 2450 on each upper vertebra member 2420. In addition, a proximal upper firing member tooth 2336 that is identical to an upper tooth 2450 on each upper vertebra member 2420 is spaced from the distal upper firing member tooth segment 2330. The distal upper firing member tooth segment 2330 and the proximal upper firing member tooth 2336 may be integrally formed with the top firing member feature 2320 of the firing member 2310. Likewise, the bottom firing member feature 2350 of the firing member 2310 comprises a distal lower firing member tooth 2360 and a proximal lower firing member tooth 2366 that are integrally formed on the bottom firing member feature 2350. For example, in at least one arrangement, the firing member 2310 with the rigidly attached teeth 2330, 2336, 2360, and 2366 may be fabricated at one time as one unitary component using conventional metal injection molding techniques.

As indicated above, each of the upper vertebra members 2520 is movably received on an upper flexible coupler member 2402 in the form of a top cable 2404. As was described above, the distal end 2406 of the top cable 2404 is secured to the top firing member feature 2320 of the firing member 2310. Similarly, each of the lower vertebra members 2520 is movably received on a lower flexible coupler member 2502 in the form of a lower cable 2504. A distal end 2506 of the lower cable 2504 is secured to the bottom firing member feature 2350 of the firing member 2310. In at least one arrangement, the top cable 2404 and the bottom cable 2504 extend through the proximal shaft portion 2100 and, as will be discussed in further detail below, may interface with a bailout arrangement supported in the housing for retracting the firing member 2310 back to its home or starting position should the firing member drive system fail.

Turning again to FIG. 8, the axial length $AL_u$ of the upper series 2410 of upper vertebra members 2420 and the axial length $AL_l$ of the lower series 2510 of lower vertebra members 2520 are equal and must be sufficiently long enough to facilitate the complete distal advancement of the firing member 2310 from the home or starting position to a distal-most ending position within the staple cartridge while the proximal-most upper vertebra members 2420 in the upper series 2410 of upper vertebra members 2420 and the proximal-most lower vertebra members 2520 in the lower series 2510 of lower vertebra members 2520 remain in driving engagement with the rotary drive screw 2700. As can be seen in FIG. 8, an upper compression limiting spring 2421 is configured to interface with a proximal-most upper vertebra member 2420P in the upper series 2410 of upper vertebra members 2420. The upper compression limiting spring 2421 is journaled on the top cable 2404 and is retained in biasing engagement with the proximal-most upper vertebra member 2420P by an upper spring holder 2423 that is retained in position by an upper ferrule 2425 that is crimped onto the top cable 2404. The top cable 2404 extends through an upper hypotube 2433 that is supported in the proximal support shaft. Likewise, a lower compression limiting spring 2521 is configured to interface with a proximal-most, lower vertebra member 2520P in the lower series 2510 of lower vertebra members 2520. The lower compression spring 2521 is journaled on the lower cable 2504 and is retained in biasing engagement with the proximal-most, lower vertebra member 2520P by a lower spring holder 2523 that is retained in position by a lower ferrule 2525 that is crimped onto the lower cable 2504. The lower cable 2504 extends through a lower hypotube 2533 that is supported in the proximal support shaft.

When the upper vertebra members 2420 and the lower vertebra members 2520 angle through the articulation joint (after the end effector has been positioned in an articulated position), the gaps between the respective vertebra members 2420, 2520 increase in each series 2410, 2510 which causes the springs 2421, 2521 to become tighter. The compression limiting springs 2421, 2521 provide enough slack in the cables 2404, 2504, respectively to enable the vertebra members 2420, 2520 angle through the most extreme articulation angles. If the cables 2404, 2504 are pulled too tight, the spring holders 2423, 2523 will contact their respective proximal-most vertebra members 2420P, 2520P. Such compression limiting arrangements ensure that the vertebra members 2420, 2520 in their respective series 2410, 2510 always remain close enough together so that the rotary drive screw 2700 will always drivingly engage them in the manner discussed in further detail below. When the vertebra members 2420, 2520 are aligned straight again, the compression limiting springs 2421, 2521 may partially relax while still maintaining some compression between the vertebra members.

As indicated above, when the upper vertebra members 2420 are arranged in the upper series 2410 and lower vertebra members 2520 are arranged in the lower series 2510, the convex mounds and concave recesses in each vertebra member as well as the compression limiter springs serve to maintain the upper and lower vertebra members in relatively linear alignment for driving engagement by the rotary drive screw 2700. As can be seen in FIGS. 9 and 10, when the upper vertebra members 2420 are in linear alignment, the upper teeth 2450 are spaced from each other by an opening space generally designated as 2460 that facilitates driving engagement with the helical drive thread 2170 on the rotary drive screw. Similarly, when the lower vertebra members 2520 are in linear alignment, the lower vertebra member teeth 2550 are spaced from each other by an opening space generally designated as 2560 that facilitates driving engagement with the helical drive thread 2170 of the rotary drive screw 2700.

Figure 22:
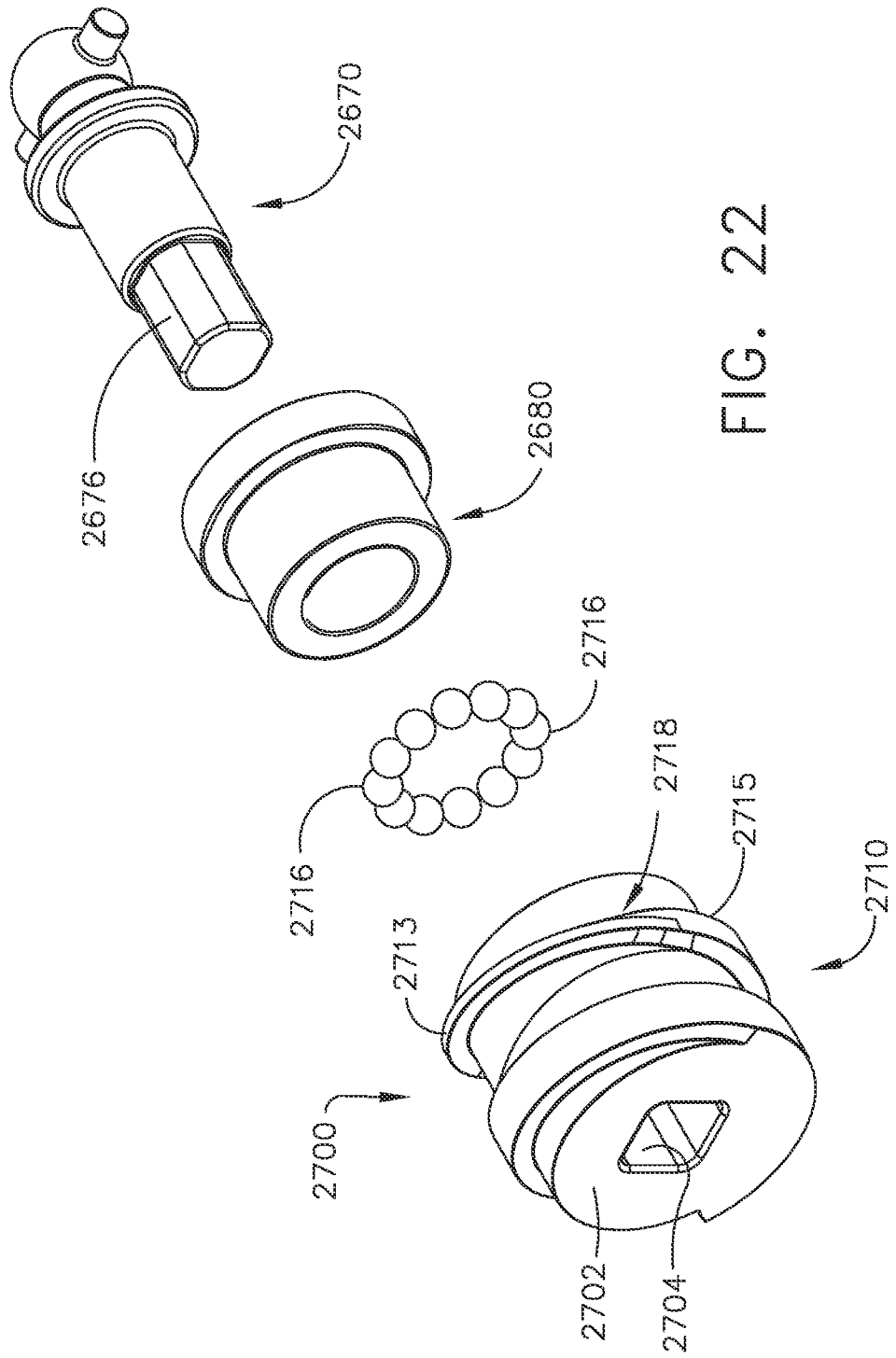
FIG. 22 is an exploded perspective view of the rotary drive screw and thrust bearing arrangement of the firing system of FIG. 21.

Turning to FIGS. 8 and 22, the rotary drive screw 2700 comprises a screw body 2702 that has a socket 2704 therein for receiving the distally extending shaft stem 2676 of the distal CV drive shaft 2670. An internal radial groove 2714 (FIG. 10) is formed in the screw body 2702 for supporting a plurality of ball bearings 2716 therein. In one arrangement, for example, 12 ball bearings 2716 are employed. The radial groove 2714 supports the ball bearings 2716 between the screw body 2702 and a distal end of the thrust bearing housing 2680. The ball bearings 2716 serve to distribute the axial load of the rotary drive screw 2700 and significantly reduce friction through the balls' rolling motion.

As can be seen in FIG. 23, a helical drive thread 2710 is provided around the screw body 2702 and serves to form a proximal thread scoop feature 2712. The proximal thread scoop feature 2712 is formed with a first pitch 2713 and the remaining portion of the helical drive thread 2710 is formed with a second pitch 2715 that differs from the first pitch 2713. In FIGS. 22 and 23, area 2718 illustrates where the first pitch 2713 and the second pitch 2715 converge. In at least one embodiment, the first pitch 2713 is larger than the second pitch 2715 to ensure that the rotary drive screw 2700 captures and "scoops up" or drivingly engages every upper vertebra member 2420 and every lower vertebra member 2520. As can be seen in FIG. 24, a proximal end 2717 of the helical drive thread 2710 that has the first pitch 2713 has scooped into the into the opening space 2560 between two adjacent lower vertebra member teeth 2550A and 2550B while the center portion 2719 of the helical drive thread 2710 that has the second pitch 2715 is in driving engagement with the helix-shaped distal lower face portion 2554 on the lower vertebra member tooth 2550B and the helix-shaped proximal lower face portion 2552 on the proximal lower firing member tooth 2366. As can also be appreciated, the scoop feature 2712 may not contact the helix-shaped distal lower face portion 2554A of the lower vertebra member tooth 2550A as it scoops up the lower vertebra member tooth 2550B when driving the firing member 2310 distally. The helical drive thread 2710 interacts with the teeth 2450 of the upper vertebra members 2420 in a similar manner.

A power screw is a threaded rod with a full three hundred sixty degree nut around it. Rotation of the power screw causes the nut to advance or move longitudinally. In the present arrangements, however, due to space constraints, a full three hundred sixty degree nut cannot fit inside the end effector. In a general sense, the upper flexible spine assembly 2400 and the lower flexible spine assembly 2500 comprise a radially/longitudinally segmented "power screw nut" that is rotatably driven by the rotary drive screw 2700. When the rotary drive screw is rotated in a first rotary direction, the rotary drive screw 2700 drives one or more vertebra members in each of the upper series and lower series of vertebra members longitudinally while the vertebra members 2420, 2520 stay in the same locations radially. The upper series 2410 and lower series 2510 are constrained from rotating around the rotary drive screw 2700 and can only move longitudinally. In one arrangement, the upper vertebra members 2420 in the upper series 2410 and the lower vertebra members 2520 in the lower series 2510 only surround the rotary drive screw 2700 with less than ten degrees each.

Figure 25:
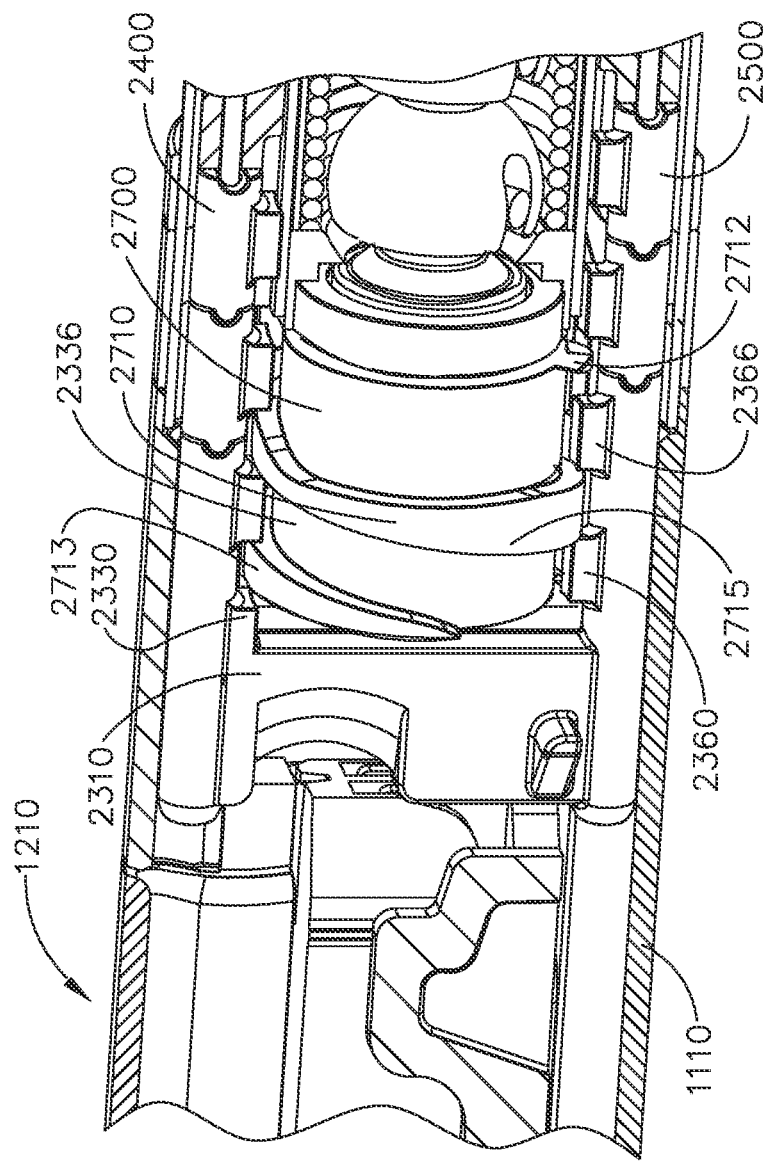
FIG. 25 is a perspective view of the firing member in a home or starting position within the surgical end effector of the surgical instrument of FIG. 1.
Figure 26:
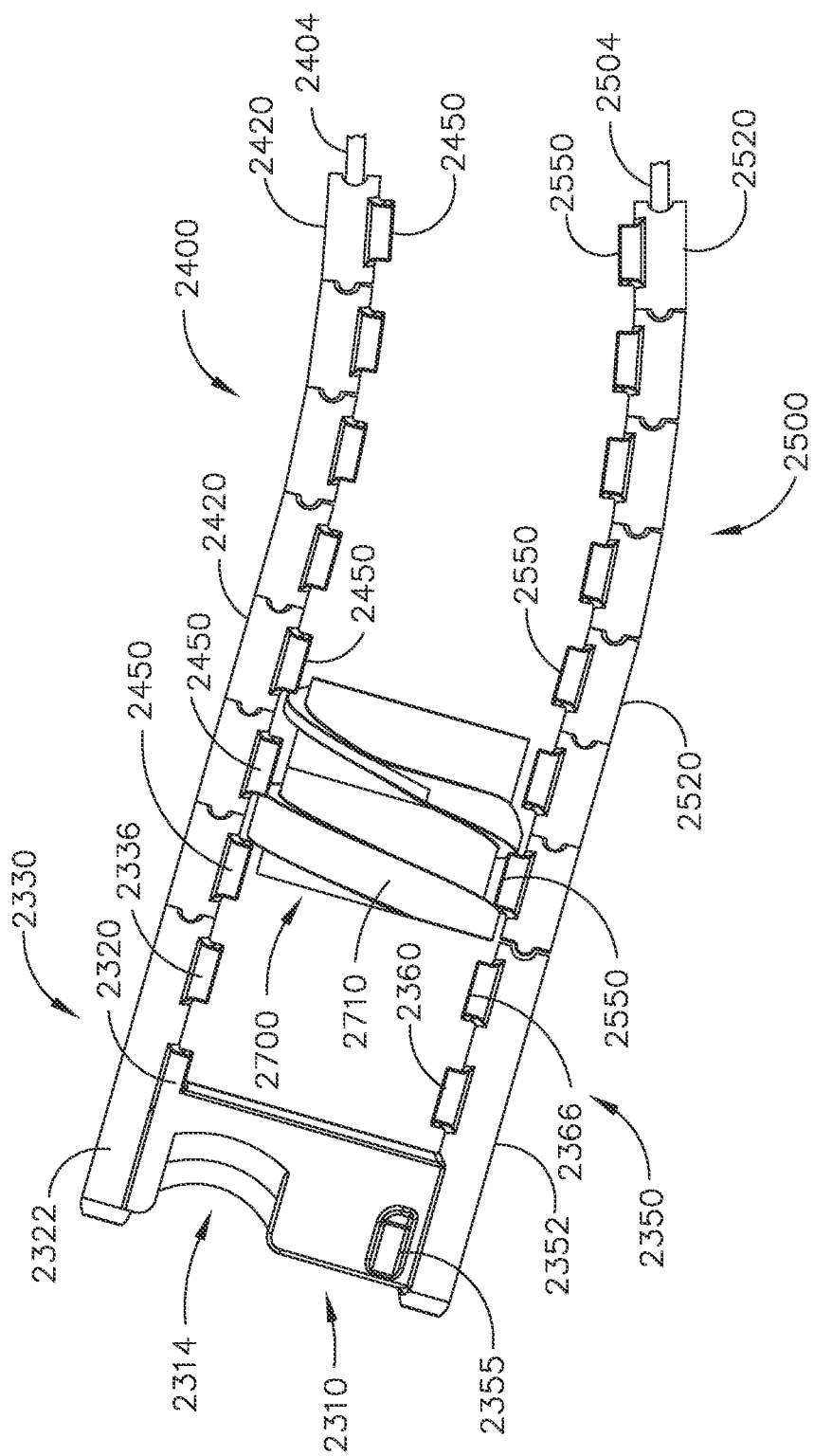
FIG. 26 is a side view illustrating the upper flexible spine assembly and the lower flexible spine assembly of FIG. 21 in driving engagement with the rotary drive screw after the firing member has been driven distally from a home or starting position.

FIG. 25 illustrates the firing member 2310 in the home or starting position. As can be seen in FIG. 25, a portion of the helical drive thread 2710 on the rotary drive screw 2700 is engaged between the distal upper firing member tooth segment 2330 and the proximal upper firing member tooth 2336 and another portion of the helical drive thread 2710 is engaged between the distal lower firing member tooth 2360 and a proximal lower firing member tooth 2366 on the firing member 2310. Such arrangement enables the rotary drive screw 2700 to precisely control the distal and proximal movement of the firing member 2310 which, as will be discussed in further detail below, can result in the precise movement of the anvil 1210. Once the firing member 2310 has been sufficiently distally advanced during a firing stroke, the helical drive thread 2710 operably engages the teeth on the upper and lower vertebras. See FIG. 26.

Figure 27:
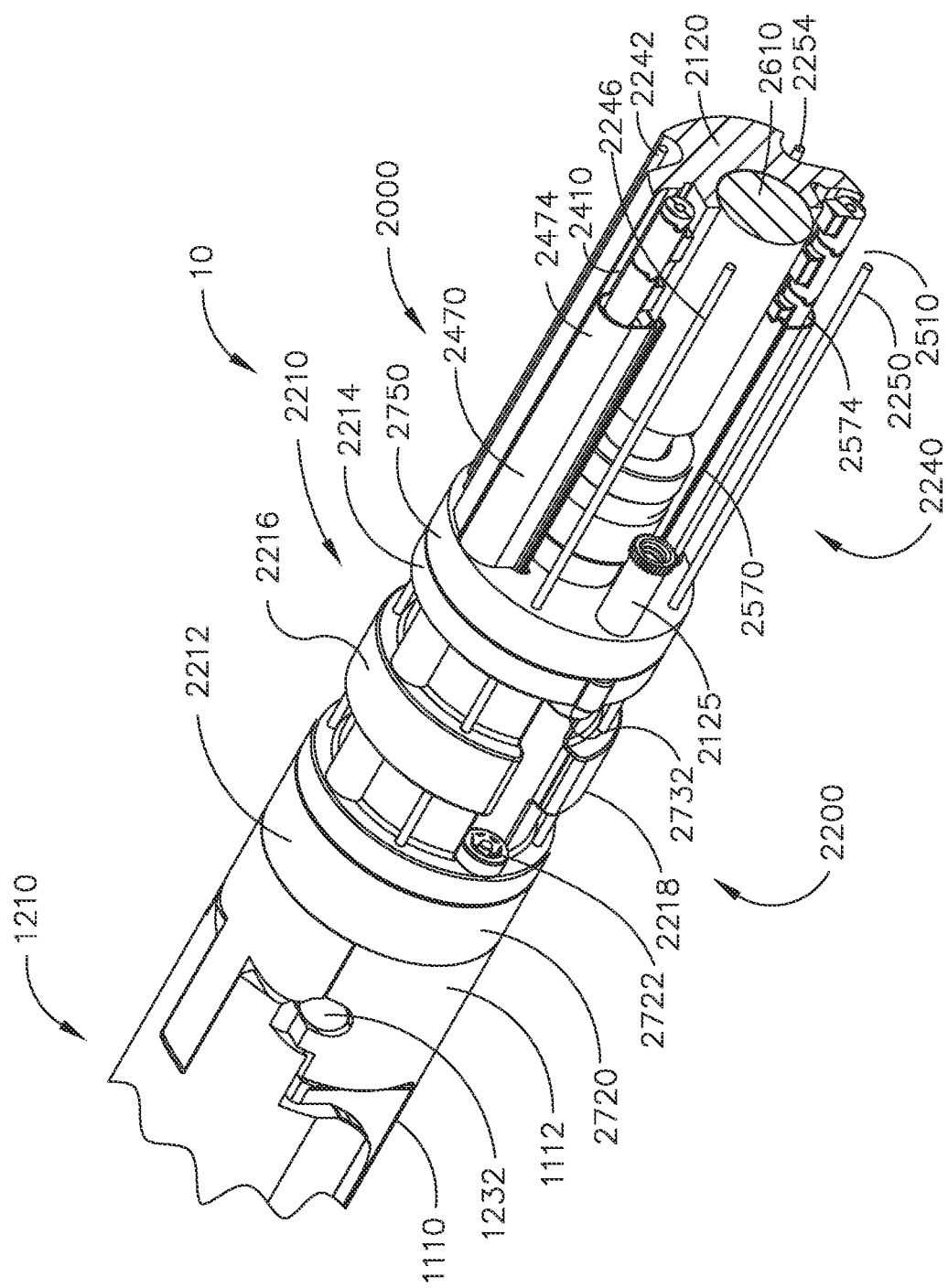
FIG. 27 is a partial cross-sectional perspective view of a portion of the surgical end effector, firing system and rotary drive system of the surgical instrument of FIG. 1 according to at least one aspect of the present disclosure with an outer elastomeric joint assembly of an articulation joint omitted for clarity.
Figure 29:
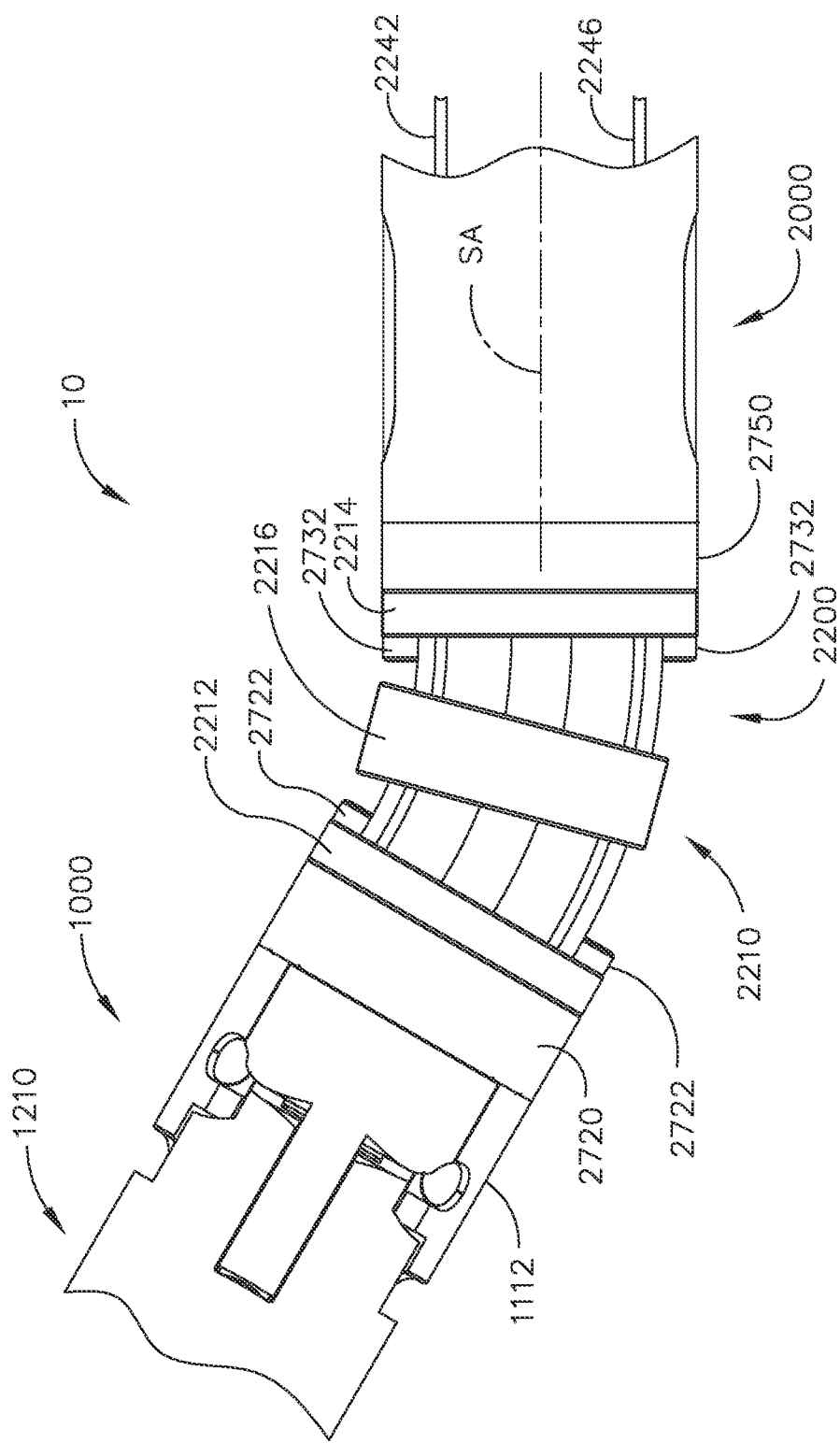
FIG. 29 is a top view of the surgical end effector of FIG. 27 articulated in a first direction relative to a portion of the elongate shaft assembly in accordance with at least one aspect of the present disclosure.
Figure 30:
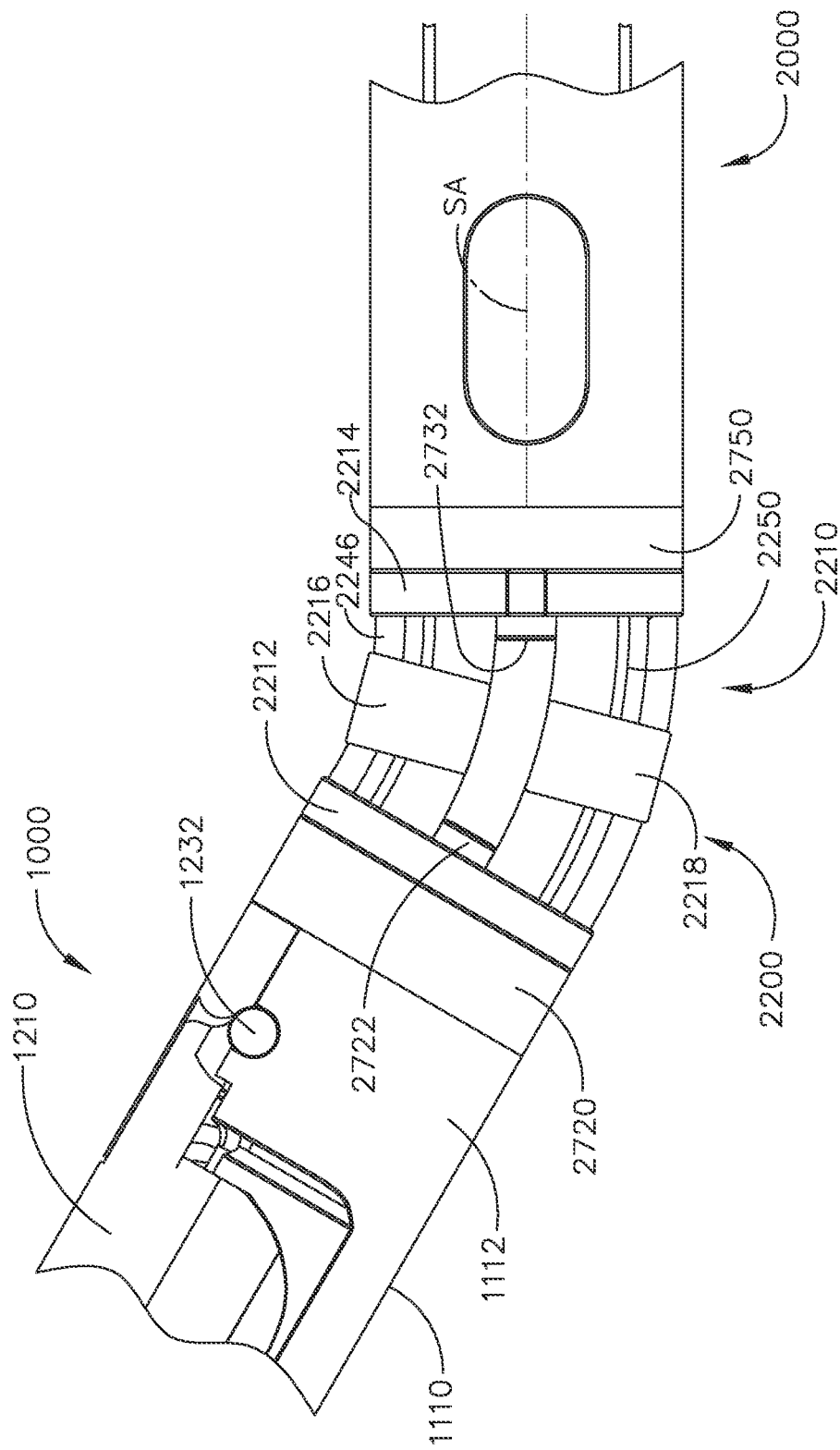
FIG. 30 is a side view of the surgical end effector of FIG. 29 articulated in another direction relative to a portion of the elongate shaft assembly in accordance with at least one aspect of the present disclosure.
Figure 31:
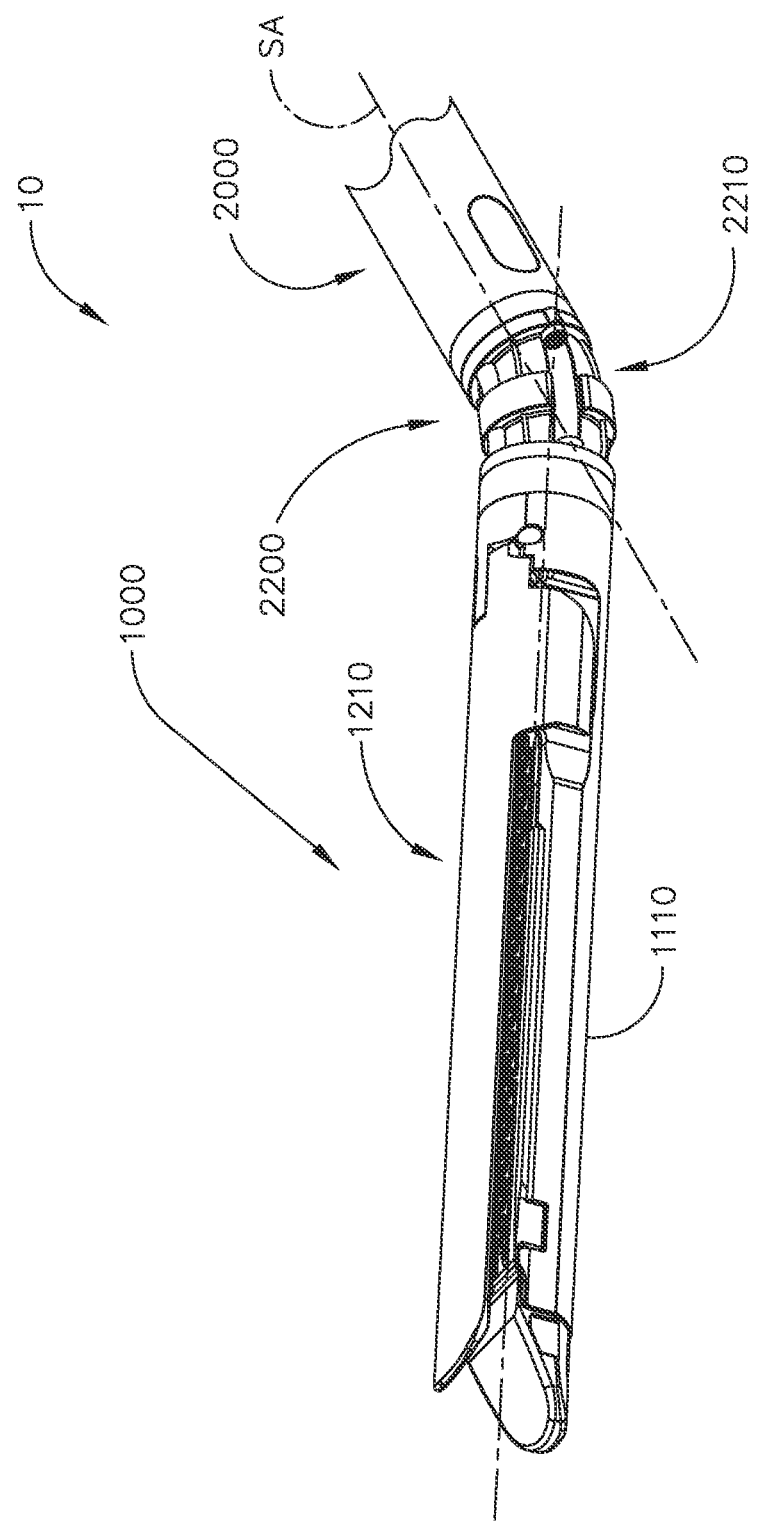
FIG. 31 is a perspective view of the surgical end effector of FIG. 29 articulated in multiple planes with respect to a portion of the elongate shaft assembly in accordance with at least one aspect of the present disclosure.

The surgical instrument 10 also comprises an articulation system 2240 that is configured to apply articulation motions to the surgical end effector 1000 to articulate the surgical end effector relative to the elongate shaft assembly 2000. In at least one arrangement, for example, the articulation system comprises four articulation cables 2242, 2246, 2250, and 2254 that extend through the elongate shaft assembly 2000. See FIG. 27. In the illustrated arrangement, the articulation cables 2242, 2246 pass through the proximal mounting bushing 2750, the proximal end 2214 of the elastomeric joint assembly 2210, as well as a central rib segment 2216 to be secured to the distal end 2212 of the elastomeric joint assembly 2210 or other portion of the surgical instrument. Likewise, the articulation cables 2250 and 2254 extend through the proximal mounting bushing 2750, the proximal end 2214 of the elastomeric joint assembly 2210, as well as a central rib segment 2218 to be secured to the distal end 2212 of the elastomeric joint assembly 2210 or other portion of the surgical end effector. The cables 2242, 2246, 2250, and 2254 operably interface with an articulation control system that is supported in the housing of the surgical instrument 10. For example, a proximal portion of each cable 2242, 2246, 2250, and 2254 may be spooled on a corresponding rotary spool or cable-management system 2007 (FIG. 2) in the housing portion of the surgical instrument 10 that is configured to payout and retract each cable 2242, 2246, 2250, and 2254 in desired manners. The spools/cable management system may be motor powered or manually powered (ratchet arrangement, etc.). FIG. 29 illustrates articulation of the surgical end effector 1000 through a first articulation plane relative to the elongate shaft assembly 2000. FIG. 30 illustrates articulation of the surgical end effector 1000 through a second articulation plane relative to the elongate shaft assembly 2000. FIG. 31 illustrates articulation of the surgical end effector 1000 through multiple articulation planes relative to the elongate shaft assembly 2000.

Figure 32:
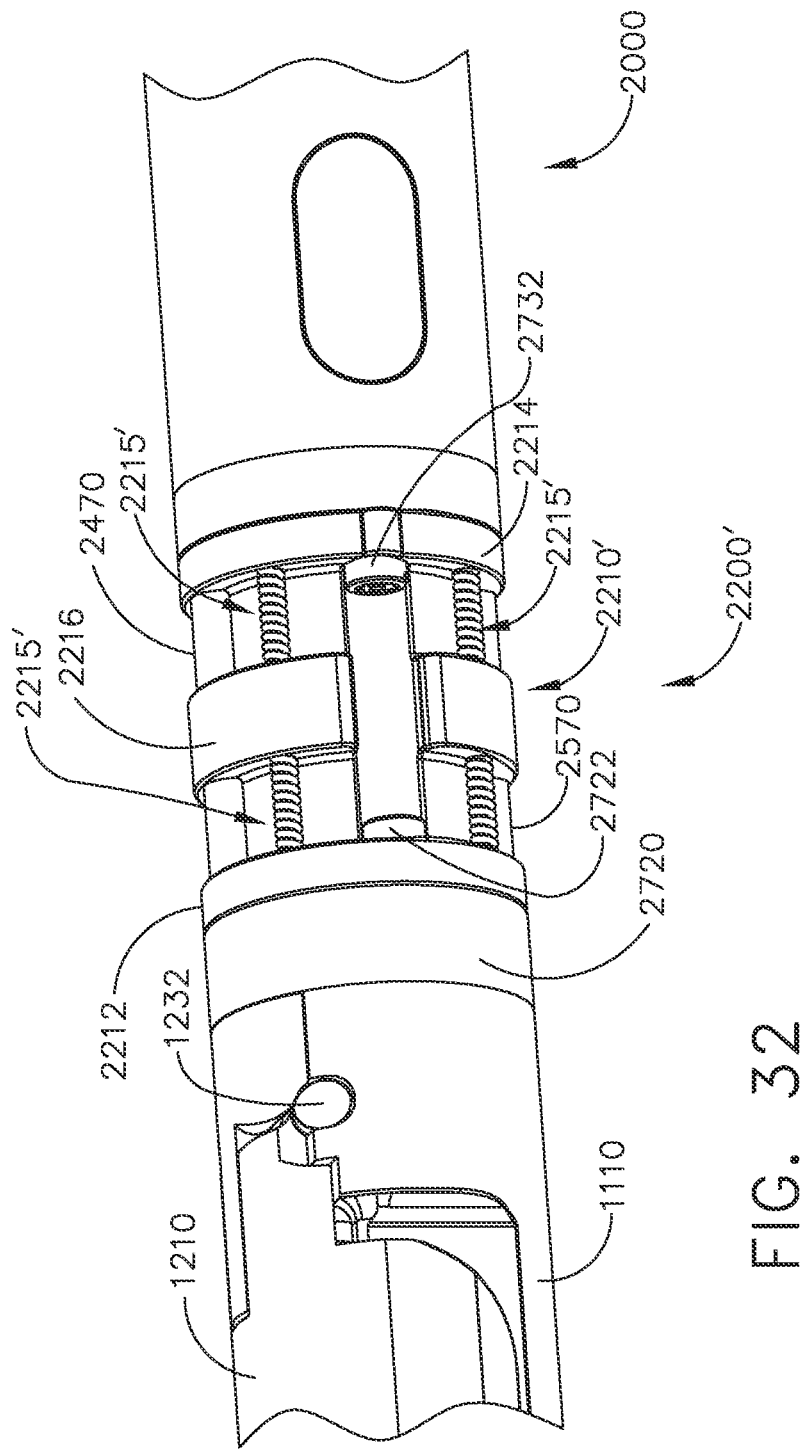
FIG. 32 is a side elevational view of a portion of another surgical instrument that employs another outer elastomeric joint assembly in accordance with at least one aspect of the present disclosure.
Figure 33:
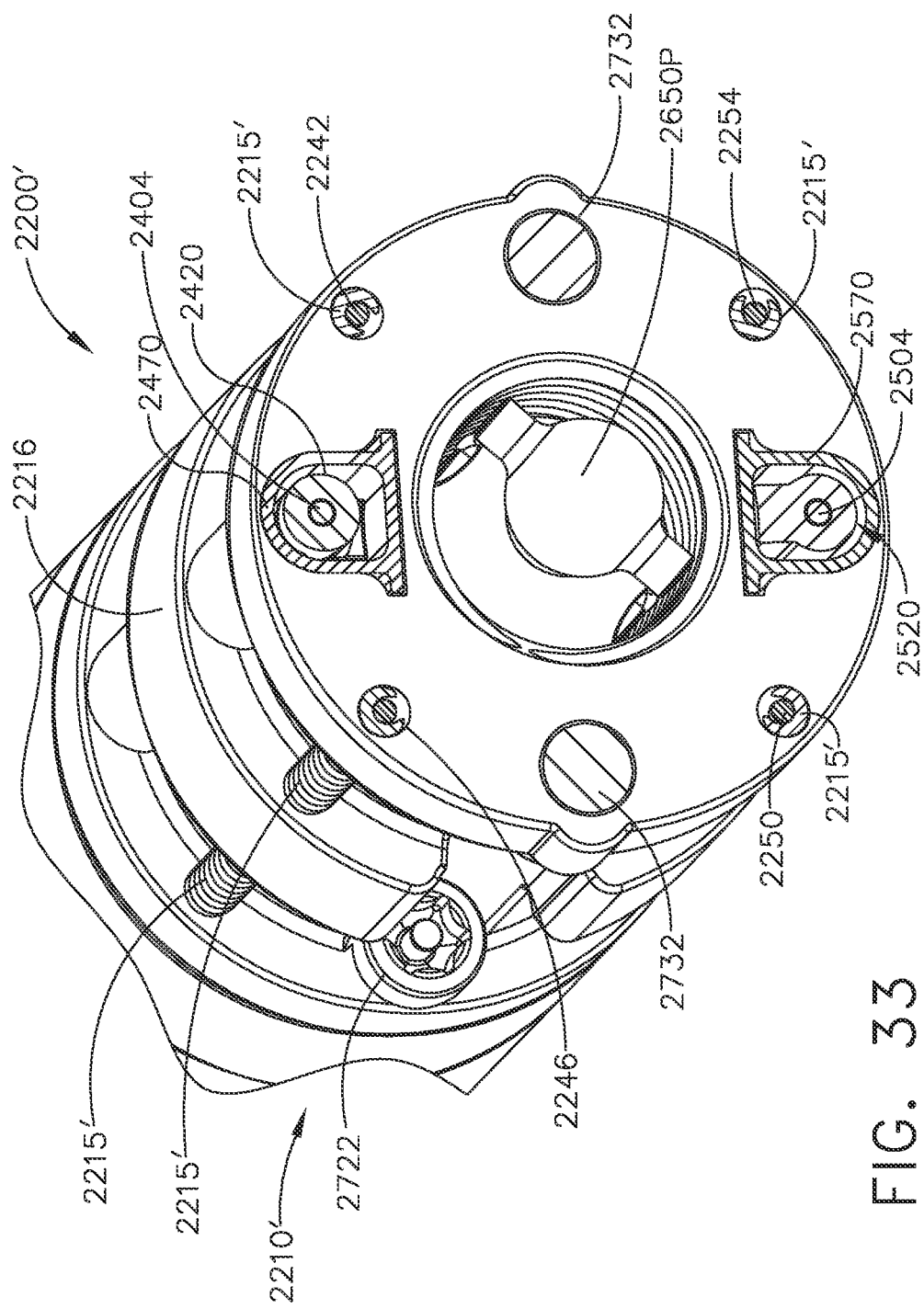
FIG. 33 is a partial cross-sectional perspective view of the surgical instrument of FIG. 32.
Figure 34:
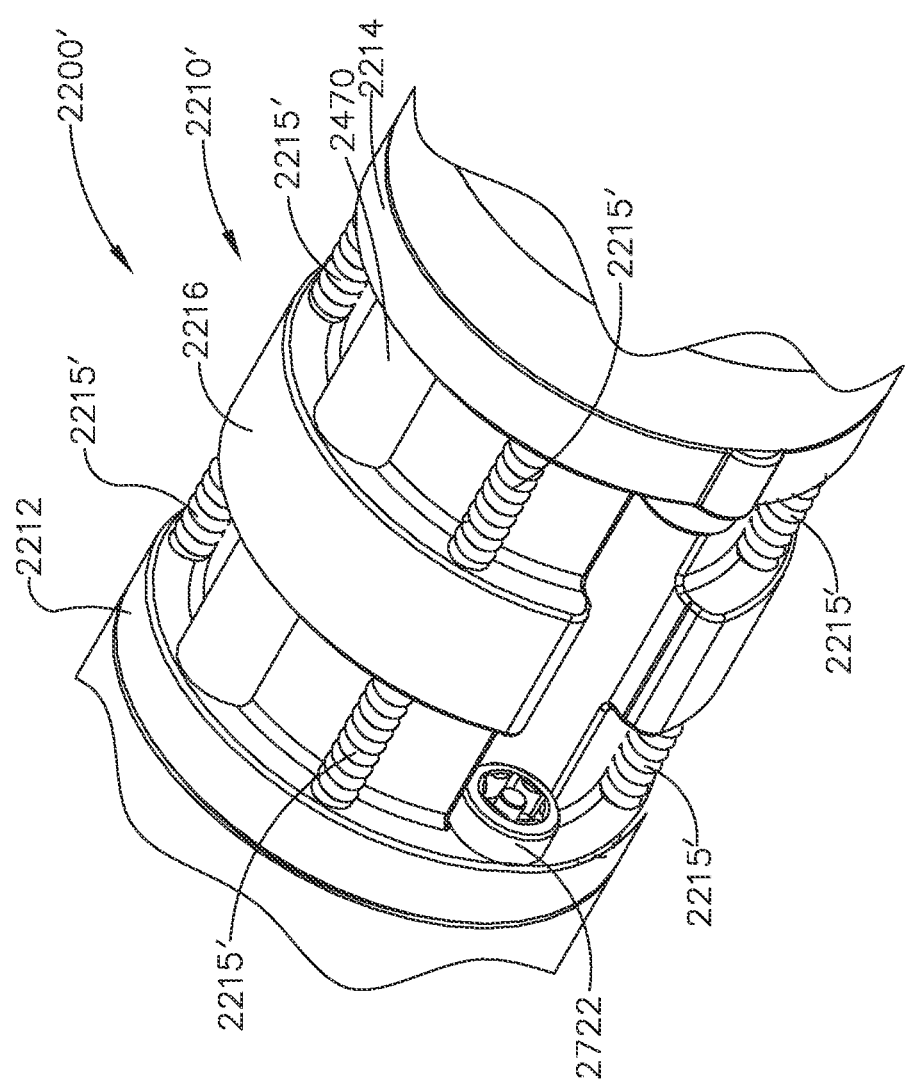
FIG. 34 is a perspective view of a portion of the outer elastomeric joint assembly of FIG. 32.

FIGS. 32-34 illustrate an alternative articulation joint 2200' in the form of an elastomeric joint assembly 2210'. As can be seen in FIG. 33, each articulation cable passes through a corresponding spring 2215' that is mounted in the ribs 2216' of the elastomeric joint assembly 2210'. For example, cable 2242 extends through spring 2244. Cable 2246 extends through spring 2248. Cable 2250 extends through spring 2252 and cable 2254 extends through spring 2256. As indicated above, the end effector is articulated by pulling on and relaxing the appropriate cables 2242, 2246, 2250 and 2254. To achieve higher articulation angles with greater joint stability, each of the springs 2244, 2248, 2252, and 2256 can slide through the ribs of the elastomeric joint to push the end effector and pull on the cables extending therethrough. The springs 2244, 2248, 2252, and 2256 will also retract into the ribs when the cables 2242, 2246, 2250, and 2254 are pulled tight. Each of the springs 2244, 2248, 2252, and 2256 loosely seat over the particular cable that passes therethrough. Each cable and corresponding spring may terminate or otherwise be coupled to a corresponding solid rod that is supported in the elongate shaft assembly 2000 and may be pushed and pulled from its proximal end. When the cable is pulled, the corresponding spring would carry little to no load. When the spring is pushed, the cable would carry little load, but will help limit the end effector movement. This interaction between the cable and spring may facilitate higher articulation angles that may approach ninety degrees, for example.

Figure 28:
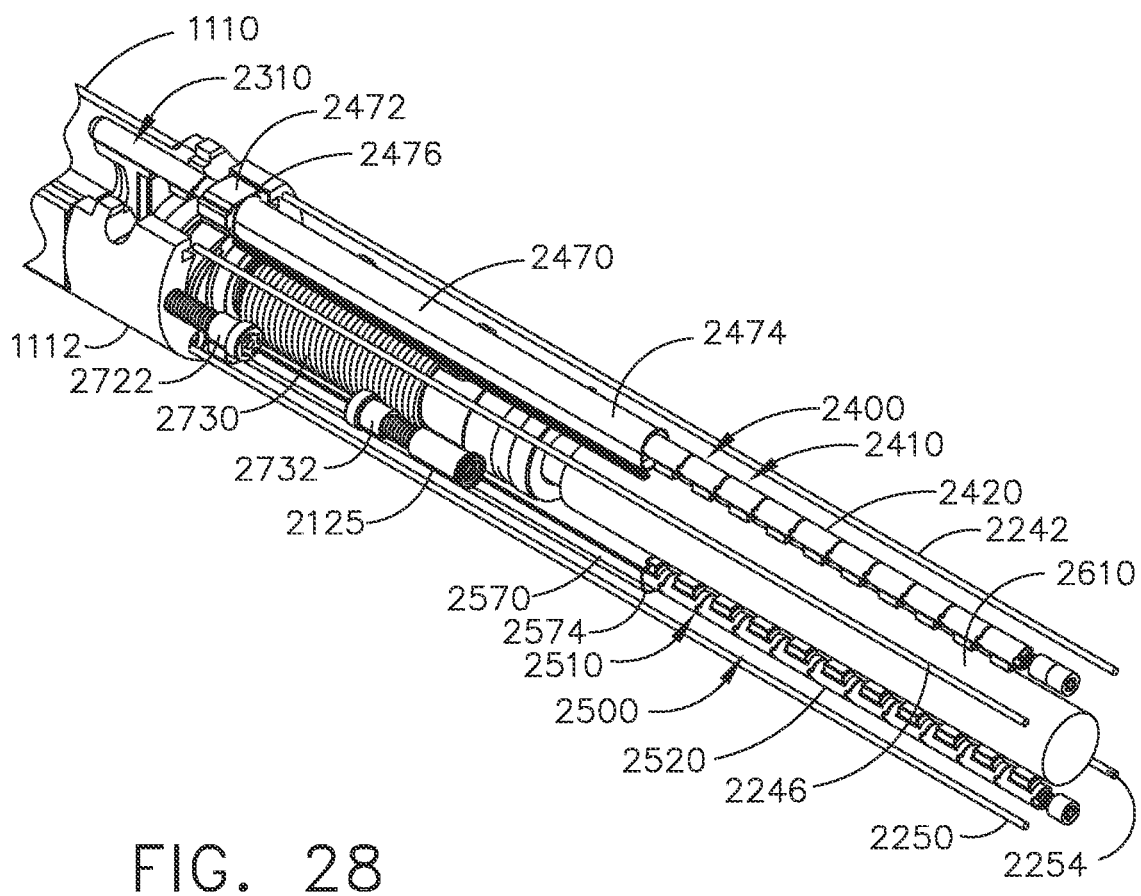
FIG. 28 is another partial perspective view of a portion of the surgical end effector, firing system and rotary drive system of FIG. 27 with an outer elastomeric joint assembly of an articulation joint and portions of the elongate shaft assembly omitted for clarity.
Figure 35:
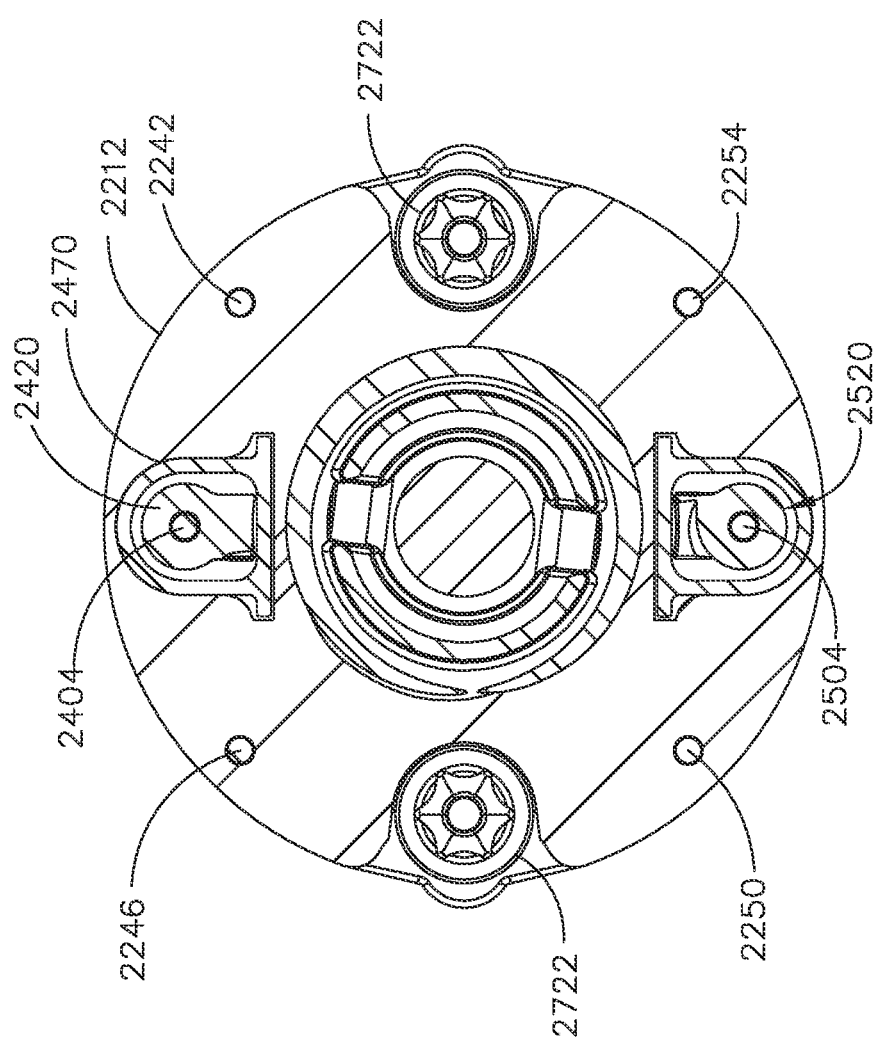
FIG. 35 is a cross-sectional end view of a portion of the surgical instrument of FIG. 19 taken along lines 35-35 in FIG. 19.

Because the radially/longitudinally segmented power screw nut arrangement disclosed herein does not have the same constraints as a three hundred sixty degree nut, the upper vertebra members 2420 in the upper series 2410 and the lower vertebra members 2520 in the lower series 2510 are constrained to ensure that their loads are transferred to the firing member in a longitudinal direction. To maintain each of the upper vertebra members 2420 in the desired orientation and to prevent the upper vertebra members 2420 from becoming snagged or disoriented when traversing through the articulation joint 2200, the upper vertebra members 2420 are aligned to pass through an upper sleeve 2470 that extends through an upper portion of the outer elastomeric joint assembly 2210 of the articulation joint 2200. See FIGS. 27, 28, and 35. A distal end 2472 of the upper sleeve 2470 is supported in the proximal end 1112 of the elongate channel 1110 and a proximal end 2474 of the upper sleeve 2470 is supported in the distal end of the proximal support shaft 2120. The upper sleeve 2470 is fabricated from a polymer or plastic material that has a low coefficient of friction and is flexible to enable the upper sleeve 2470 to flex with the outer elastomeric joint assembly 2210. The upper sleeve 2470 protects the upper vertebra members 2420 from contacting the outer elastomeric joint assembly 2210 that is fabricated from an elastomeric material that may have a higher coefficient of friction than the coefficient of friction of the material of the upper sleeve 2470. Stated another way, the upper sleeve 2470 forms a low friction, flexible, continuous, uninterrupted, and fully encapsulating path for the upper vertebra members 2420 as they traverse the articulation joint 2200.

Similarly, a lower sleeve 2570 is employed to support the lower vertebra members 2520 as they pass through the articulation joint 2200. A distal end 2572 of the lower sleeve 2570 is supported in the proximal end of the elongate channel and a proximal end of the lower sleeve 2570 is supported in the distal end of the proximal support shaft 2120. Like the upper sleeve 2470, the lower sleeve 2570 is fabricated from a polymer or plastic material that has a low coefficient of friction and is flexible to enable the lower sleeve 2570 to flex with the outer elastomeric joint assembly 2210. The lower sleeve 2570 protects the lower vertebra members 2520 from contacting the outer elastomeric joint assembly 2210 as they pass through the articulation joint 2200. Stated another way, the lower sleeve 2570 forms a low friction, flexible, continuous, uninterrupted, and fully encapsulating path for the lower vertebra members 2520 as they traverse the articulation joint 2200. In various embodiments, the upper sleeve 2470 and the lower sleeve 2570 are configured to bend freely without creating a kink. To prevent the formation of kinks in the sleeves, in at least one arrangement, the sleeves 2470, 2570 are supported within the outer elastomeric joint assembly 2210 such that the sleeves may move axially. For example, when the articulation joint angles up, the lower sleeve 2570 may slide distally and have a large bend radius; the upper sleeve 2470 in the same example, may slide proximally and have a tighter bend radius. By moving axially, the amount of material exposed outside of the joint assembly 2210 which might otherwise be susceptible to kinking under a tight bend radius is reduced. In at least one arrangement, the distal end 2472 of the upper sleeve 2470 is formed with an upper scoop 2476 that is configured to funnel the upper vertebra members 2420 into the anvil cap 1260. Similarly, the distal end of the lower sleeve 2570 may be formed with a lower scoop that is configured to funnel the lower vertebra members 2520 into the channel slot 1140 in the elongate channel 1110.

Figure 36:
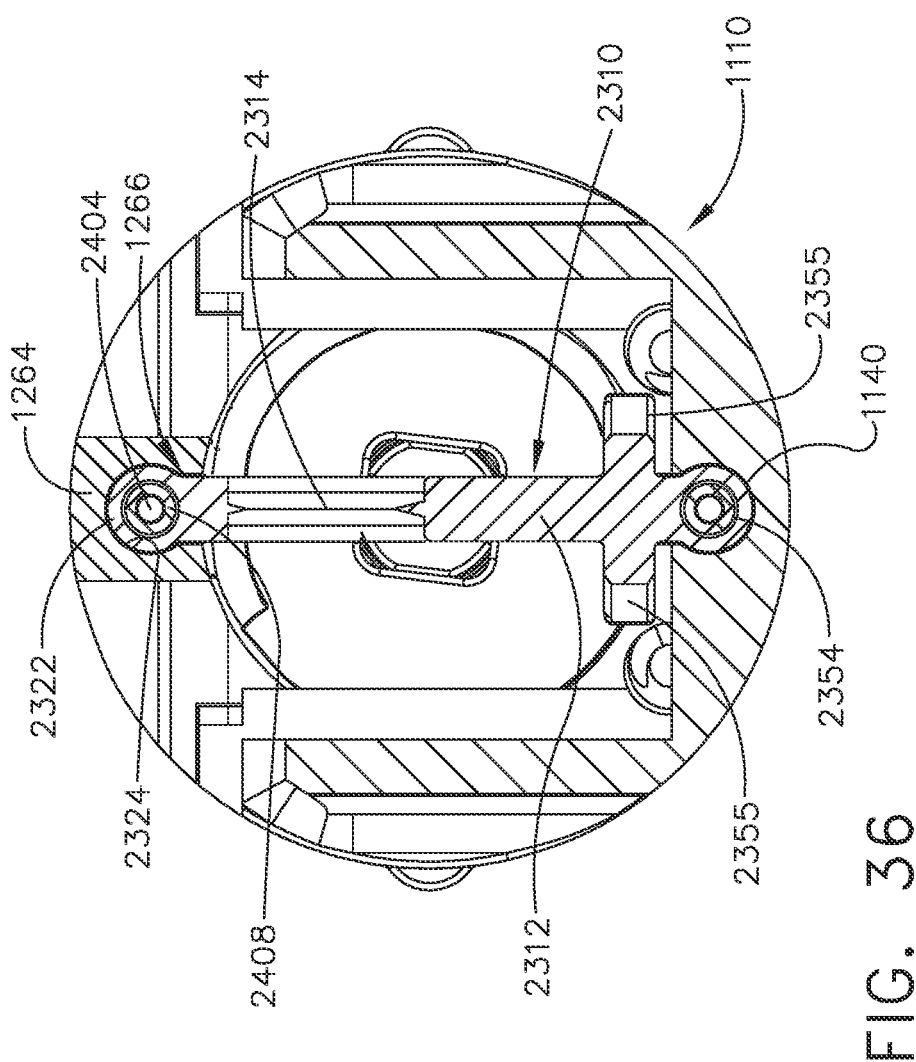
FIG. 36 is a cross-sectional end view of a portion of the surgical instrument of FIG. 19 taken along lines 36-36 in FIG. 19.
Figure 37:
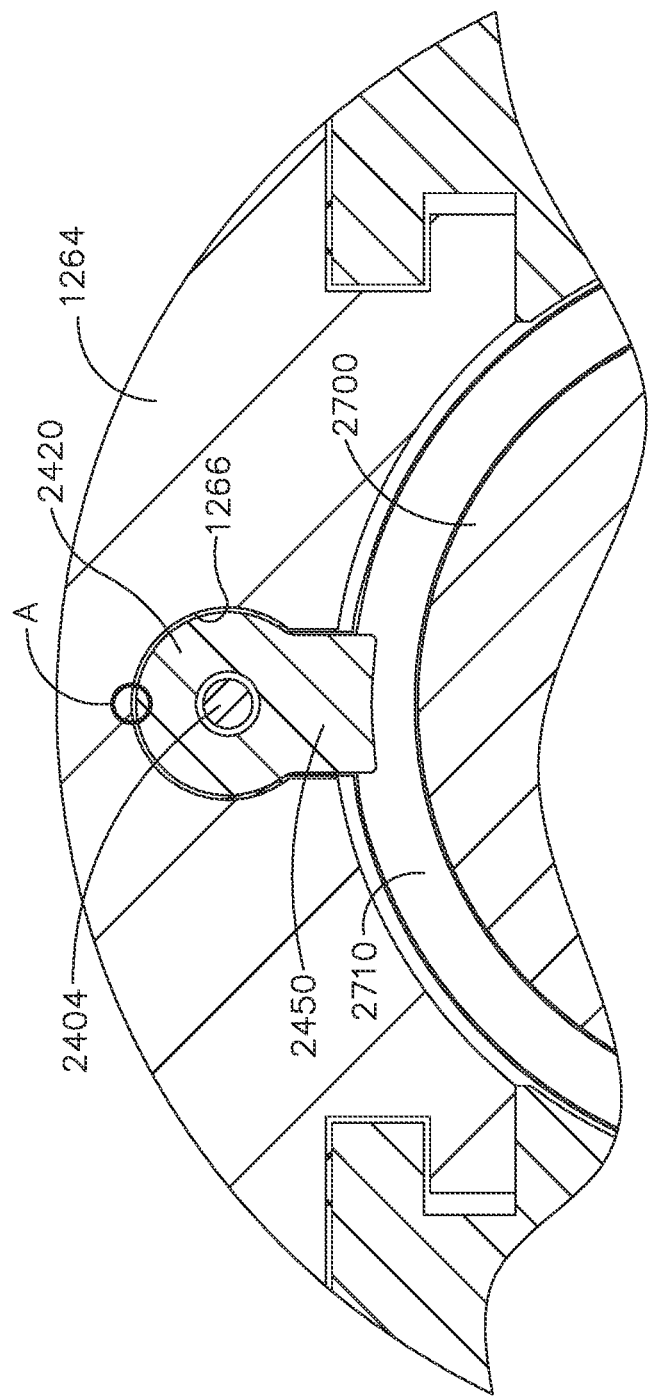
FIG. 37 is a partial cross-sectional view of a portion of an anvil cap and an upper vertebra member of the surgical instrument of FIG. 19 in accordance with at least one aspect of the present disclosure.

As indicated above, the anvil mounting portion 1230 comprises a pair of laterally extending mounting pins 1232 that are configured to be received in corresponding mounting cradles or pivot cradles 1120 that are formed in the proximal end 1112 of the elongate channel 1110. The mounting pins 1232 are pivotally retained within the mounting cradles 1120 by an anvil cap 1260 that is attached to the proximal end 1112 of the elongate channel 1110 in the above-described manners. The anvil cap 1260 comprises a proximal end 1262 and a distal end 1264 and has a keyhole-shaped vertebra passage 1266 extending therethrough to accommodate passage of the top firing member feature 2320 and upper vertebra members 2420 therethrough. FIG. 36 illustrates the vertebra passage 1266 in the anvil cap 1260. When the rotary drive screw 2700 applies load to the upper vertebra members 2420, the vertebra members 2420 will tend to tilt about the area A in FIG. 37, so the upper vertebra member tooth 2450 is no longer square with the rotary drive screw 2700 and may instead experience a higher-pressure line contact. Areas B in FIG. 37 show where the upper vertebra member 2420 stops tilting. To ensure that most of the loads stay in the longitudinal direction to perform useful work, the upper vertebra member tooth 2450 must be angled the same amount as the upper vertebra member 2420 tilts. Thus, when the upper vertebra member 2420 tilts, the upper vertebra member tooth 2450 will still maintain surface contact with the helical drive member 2710 on the rotary drive screw 2700 and all loads will be directed longitudinally and not vertically. The slightly angled upper vertebra member tooth 2450 may behave like a square thread when the vertebra member 2420 is tilted and better distributes loads to lower the pressure contact. By directing most of the loads in the longitudinal direction, vertical loads are avoided which could result in the establishment of friction that would counter the longitudinal loads. The upper vertebra members 2420 react similarly as they pass down the keyhole-shaped anvil slot 1240. Likewise, the lower vertebra members 2520 react similarly as they pass through the keyhole-shaped axially extending channel slot 1140 in the elongate channel 1110.

Figure 38:
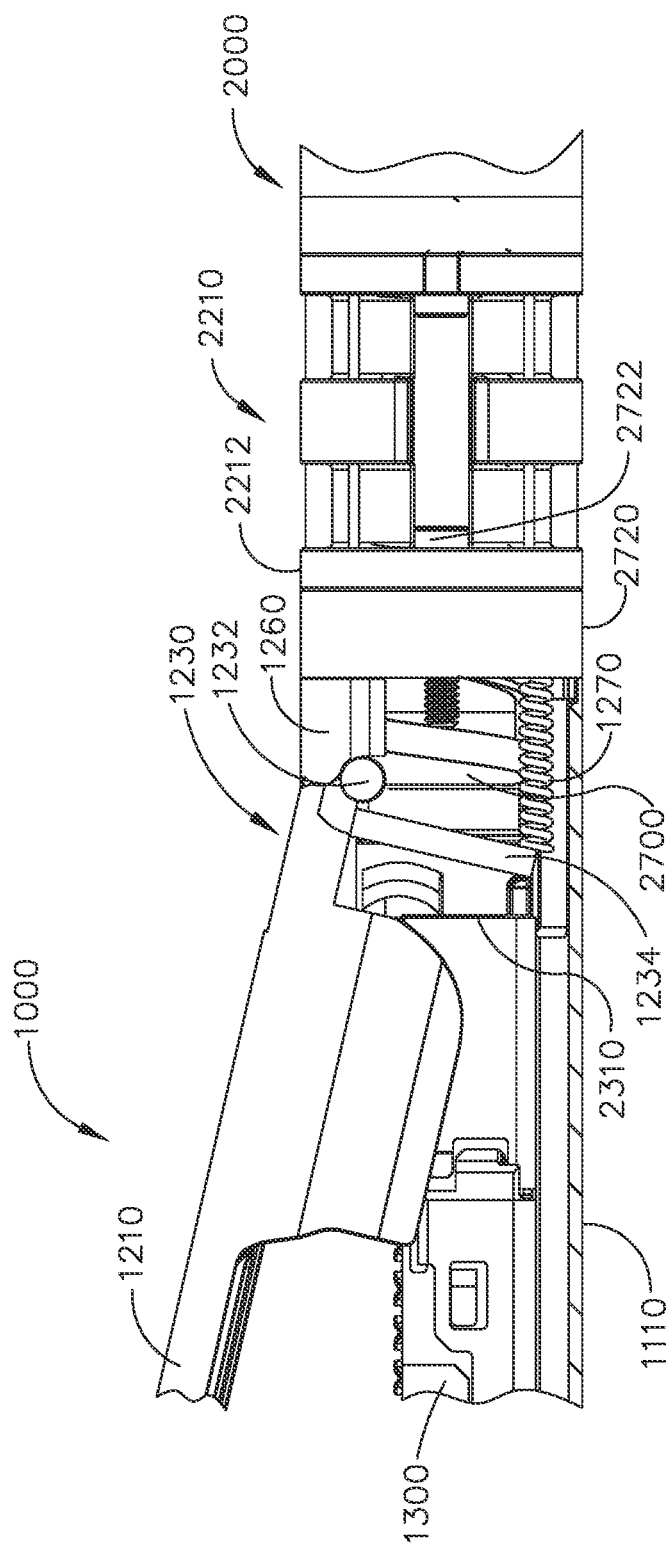
FIG. 38 is a side view of a portion of the surgical end effector of the surgical instrument of FIG. 19 with an anvil thereof in an open position in accordance with at least one aspect of the present disclosure and with portions of the surgical end effector omitted for clarity.

In the illustrated arrangement, the anvil 1210 is moved to the open position by a pair of anvil springs 1270 that are supported within the proximal end of the elongate channel. See FIGS. 38, 42, and 43. The springs 1270 are positioned to apply a pivotal biasing force to corresponding anvil control arms 1234 that may be integrally formed with anvil mounting portion 1230 and extend downwardly therefrom. See FIG. 38.

Figure 39:
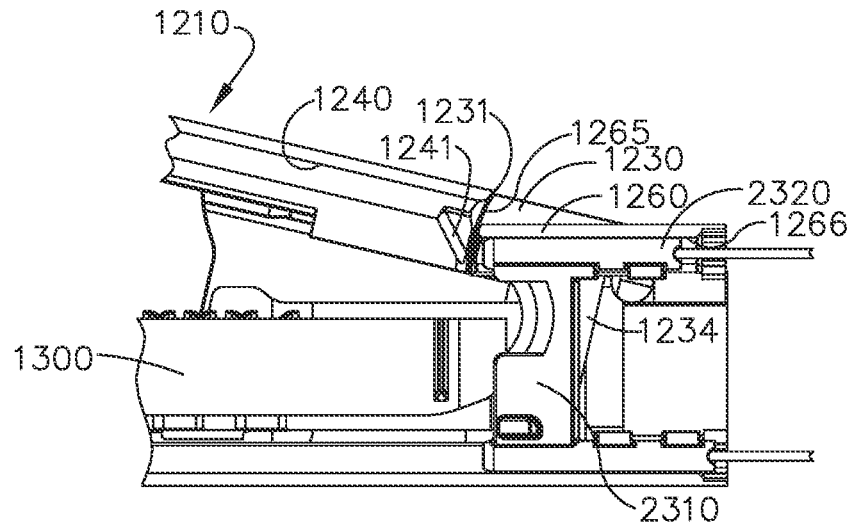
FIG. 39 is a partial cross-sectional side view of the surgical end effector of FIG. 38 with the anvil in an open position and the firing member in the home or starting position in accordance with at least one aspect of the present disclosure.
Figure 40:
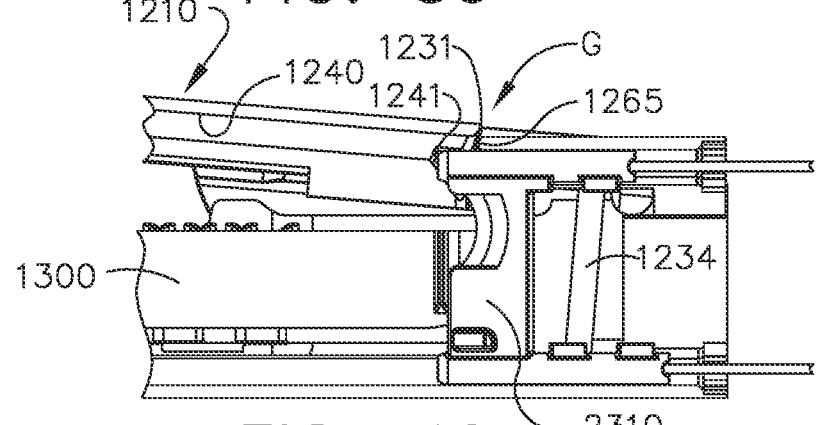
FIG. 40 is another partial cross-sectional side view of the surgical end effector of FIG. 39 with the anvil in a partially closed position.
Figure 41:
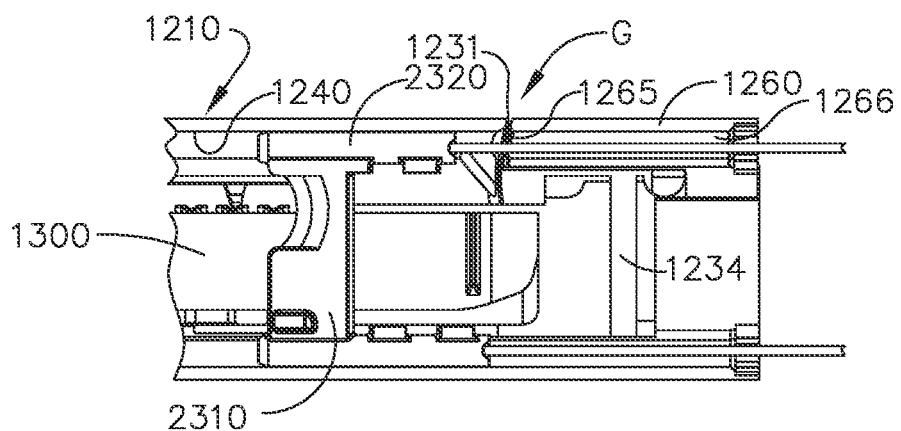
FIG. 41 is another partial cross-sectional side view of the surgical end effector of FIG. 39 with the anvil in a fully closed position and the firing member distally advancing through the surgical end effector.

FIGS. 39-41 illustrate portions of the anvil 1210, the firing member 2310, and the anvil cap 1260 when the anvil 1210 is open (FIG. 39), when the anvil 1210 is partially closed (FIG. 40) and after the firing member has been advanced distally from the home or starting position (FIG. 41). As can be seen in FIG. 39, when the firing member 2310 is in the home or starting position, the top firing member feature 2320 is completely received within the vertebra passage 1266 in the anvil cap 1260. During a firing stroke, the top firing member feature 2320 and the upper vertebra members 2410 in the upper series 2410 must transition from the vertebra passage 1266 in the anvil cap 1260 to the keyhole-shaped anvil slot 1240. Thus, it is desirable to minimize any gap "G" between the anvil mounting portion 1230 and a distal end 1264 of the anvil cap 1260. To minimize this gap G while facilitate unimpeded pivotal travel of the anvil 1210, the distal end 1264 of the anvil cap 1260 is formed with a curved cap surface 1265 that matches a curved mating surface 1231 on the anvil mounting portion 1230. Both surfaces 1265, 1231 are curved and concentric about the pivot axis PA or some other reference point. Such arrangement allows the anvil 1210 to move radially and not interfere with the anvil cap 1260 while maintaining a minimal gap G therebetween. The gap G between the anvil mounting portion 1230 and the distal end 1264 of the anvil cap 1260 is significantly shorter than a length of an upper vertebra member 2420 which facilitates easy transition of each upper vertebra member 2420 from the vertebra passage 1266 in the anvil cap 1260 to the keyhole-shaped anvil slot 1240. In addition, to further assist with the transition of the top firing member feature 2320 into the keyhole-shaped anvil slot 1240, a ramped surface 1241 is formed adjacent the curved mating surface 1231 on the anvil mounting portion 1230. As the firing member 2310 is initially advanced distally from the home or starting position, a distal end of the top firing member feature 2320 contacts the ramped surface 1241 and begins to apply a closing motion to the anvil 1210 as can be seen in FIG. 40. Further distal advancement of the firing member 2310 during the firing stroke or firing sequence causes the top firing member feature to enter the keyhole shaped anvil slot 1240 to completely close the anvil 1210 and retain the anvil 1210 in the closed position during the firing sequence. See FIG. 41.

Figure 15:
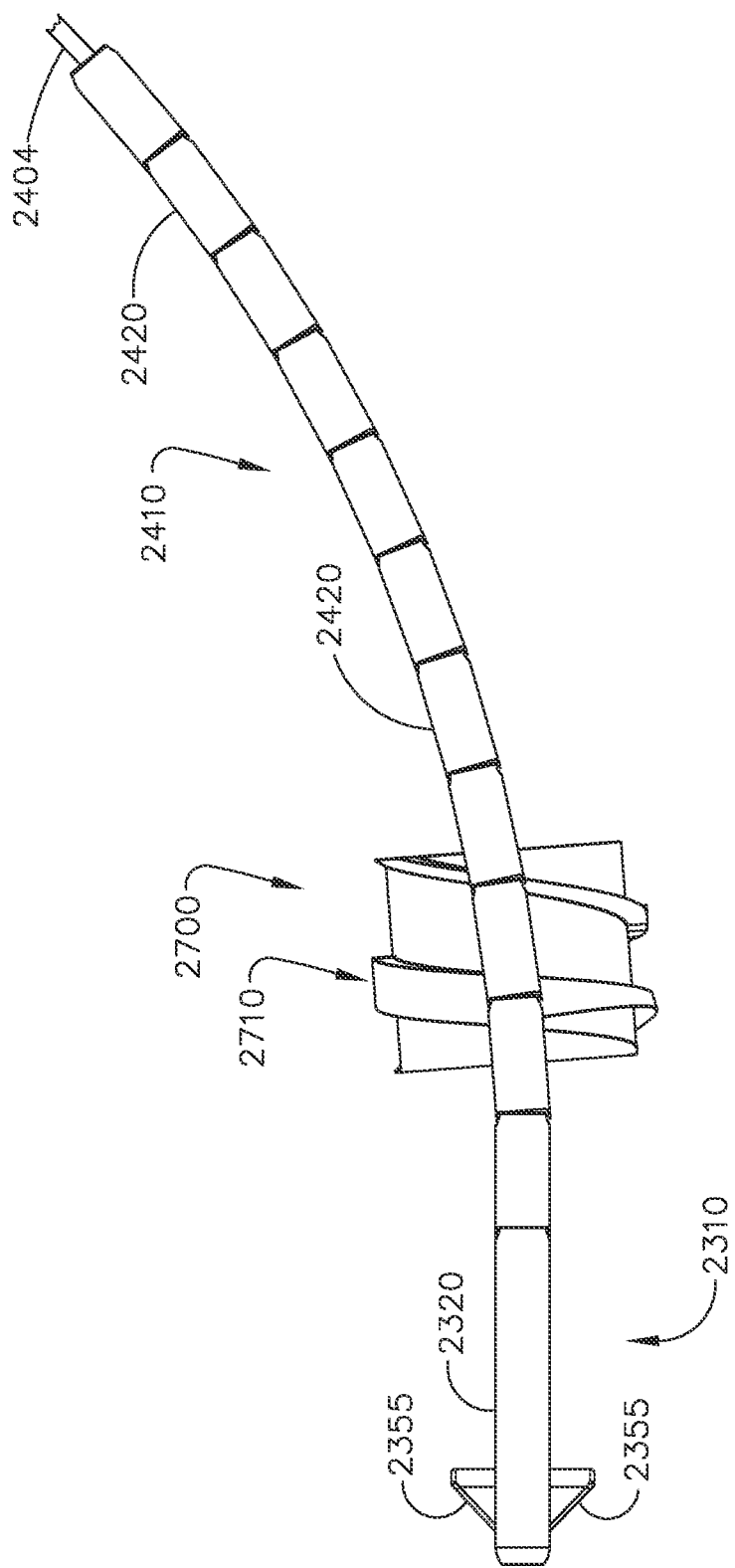
FIG. 15 is a top view of a firing member and upper and lower flexible spine assemblies in engagement with the rotary drive screw of FIG. 9.
Figure 42:
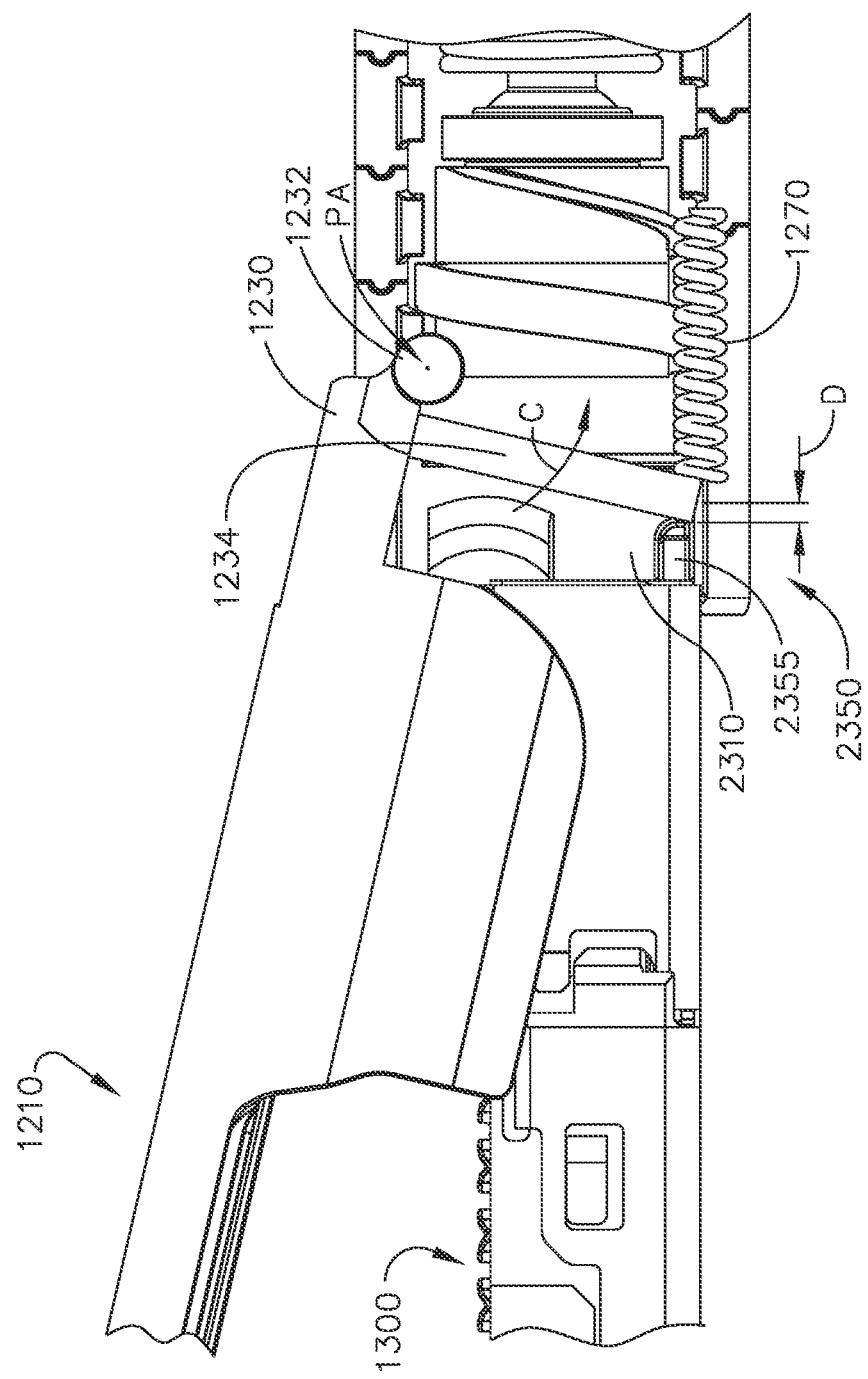
FIG. 42 is a partial side elevational view of the surgical end effector of FIG. 19 with portions thereof omitted for clarity to illustrate the anvil opening springs applying an opening motion to the anvil and with the firing member in a home or starting position.
Figure 43:
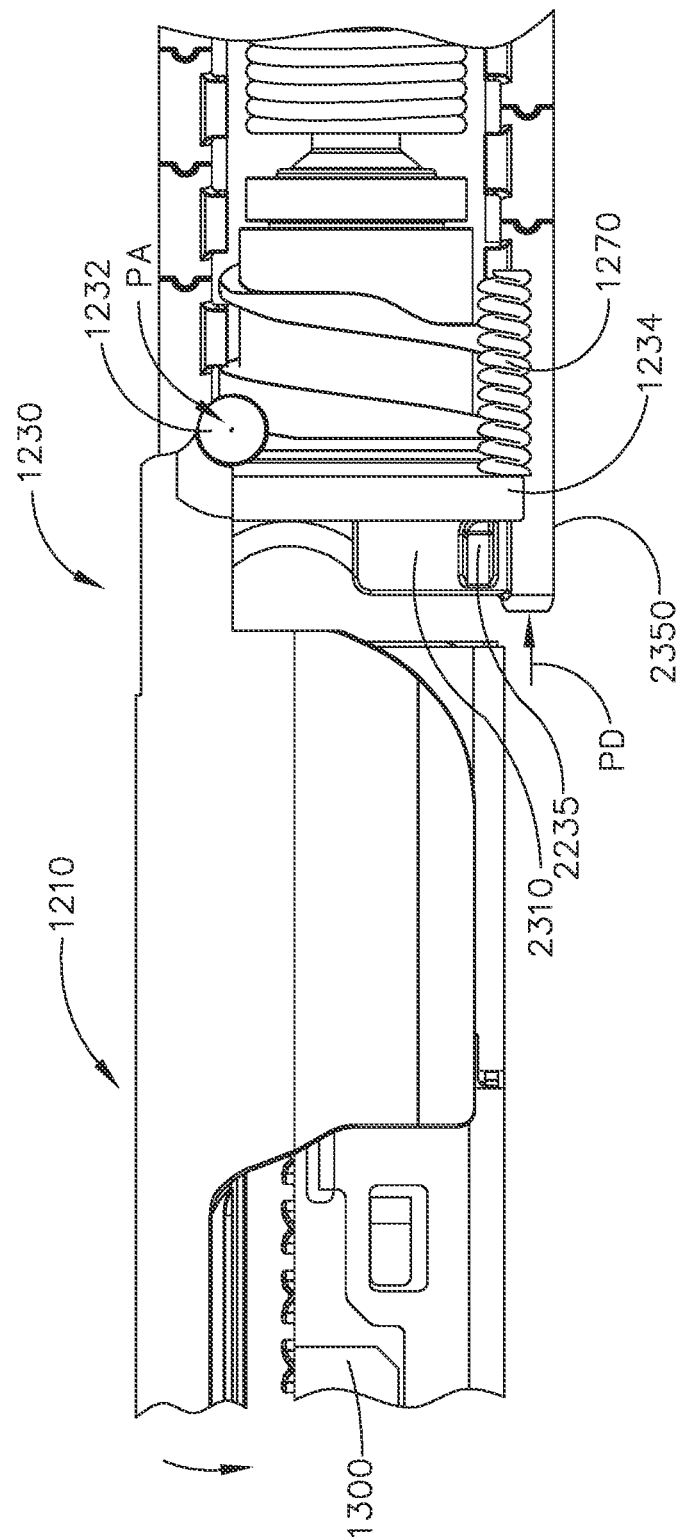
FIG. 43 is another partial side view of the surgical end effector of FIG. 42, after the firing member has moved proximally a short distance to apply a quick closure motion to the anvil for grasping purposes.

In general, the highest firing forces established in an endocutter are associated with cutting and stapling tissue. If those same forces can be used to close the anvil, then the forces generated during pre-clamping and grasping of tissue can be high as well. In at least one arrangement, the firing member body 2312 further comprises a firing member wing or tab 2355 that extends laterally from each lateral side of the firing member body 2312. See FIGS. 15 and 36. The firing member wings 2355 are positioned to contact the corresponding anvil control arms 1234 when the firing member 2310 is driven in the proximal direction PD from the home or starting position to quickly close the anvil 1210 for grasping purposes. In at least one arrangement, when the firing member 2310 is in the home or starting position, the firing member wings 2355 are located distal to the anvil control arms 1234 as shown in FIG. 42. When the firing member 3210 is moved proximally, the firing member wings 2355 push the anvil control arms 1234 (pivotal direction C) against the bias of the anvil springs 1270. See FIG. 42. In one arrangement, the firing member 2310 only has to move a short distance D to pivot the anvil 1210 to a closed position. In one embodiment, distance D may be approximately 0.070 inches long, for example. This short movement allows for a quick response. Because the anvil pivot point or pivot axis PA is relatively far from the firing member wings 2355 which creates a substantial moment arm, the proximal movement of the firing member 2310 (and firing member wings 2355) results in an application of high pre-compression torque to the anvil 1210 to move the anvil 1210 to a closed position. Thus, the firing member wings 2355 may be referred to herein as "pre-compression features". See FIG. 43. Thus, the clinician may use the surgical end effector 1000 to grasp and manipulate tissue between the anvil 1210 and the surgical staple cartridge 1300 without cutting the tissue and forming the staples, by advancing the firing member 2310 proximally the short distance D to cause the anvil 1210 to quickly pivot to a closed position.

The firing member 2310 may be moved in the proximal direction PD by rotating the rotary drive screw 2700 in a second rotary direction. Thus, when the firing member 2310 is in the "home" or starting position, the anvil 1210 may be biased into the fully open position by the anvil springs 1270. Activation of the rotary drive system 2600 to apply a rotary motion to the rotary drive screw 2700 in a first rotary direction will cause the firing member 2310 to be advanced distally from the home or starting position to apply an anvil closure motion to the anvil 1210 to move the anvil closed to clamp the target tissue between the anvil 1210 and the surgical staple cartridge 1300. Continued rotation of the rotary drive screw in the first rotary direction will cause the firing member 2310 to continue to distally advance through the surgical end effector 1000. As the firing member 2310 moves distally, the firing member 2310 contacts a sled 1312 (FIG. 19) that is supported in the surgical staple cartridge 1300 and drives the sled 1312 distally through the staple cartridge body 1302. When the firing member 2310 is in the home or starting position, the surgeon may wish to use the surgical end effector to grasp and manipulate tissue. To do so, the rotary drive system is actuated to apply a second rotary drive motion to the rotary drive screw 2700 in a second rotary direction that is opposite to the first rotary direction. Such rotary movement of the rotary drive screw 2700 in the second rotary direction will drive the firing member 2310 proximally from the starting position and cause the anvil 1210 to quickly pivot to the closed position. Thus, in accordance with at least one embodiment, the "home or starting position" of the firing member 2310 is not its proximal-most position.

If during the firing process, the rotary drive system 2600 quits rotating, the firing member 2310 may become stuck within the surgical end effector. In such instance, the top firing member feature 2320 may remain engaged with the anvil 1210 and the bottom firing member feature 2350 may remain engaged with the elongate channel 1110 and thereby prevent the surgeon from moving the anvil 1210 to an open position to release the tissue clamped between anvil 1210 and surgical staple cartridge 1300. This could occur, for example, if the motor or other control arrangement supplying the rotary drive motions to the rotary drive shaft 2610 fails or otherwise becomes inoperative. In such instances, the firing member 2310 may be retracted back to the home or starting position within the surgical end effector 1000 by pulling the top cable 2404 and the lower cable 2504 in a proximal direction. For example, a proximal portion of the top cable 2404 and a proximal portion of the lower cable 2505 may be spooled on a rotary spool or cable-management system 2009 (FIG. 2) in the housing portion of the surgical instrument 10 that is configured to payout the top cable 2404 and lower cable 2504 during the firing stroke and also retract the cables 2404, 2504 in a proximal direction should the firing member 2310 need to be retracted. The cable management system 2009 may be motor powered or manually powered (ratchet arrangement, etc.) to apply retraction motions to the cables 2404, 2504. When the cables 2404, 2504 are retracted, the upper vertebra members 2420 and lower vertebra members 2520 will cause the rotary drive screw 2700 to spin in reverse.

The following equation may be used to determine whether the rotary drive screw 2700 will spin in reverse depending upon the lead (L), pitch diameter ($d_p$), tooth angle ($\alpha$) and friction ($\mu$):

$$\mu \geq \frac{L}{\pi d_p} \cos\alpha$$

The rotary drive screw 2700 may self-lock if the above equation is true. For the most part, in many instances, the pitch diameter is mostly fixed for an endocutter, but the lead and tooth angle are variable. Because the upper vertebra member teeth 2450 and lower vertebra member teeth 2550 are mostly square, the rotary drive screw 2700 is more likely to be back drivable (cos (90)=1). The leads of the upper vertebra member teeth 2450 and lower vertebra member teeth 2550 may also be advantageous in that the rolling friction between the vertebra members 2420, 2520 and the rotary drive screw 2700 is more likely to enable the rotary drive screw 2700 to be back driven. Thus, in the event of an emergency, the surgeon can pull on the upper and lower cables 2404, 2504 in the proximal direction to cause the firing member 2310 to fully retract for a quick "bailout".

As indicated above, the relative control motions for the rotary drive system 2600, as well as the various cable-management systems employed in connection with the firing system 2300 and the articulation control system 2240, may be supported within a housing 2002 which may be handheld or comprise a portion of a larger automated surgical system. The firing system 2300, articulation control system 2240, and the rotary drive system 2600 may, for example, be motor-controlled and operated by one or more control circuits.

Figure 44:
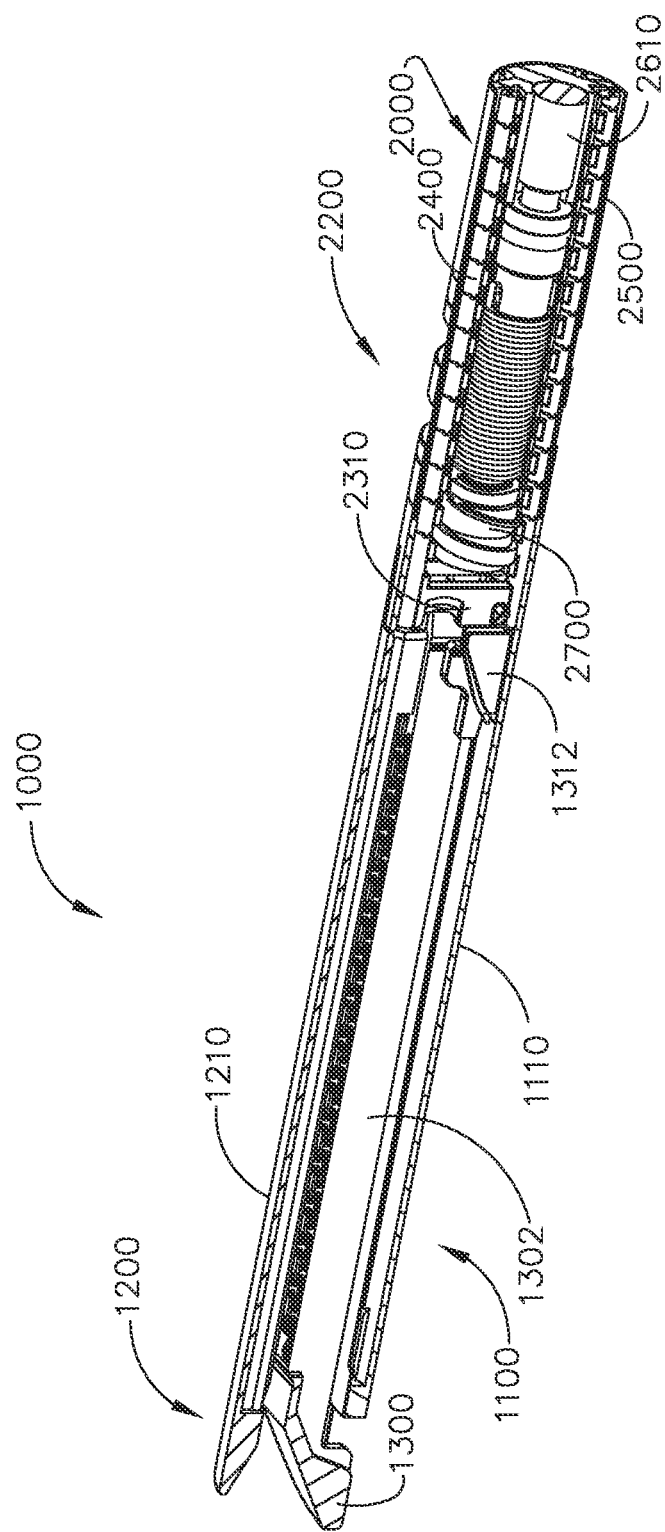
FIG. 44 is a cross-sectional view of the surgical end effector of FIG. 19 with the jaws thereof in a closed position and the firing member thereof in a proximal-most position.

One method of using the surgical instrument 10 may involve the use of the surgical instrument 10 to cut and staple target tissue within a patient using laparoscopic techniques. For example, one or more trocars may have been placed through the abdominal wall of a patient to provide access to a target tissue within the patient. The surgical end effector 1000 may be inserted through one trocar and one or more cameras or other surgical instruments may be inserted through the other trocar(s). To enable the surgical end effector 1000 to pass through the trocar cannula, the surgical end effector 1000 is positioned in an unarticulated orientation and the jaws 1100 and 1200 must be closed. To retain the jaws 1100 and 1200 in the closed position for insertion purposes, for example, the rotary drive system 2600 may be actuated to apply the second rotary motion to the rotary drive screw 2700 to cause the firing member 2310 to move proximally from the starting position to move the anvil 1210 (jaw 1200) to the closed position. See FIG. 44. The rotary drive system 2600 is deactivated to retain the firing member 2310 in that position. Once the surgical end effector has passed into the abdomen through the trocar, the rotary drive system 2600 may be activated to cause the rotary drive screw 2700 to drive the firing member 2310 distally back to the starting position wherein the anvil springs 1270 will pivot the anvil 1210 to the open position. See FIG. 38.

Once inside the abdomen and before engaging the target tissue, the surgeon may need to articulate the surgical end effector 1000 into an advantageous position. The articulation control system 2240 is then actuated to articulate the surgical end effector in one or more planes relative to a portion of the elongate shaft assembly 2000 that is received within the cannula of the trocar. Once the surgeon has oriented the surgical end effector 1000 in a desirable position, the articulation control system 2240 is deactivated to retain the surgical end effector 1000 in the articulated orientation. The surgeon may then use the surgical end effector to grasp the target tissue or adjacent tissue by activating the rotary drive system to rotate the rotary drive screw in the second rotary direction to move the firing member proximally to cause the anvil 1210 to rapidly close to grasp the tissue between the anvil 1210 and the surgical staple cartridge 1300. The anvil 1210 may be opened by reversing the rotation of the rotary drive screw 2700. This process may be repeated as necessary until the target tissue has be properly positioned between the anvil 1210 and the surgical staple cartridge 1300.

Once the target tissue has been positioned between the anvil 1210 and the surgical staple cartridge, the surgeon may commence the closing and firing process by activating the rotary drive system 2600 to drive the firing member 2310 distally from the starting position. As the firing member 2310 moves distally from the starting position, the firing member 2310 applies a closure motion to the anvil 1210 and moves the anvil 1210 from the open position to the closed position in the manners discussed above. As the firing member 2310 moves distally, the firing member 2310 retains the anvil 1210 in the closed position thereby clamping the target tissue between the anvil 1210 and the surgical staple cartridge 1300. As the firing member 2310 moves distally, the firing member 2310 contacts a sled 1312 supported in the surgical staple cartridge 1300 and also drives the sled 1312 distally through the staple cartridge body 1302. The sled 1312 serially drives rows of drivers supported in the staple cartridge toward the clamped target tissue. Each driver has supported thereon one or more surgical staples or fasteners which are then driven through the target tissue and into forming contact with the underside of the anvil 1210. As the firing member 2310 moves distally, the tissue cutting edge 2314 thereon cuts through the stapled tissue.

Figure 45:
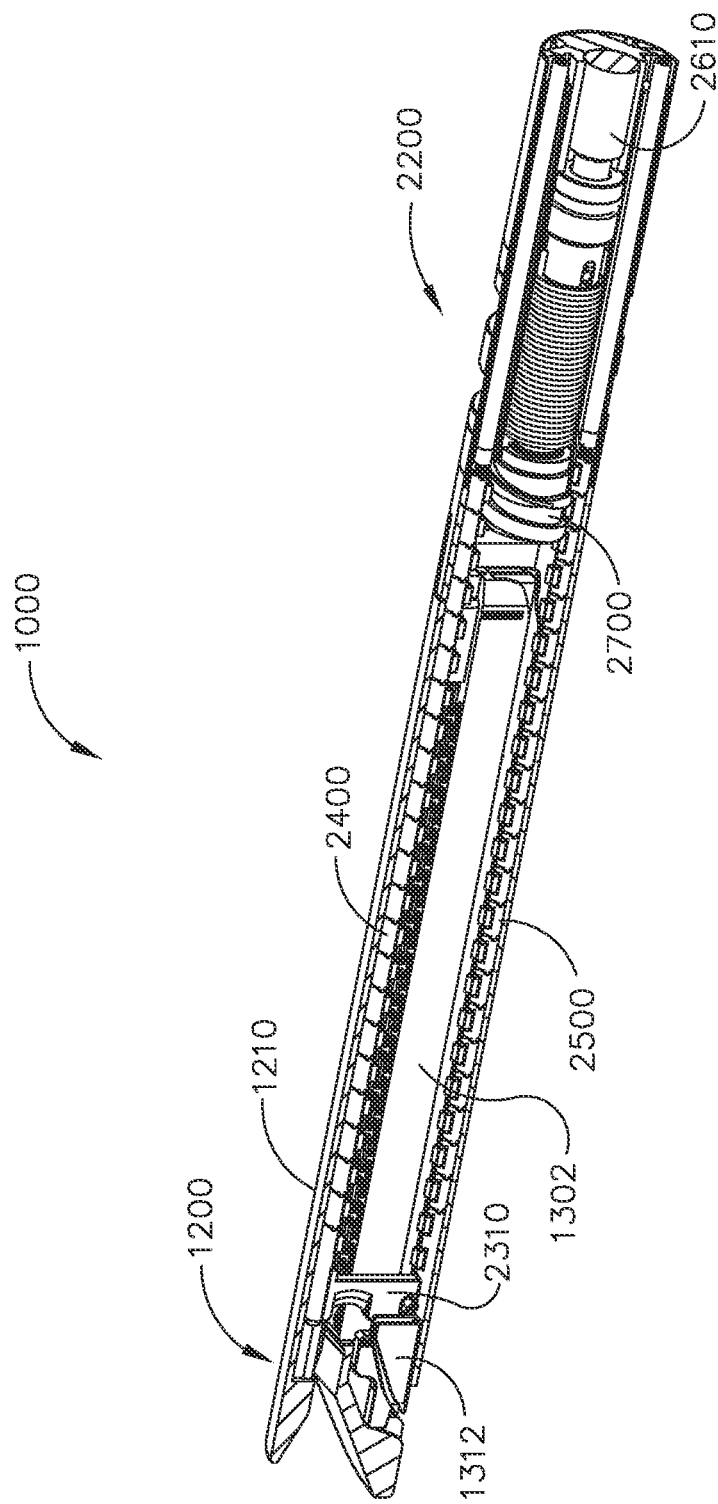
FIG. 45 is another cross-sectional view of the surgical end effector of FIG. 44, after the firing member has been distally advanced to the ending position within the surgical end effector.

After the firing member 2310 has been driven distally to the ending position within the surgical end effector 1000 (FIG. 45), the rotary drive system 2600 is reversed which causes the firing member 2310 to retract proximally back to the home or starting position. Once the firing member 2310 has returned to the starting position, the anvil springs 1270 will pivot the anvil 1210 to the open position to enable the surgeon to release the stapled tissue from the surgical end effector 1000. Once the stapled tissue has been released, the surgical end effector may be withdrawn out of the patient through the trocar cannula. To do so, the surgeon must first actuate the articulation control system 2240 to return the surgical end effector 1000 to an unarticulated position and actuate the rotary drive system to drive the firing member 2310 proximally from the home or starting position to close the jaws. Thereafter, the surgical end effector 1000 may be withdrawn through the trocar cannula. If during the firing process or during the retraction process, the firing system becomes inoperative, the surgeon may retract the firing member 2310 back to the starting position by applying a pulling motion to the cables 2404, 2505 in the proximal direction in the various manners described herein.

Figure 46:
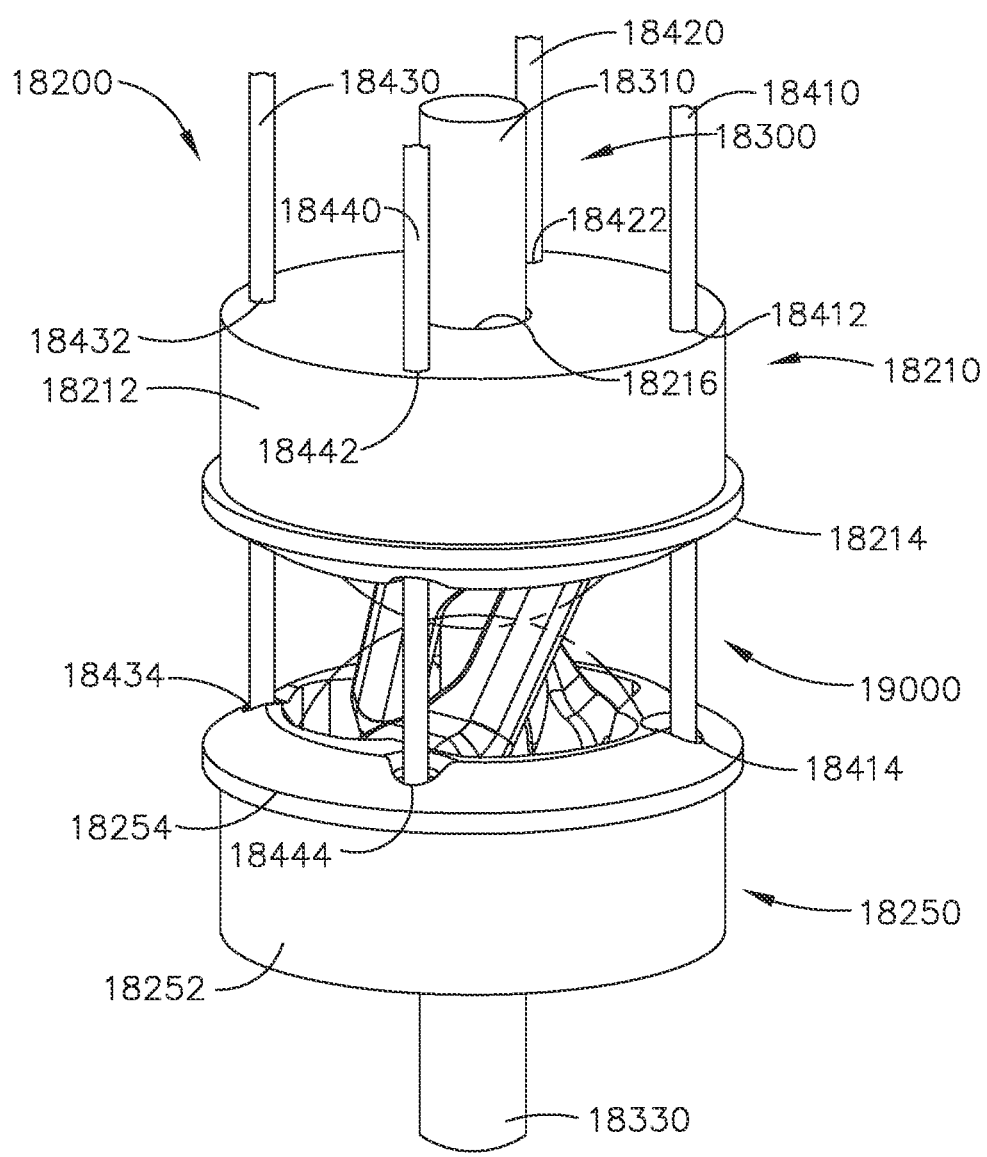
FIG. 46 is a perspective view of another articulation joint embodiment for a surgical instrument with the joint in an unarticulated orientation.
Figure 47:
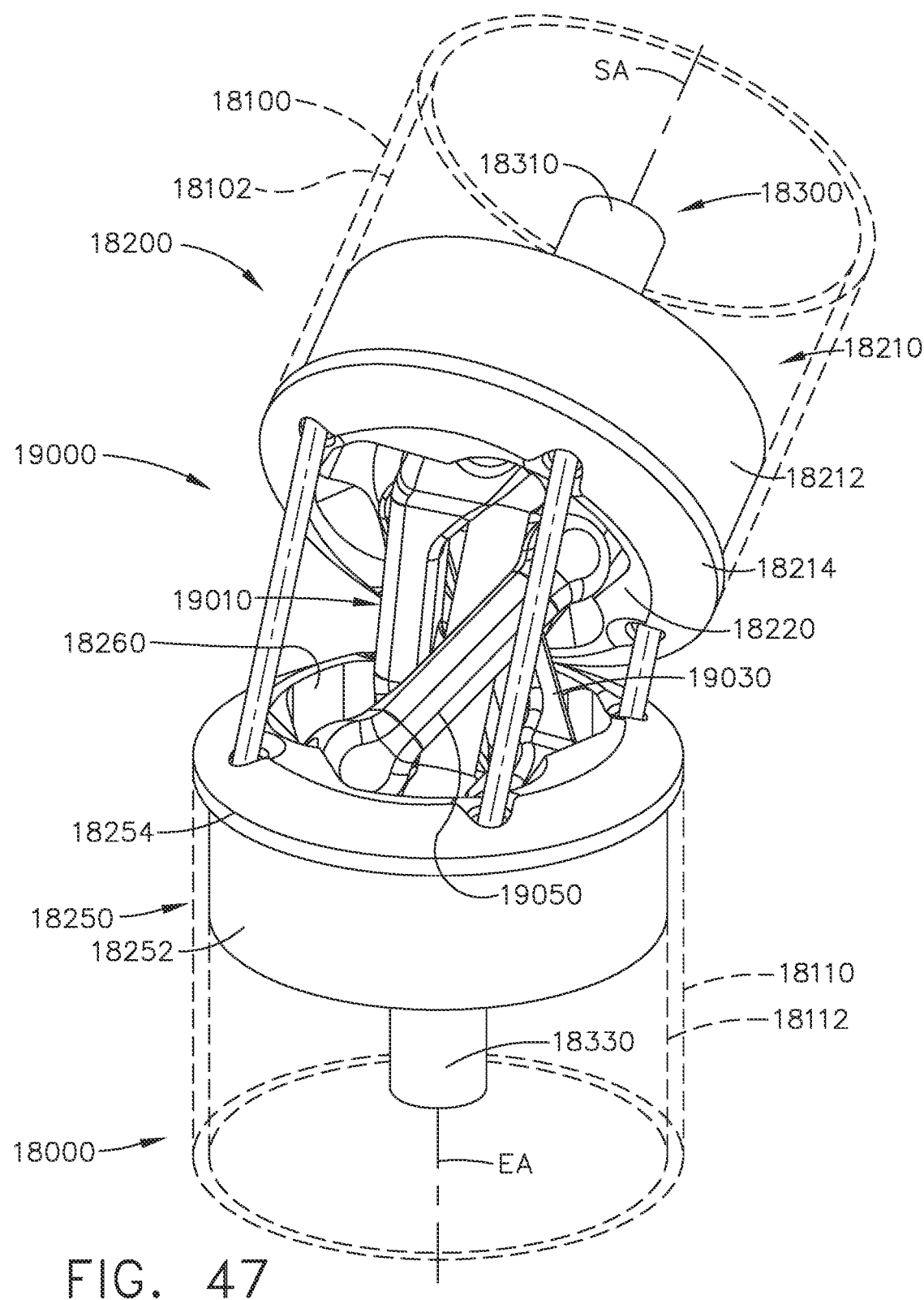
FIG. 47 is another perspective view of the articulation joint of FIG. 46 in an articulated orientation.
Figure 48:
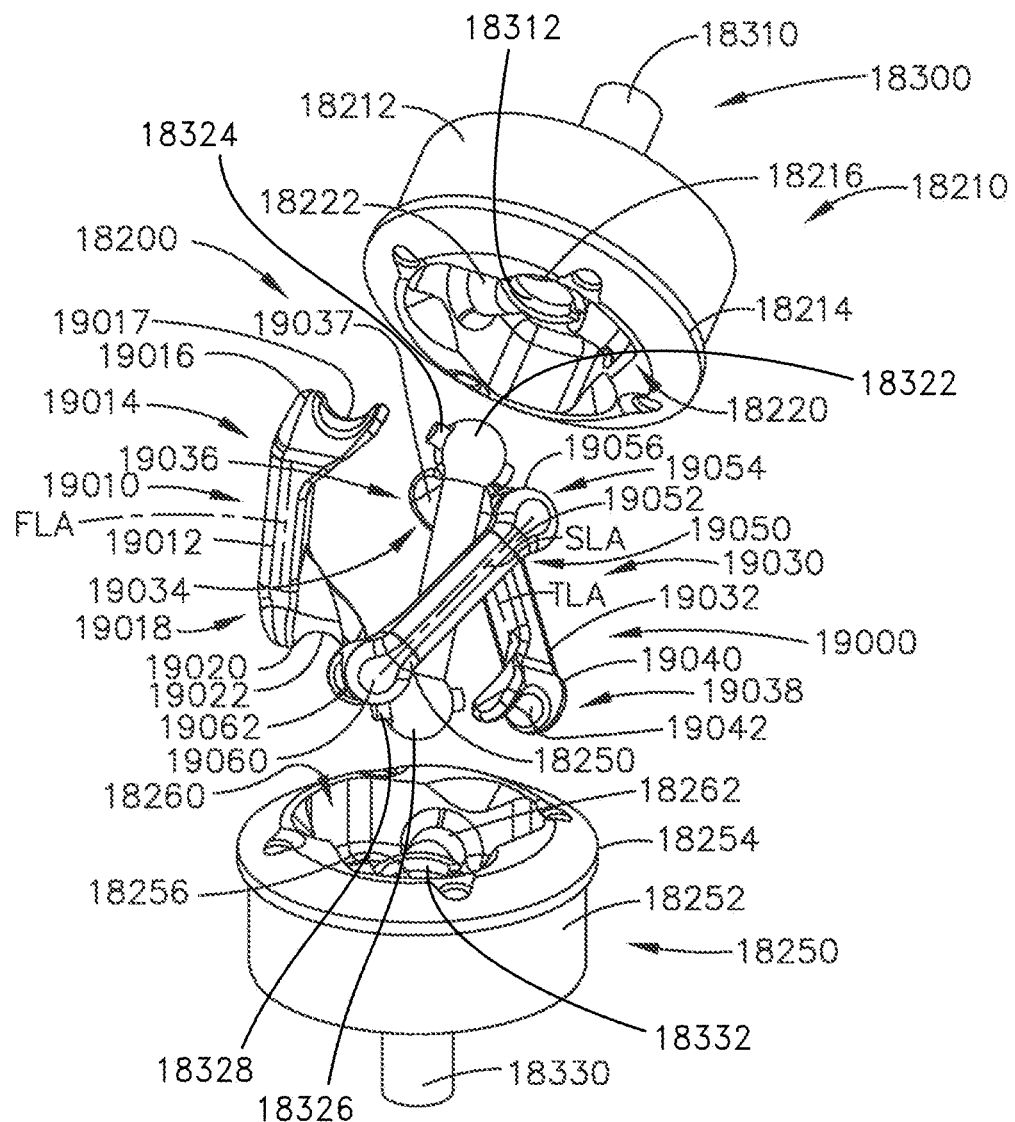
FIG. 48 is an exploded assembly view of the articulation joint of FIG. 46.

FIGS. 46-48 illustrate another form of articulation joint 18200 that comprises a proximal joint member 18210 and a distal joint member 18250. The proximal joint member 18210 is configured to be attached to a distal end of an elongate shaft assembly 18100 (FIG. 47) that is coupled to a housing or other portion of a surgical instrument in the various manners disclosed herein. The distal joint member 18250 may be attached to a closure tube arrangement 18110 (FIG. 47) that is configured to apply closing and/or opening motions to a movable jaw of an end effector 18000. In alternative arrangements, the distal joint member 18250 may be attached to one of the end effector jaws or other mounting portion of the end effector 18000. For example, the distal joint member 18250 may be attached to an elongate channel of an endo-cutter arrangement in the various manners disclosed herein. In at least one arrangement, for example, the shaft assembly 18100 defines a shaft axis SA and the end effector 18000 defines and end effector axis EA. The articulation joint facilitates selective articulation of the end effector 18000 relative to the shaft assembly 18100 in an articulation plane between an unarticulated position wherein the end effector axis EA is axially aligned with the shaft axis SA and articulated positions wherein the end effector axis EA is not aligned with the shaft axis SA.

As can be seen in FIGS. 46-48, the proximal joint member 18210 comprises a proximal mounting hub 18212. The proximal mounting hub, for example, may be configured to be inserted into a hollow outer shaft or tube portion 18102 of an elongate shaft assembly 18100 and be attached thereto by welding, adhesive, etc. The illustrated example further comprises a distally-facing collar portion 18214 that defines a distally-facing mounting area, generally designated as 18220. See FIG. 48. To accommodate passage of various control shafts/drive members through the articulation joint 18200, the proximal joint member 18210 further comprises a proximal central passage 18216 that extends through the proximal mounting hub 18212 into the distally-facing mounting area 18220. In the illustrated example, the proximal central passage 18216 is configured to accommodate a proximal drive shaft 18310 that is a portion of a rotary drive system 18300. In other arrangements, a flexible drive shaft (not shown) may extend through the proximal central passage 18216.

The distal joint member 18250 comprises a distal mounting hub 18252 that is configured to be inserted into a hollow outer shaft 18114 or closure tube or mounting hub of a surgical end effector 18000 and be attached thereto by welding, adhesive, etc. The surgical end effector 18000 may comprise any of the surgical end effector examples disclosed herein. The illustrated example further comprises a proximally-facing collar portion 18254 that defines a proximally-facing mounting area, generally designated as 18260. In addition, the distal joint member 18250 further comprises a distal central passage 18256 that extends from the distally-facing mounting area 18220 through the distal mounting hub 18252. In the illustrated example, the distal central passage 18256 is configured to accommodate a distal drive shaft 18330 that is a portion of the rotary drive system 18300 or in other embodiments, the distal central passage 18256 may support another portion of a flexible drive shaft arrangement.

The illustrated example further comprises an articulation linkage assembly 19000 that extends between the proximal joint member 18210 and the distal joint member 18250 and is configured to operably interface therewith to facilitate articulation of the distal joint member 18250 (and the surgical end effector coupled thereto) relative to proximal joint member 18210 (and the elongate shaft assembly 18100 coupled thereto). As can be seen in FIG. 48, the articulation linkage assembly 19000 comprises a first link 19010, a second link 19030, and a third link 19050. Each of the links 19010, 19030 and 19050 is movably captured between the proximal joint member 18210 and the distal joint member 18250, but, as will be discussed in further detail below, none of the links 19010, 19030, 19050 are directly attached to either of the proximal joint member 18210 and the distal joint member 18250.

Figure 49:
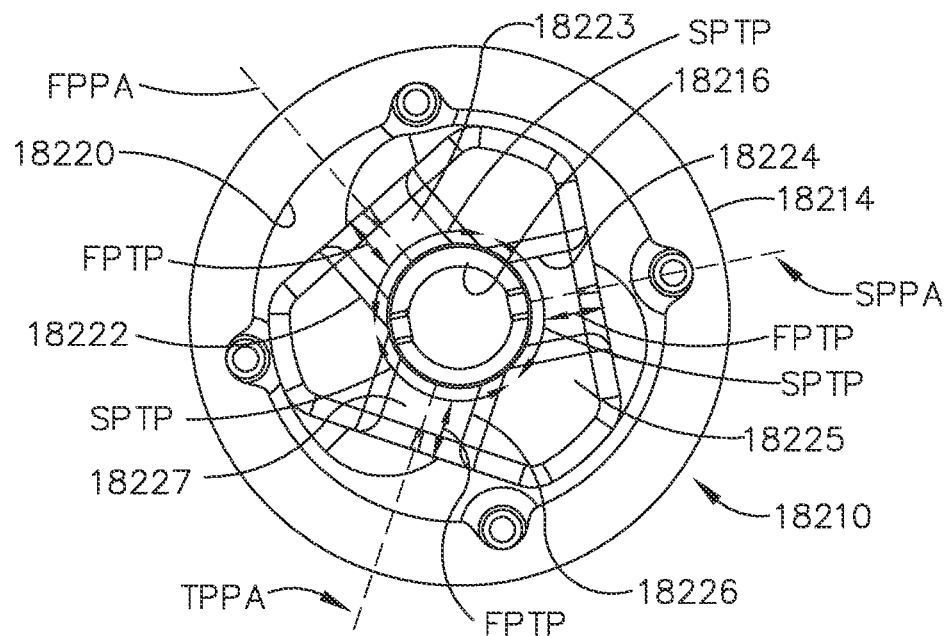
FIG. 49 is an end view of a proximal joint member of the articulation joint of FIG. 46.

In one example, the first link 19010 comprises a rigid first link body 19012 that defines a first proximal end 19014 and a first distal end 19018. The first proximal end 19104 has a first proximal saddle 19016 formed therein that is configured to be pivotally received on a corresponding first proximal mounting lug 18222 formed in the distally-facing mounting area 18220. The first proximal mounting lug 18222 has an arcuate proximal pivot surface 18223 thereon and defines a first proximal pivot axis FPPA. See FIG. 49. The first proximal saddle 19016 comprises a U-shaped proximal pivot surface 19017 that is configured to rollably or movably interface with the arcuate proximal pivot surface 18223 on the first proximal mounting lug 18222 such that the first link 19010 is movable relative to proximal joint member 18210 about the first proximal pivot axis FPPA in multiple directions or in multiple proximal travel paths. For example, the first proximal saddle 19016 can move relative to the first proximal pivot axis FPPA in a first proximal travel path FPTP and a second proximal travel path SPTP. In at least one arrangement, the first proximal travel path FPTP is transverse to the second proximal travel path SPTP. See FIGS. 49 and 51-54.

The first distal end 19108 comprises a first distal saddle 19020 formed therein that is configured to be pivotally received on a corresponding first distal mounting lug 18262 formed in the proximally-facing mounting area 18260. The first distal mounting lug 18262 has an arcuate pivot surface 18263 and defines a first distal pivot axis FDPA. See FIG.

50. The first distal saddle 19020 comprises a U-shaped pivot surface 19022 that is configured to rollably or movably interface with the arcuate pivot surface 18263 on the first distal mounting lug 18262 such that the first link 19010 is movable relative to the distal proximal joint member 18250 about the first distal pivot axis FDPA in multiple directions or multiple distal travel paths. For example, the first distal saddle 19020 can move relative to the first distal pivot axis FDPA in a first distal travel path FDTP and a second distal travel path SDTP. In at least one arrangement, the first distal travel path FDTP is transverse to the second distal travel path SDTP. See FIG. 50.

The second link 19030 comprises a rigid second link body 19032 that defines a second proximal end 19034 and a second distal end 19038. The second proximal end 19034 has a second proximal saddle 19036 formed therein that is configured to be pivotally received on a corresponding second proximal mounting lug 18224 formed in the distally-facing mounting area 18220. The second proximal mounting lug 18224 has a second arcuate proximal pivot surface 18225 thereon and defines a second proximal pivot axis SPPA. See FIG. 49. The second proximal saddle 19036 comprises a second U-shaped proximal pivot surface 19037 that is configured to rollably or movably interface with the second arcuate proximal pivot surface 18225 on the second proximal mounting lug 18224 such that the second link 19030 is movable relative to proximal joint member 18210 about the second proximal pivot axis SPPA in multiple directions or multiple proximal travel paths. For example, the second proximal saddle 19036 can move relative to the second proximal pivot axis SPPA in a first proximal travel path FPTP and a second proximal travel path SPTP. In at least one arrangement, the first proximal travel path FPTP is transverse to the second proximal travel path SPTP. See FIG. 49.

The second distal end 19038 comprises a second distal saddle 19040 that is configured to be pivotally received on a corresponding second distal mounting lug 18264 formed in the proximally-facing mounting area 18260. See FIG. 50. The second distal mounting lug 18264 has a second arcuate distal pivot surface 18265 and defines a second distal pivot axis SDPA. The second distal saddle 19040 comprises a second U-shaped distal pivot surface 19042 that is configured to rollably interface with the second arcuate distal pivot surface 18265 on the second distal mounting lug 18264 such that the second link 19030 is movable relative to the distal joint member 18250 about the second distal pivot axis SDPA in multiple directions or multiple distal paths. For example, the second distal saddle 19040 can move relative to the second distal pivot axis SDPA in a first distal travel path FDTP and a second distal travel path SDTP. In at least one arrangement, the first distal travel path FDTP is transverse to the second distal travel path SDTP. See FIG. 50.

The third link 19050 comprises a rigid third link body 19052 that defines a third proximal end 19054 and a third distal end 19058. The third proximal end 19054 has a third proximal saddle 19056 formed therein that is configured to be pivotally received on a corresponding third proximal mounting lug 18226 formed in the distally-facing mounting area 18220. The third proximal mounting lug 18226 has a third arcuate proximal pivot surface 18227 and defines a third proximal pivot axis TPPA. See FIG. 49. The third proximal saddle 19056 comprises a third U-shaped proximal pivot surface 19057 that is configured to rollably or movably interface with the third arcuate proximal pivot surface 18227 on the third proximal mounting lug 18226 such that the third link 19050 is movable relative to proximal joint member 18210 about the third proximal pivot axis TPPA in multiple directions or multiple travel paths. For example, the third proximal saddle 19056 can move relative to the third proximal pivot axis TPPA in a first proximal travel path FPTP and a second proximal travel path SPTP. In at least one arrangement, the first proximal travel path FPTP is transverse to the second proximal travel path SPTP. See FIG. 49.

The third distal end 19058 comprises a third distal saddle 19060 that is configured to be pivotally received on a corresponding third distal mounting lug 18266 formed in the proximally-facing mounting area 18260. See FIG. 50. The third distal mounting lug 18266 comprises a third arcuate distal pivot surface 18267 and defines a third distal pivot axis TDPA. The third distal saddle 19060 comprises a third U-shaped distal pivot surface 19062 that is configured to rollably or movably interface with the third arcuate distal pivot surface 18267 on the third distal mounting lug 18266 such that the third link 19050 is movable relative to the distal joint member 18250 about the third distal pivot axis TDPA in multiple directions or multiple distal travel paths. For example, the third distal saddle 19060 can move relative to the third distal pivot axis TDPA in a first distal travel path FDTP and a second distal travel path SDTP. In at least one arrangement, the first distal travel path FDTP is transverse to the second distal travel path SDTP. See FIG. 50.

In the illustrated arrangement, none of the links 19010, 19030, and 19050 are directly attached to either of the proximal joint member 18210 or the distal joint member 18250. Instead, the link assembly 19000 is supported in movable pivotal engagement with the proximal joint member 18210 and the distal joint member 18250 by a cable-based articulation system 18400. In the illustrated example, the articulation joint 18200 is operably controlled by a cable control system 18400 that comprises four flexible actuator members in the form of cables 18410, 18420, 18430, and 18440 that extend through the elongate shaft assembly to operably interface with a cable control system that may be supported within the housing of the surgical instrument. The cable control system may comprise a plurality of cable support members/capstans, pulleys, etc. that are controlled by one or more corresponding motors that are controlled by a control circuit portion of the surgical instrument. The cable control system is configured to manage the tensioning (pulling) and paying out of cables at precise times during the articulation process. As can be seen in FIG. 46, the cable 18410 extends through a corresponding passage 18412 in the proximal joint member 18210 into a corresponding passage 18414 in the distal joint member 18250 and has a retainer lug (not shown) thereon to prevent it from pulling through the distal joint member 18250. The cable 18420 extends through a corresponding passage 18422 in the proximal joint member 18210 and enters a corresponding passage in the distal joint member 18250 and has a retainer lug (not shown) thereon to prevent it from pulling through the distal joint member 18250. The cable 18430 extends through a corresponding passage 18432 in the proximal joint member 18210 into a corresponding passage 18434 in the distal joint member 18250 and has a retainer lug (not shown) thereon to prevent it from pulling through the distal joint member 18250. The cable 18440 extends through a corresponding passage 18442 in the proximal joint member 18210 into a corresponding passage 18444 in the distal joint member 18250 and has a retainer lug (not shown) thereon to prevent it from pulling through the distal joint member 18250. Thus, in one sense, the cables 18410, 18420, 18430, and 18440 span the articulation joint 18200 to apply articulation motions to the distal joint member 18250.

Figure 56:
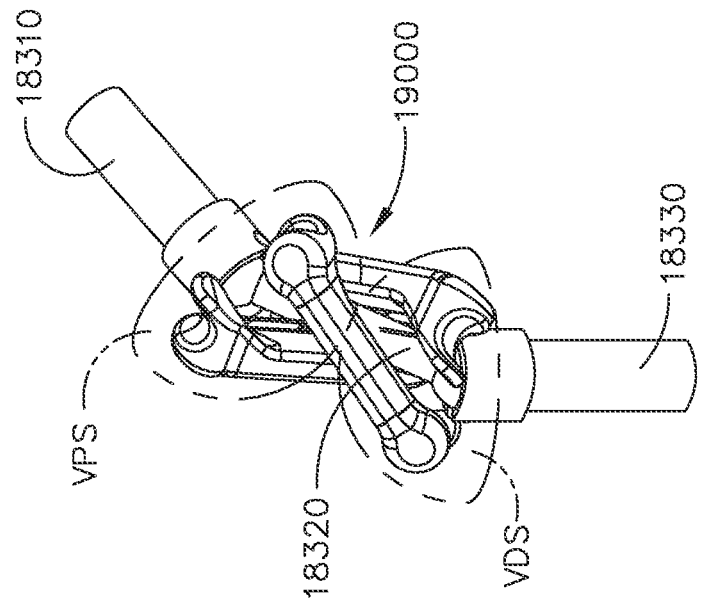
FIG. 56 is another perspective view of the articulation joint of FIG. 55 depicting the virtual spheres in relation to the proximal joint member and distal joint member of the articulation joint of FIG. 46.
Figure 55:
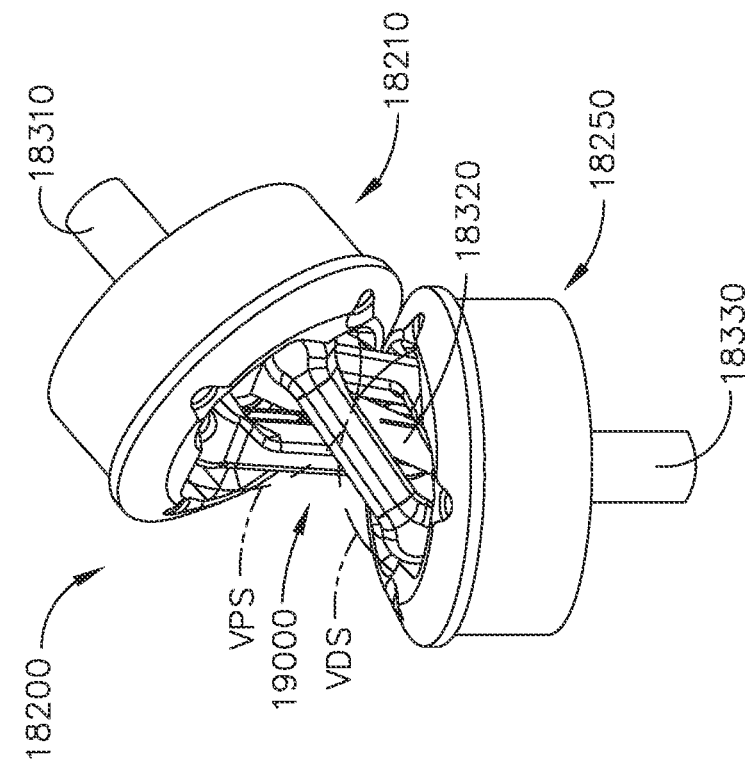
FIG. 55 is another perspective view of the articulation joint of FIG. 46 depicting virtual spheres for illustrating the articulation travel between a proximal portion of the articulation joint relative to a distal portion of the articulation joint.

The distal joint member 18250 is selectively articulatable in multiple directions relative to the proximal joint member 18210 by applying tension to the various cables while enabling the remaining cables to slacken. As can be seen in FIGS. 55 and 56, the link assembly 19000 facilitates articulation motions that essentially approximate a distal virtual sphere VDS that rolls relative to a virtual proximal sphere VPS. In the illustrated arrangement, the rotary drive system 18300 further comprises a central "dog bone" drive shaft 18320 that has a spherical proximal end 18322 that is received in a proximal socket 18312 in the proximal drive shaft 18310 and is movably retained therein by corresponding pins 18324. The central drive shaft 18320 further has a spherical distal end 18326 that is received within a distal socket 18332 in the distal drive shaft 18330 and is movably retained therein by corresponding pins 18328. Other flexible drive shaft arrangements (rotary and/or non-rotary) may also be employed. As can also be seen in FIG. 55, the three links 19010, 19030, and 19050 are configured with a geometry that places the distal end of each link at 180 degrees (about the longitudinal axis) from the proximal end of the link. Each respective link 19010, 19030, and 19050 "reaches around" the central drive shaft 18320. Stated another way, the first link 19010 defines a first link axis FLA. The second link 19030 defines a second link axis SLA and the third link 19050 defines a third link axis TLA. In one arrangement, the links 19010, 19030, and 19050 are supported relative to each other such that the first link axis FLA, the second link axis SLA, and the third think axis TLA are transverse to each other. See FIG. 48. The specific geometric location of the lugs and saddle arrangements define a linkage 19000 that moves the distal joint member 18250 relative to the proximal joint member 18210 as if it was a ball rolling on another ball. The cables hold the links in compression so that the saddles are retained in movable engagement with their corresponding lugs in the proximal joint member 18210 and the distal joint member 18250 without being otherwise directly coupled thereto (e.g., without pins or other arrangements).

Closing an anvil requires a system that meets many requirements. The closure system needs to respond fast to the hand motions of the surgeon who is either operating the robotic system or the hand held system to which the end effector is attached. The closure system must also be capable of applying enough load on the tissue to ensure proper staple formation. It should also be easy to bail out in the event of failure while closing. These features should all be attainable within a footprint that is as small as possible to ensure adequate maneuverability within the patient.

Figure 50:
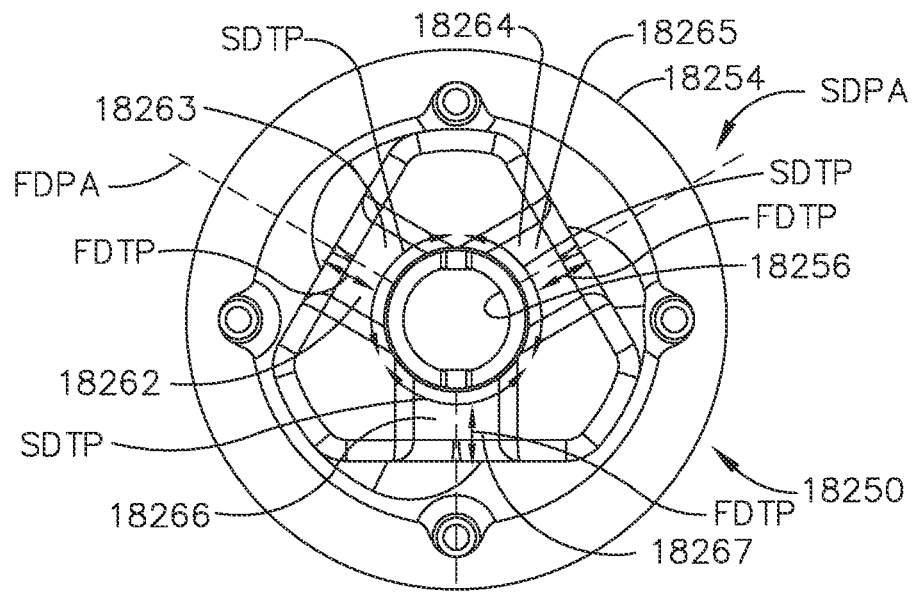
FIG. 50 is an end view of a distal joint member of the articulation joint of FIG. 46.
Figures 53, 54:
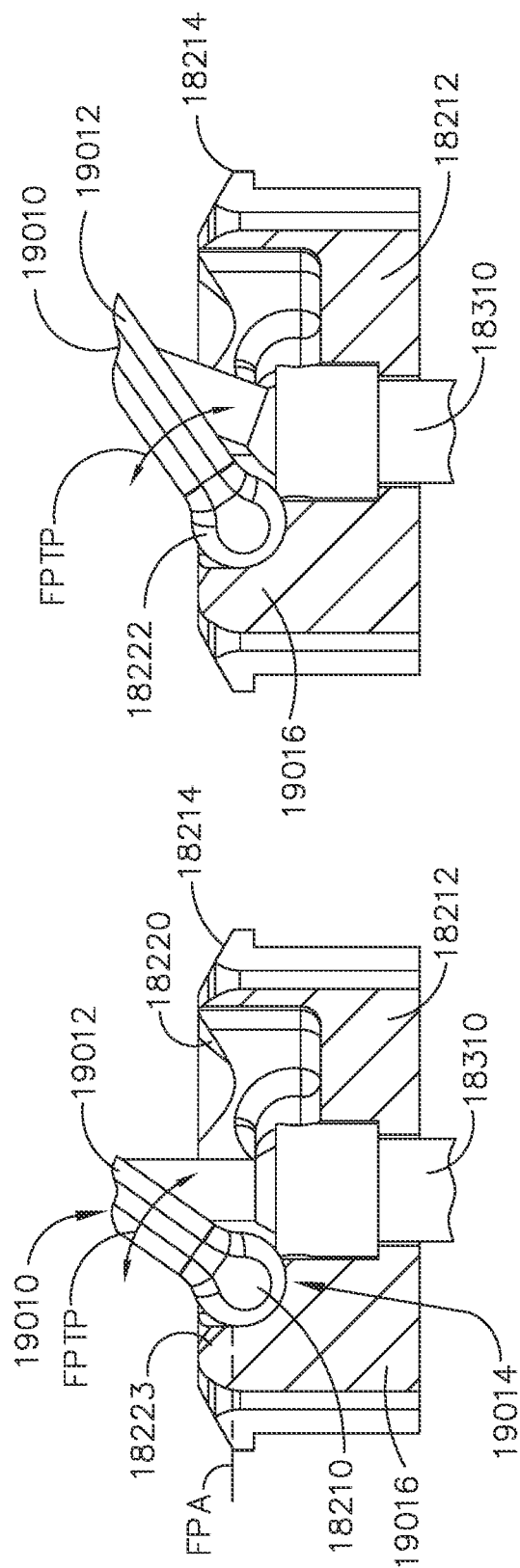
FIG. 53 is another cross-sectional view of the proximal joint member and the first link of FIG. 51.
FIG. 54 is another cross-sectional view of the proximal joint member and first link of FIG. 52.
Figure 57:
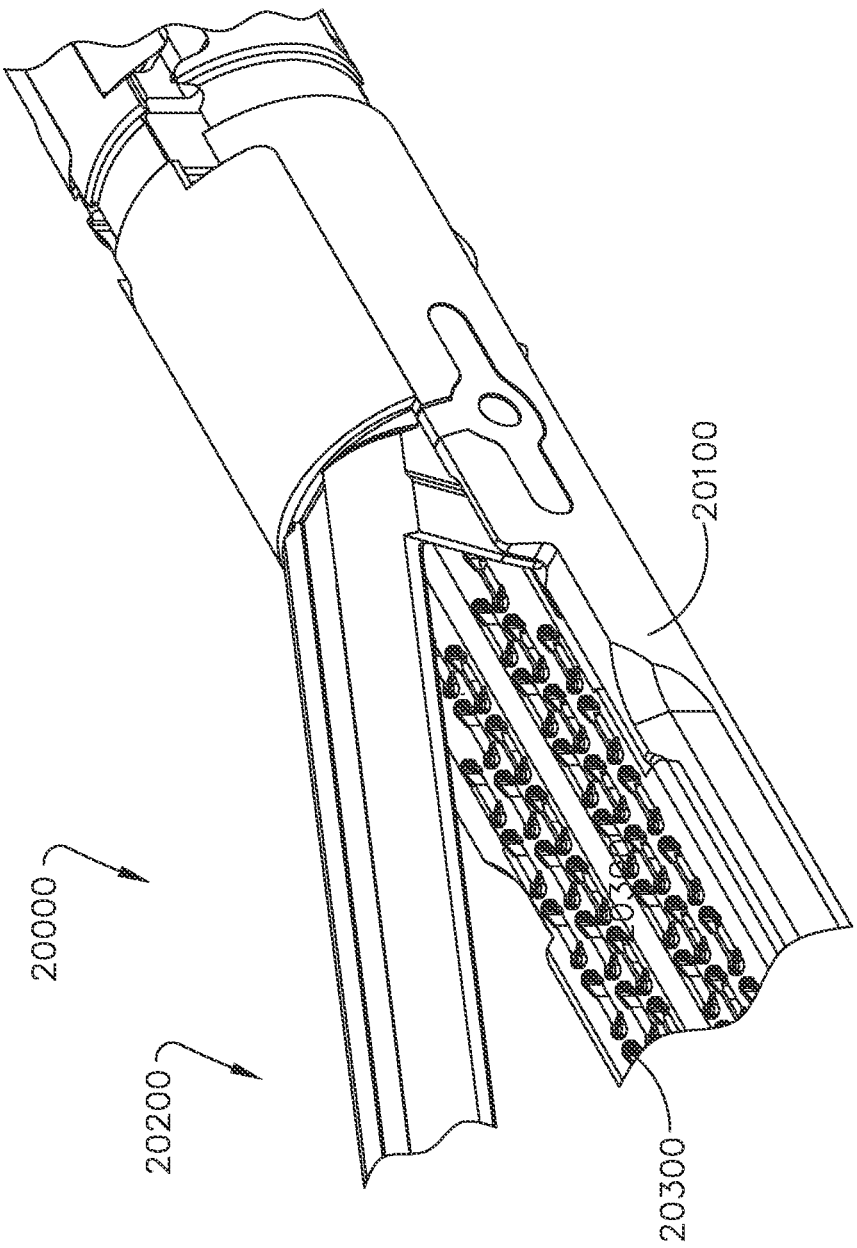
FIG. 57 is a perspective view of a portion of a surgical end effector of a surgical instrument with an anvil thereof in an open position.
Figure 58:
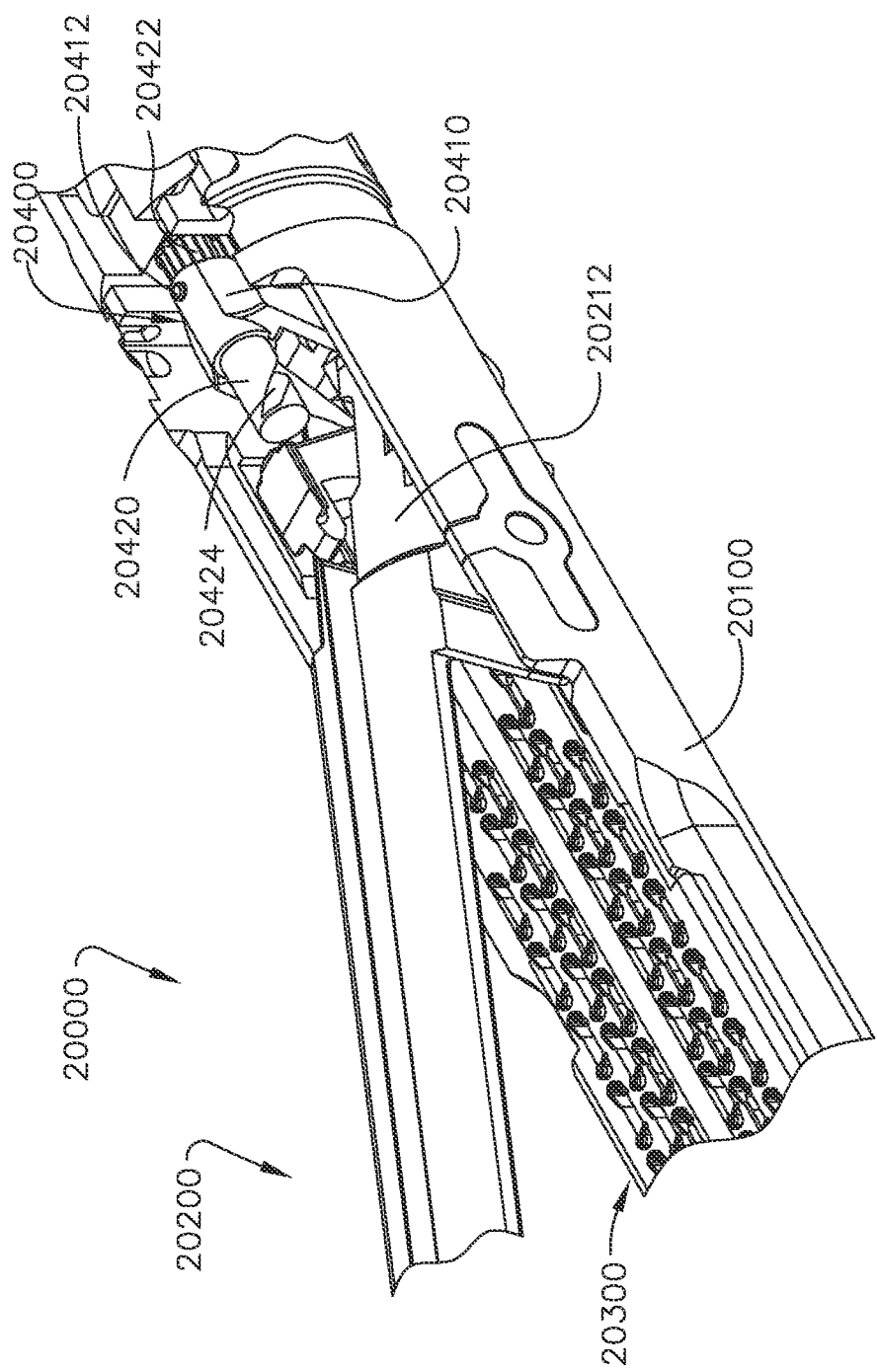
FIG. 58 is another perspective view of the surgical end effector of FIG. 57 with a portion of the surgical end effector omitted to illustrate positions of various closure system components of the surgical instrument.
Figure 60:
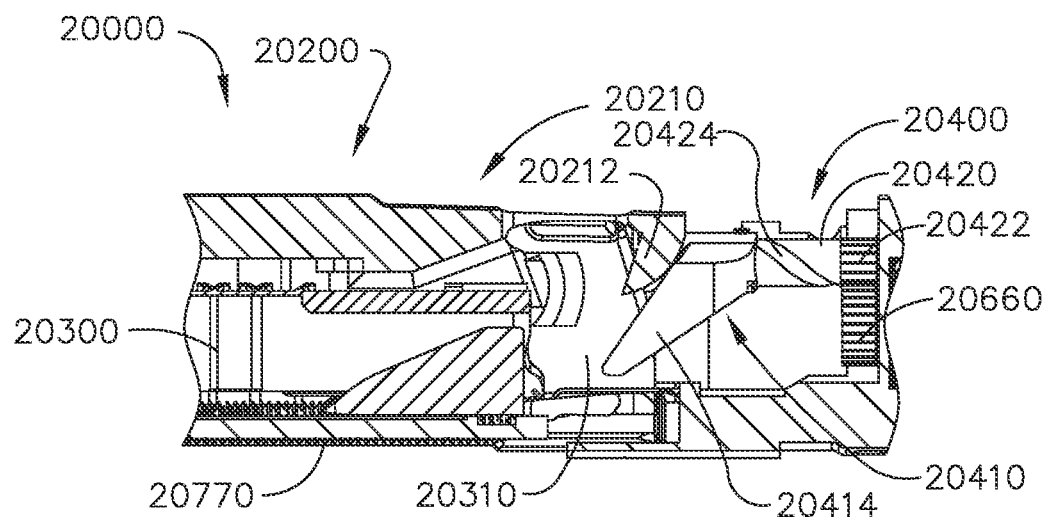
FIG. 60 is another cross-sectional view of the surgical end effector and closure system components of FIG. 58 with the anvil in a closed position.
Figure 59:
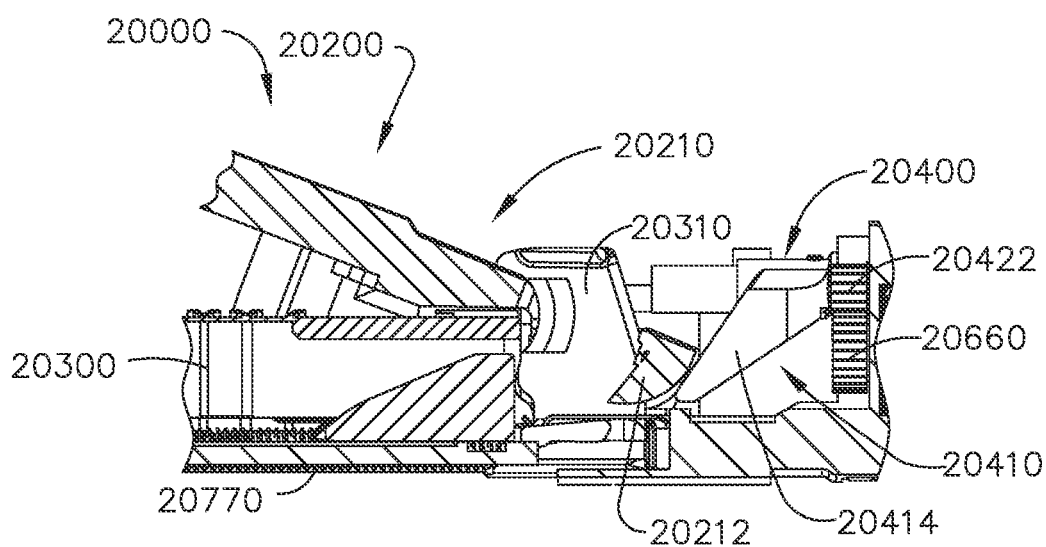
FIG. 59 is a cross-sectional view of the surgical end effector and closure system components of FIG. 58 with the anvil in an open position.

FIGS. 57-59 illustrate a surgical end effector 20000 that comprises a closure system 20400 that may address many if not all of the foregoing challenges. In the illustrated example, the surgical end effector 20000 comprises an elongate channel 20100 that is configured to operably support a surgical staple cartridge 20300 therein. The surgical end effector 20000 further comprises an anvil 20200 that is configured to move between an open position and a closed position relative to the surgical staple cartridge 20300 to clamp tissue therebetween. As can be seen in FIGS. 59 and 60, the closure system 20400 comprises a rotary driven closure cam member 20410 that is configured to apply closure motions to the anvil 20200. In one arrangement, the closure cam member 20410 is supported on a rotatable cam shaft 20420 that has a driven gear 20422 formed thereon. The driven gear 20422 is supported in meshing engagement with a rotary closure gear 20660 that may be driven by a motor/gearbox arrangement supported in a housing of the surgical instrument to which the surgical end effector is operably attached. As can be seen in FIGS. 61 and 62, the cam shaft 20420 comprises a spiral drive groove 20424 that is configured to receive a drive pin 20412 on the closure cam member 20410. Rotation of the cam shaft 20420 in a first rotary direction will cause the closure cam member 20410 to move in the distal direction DD from a starting position (FIGS. 59 and 61) to an ending position (FIGS. 50 and 62).

In one arrangement, the anvil 20200 comprises an anvil mounting portion 20210 that comprises two mounting arms 20212 that each have a slot therein that is configured to receive a corresponding pivot pin 20216 that protrudes from a proximal end of the elongate channel 20100. See FIG. 58. The closure cam member 20410 further comprises two closure cams 20414 that correspond to the anvil mounting arms 20212 of the anvil 20200. In one arrangement, the anvil 20200 may be biased into the open position shown in FIGS. 58 and 59 by a spring (not shown). The anvil 20200 is moved to a closed position by actuating the rotary closure gear 20660 to drive the closure cam member 20410 distally from the starting position to the ending position. As the closure cam member 20410 is driven distally, the closure cams 20414 contact the corresponding mounting arms 20212 and causes the anvil 20200 to pivot to the closed position shown in FIG. 60.

Figure 63:
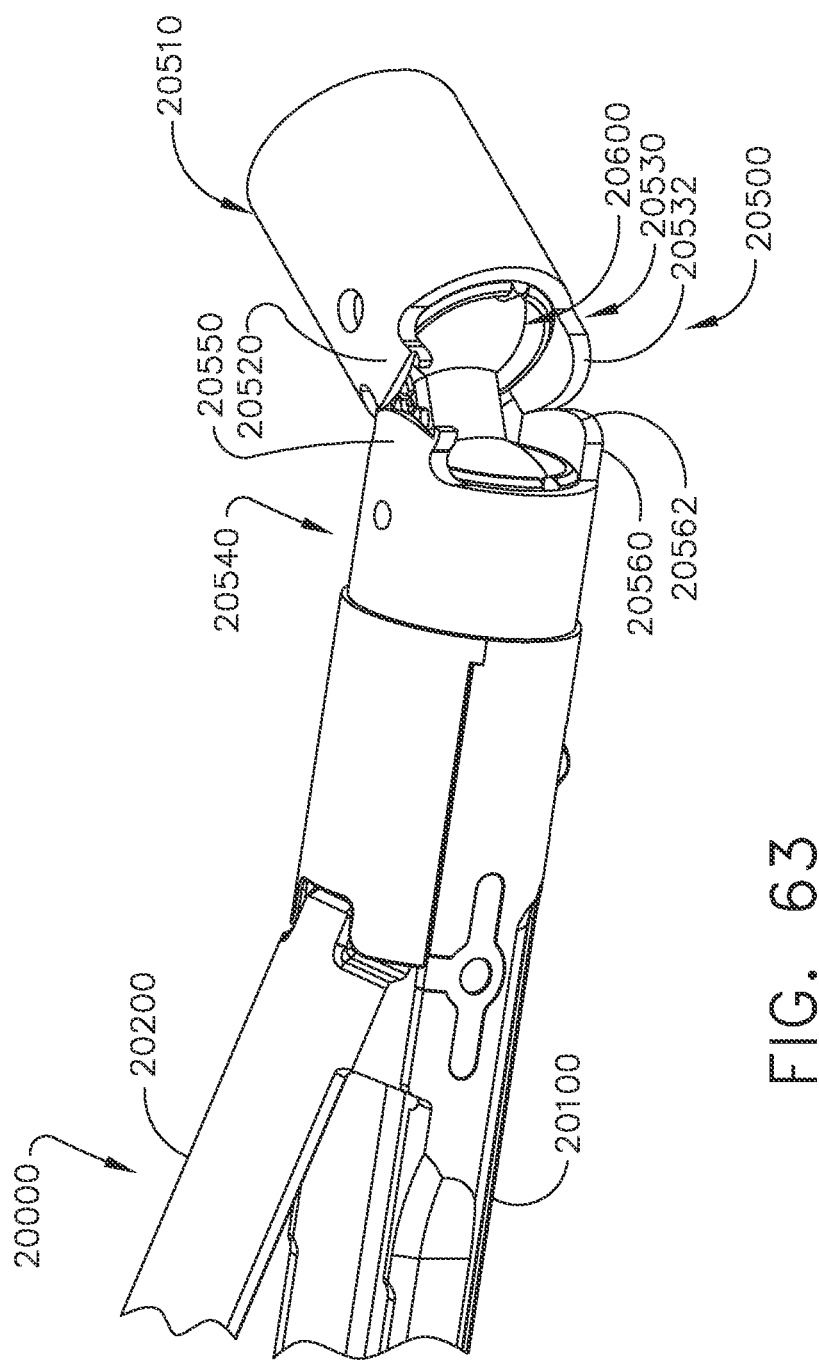
FIG. 63 is another perspective view of the surgical end effector of FIG. 57 oriented in an articulated orientation about an articulation joint that is attached thereto.

FIG. 63 illustrates the surgical end effector 20000 attached to an articulation joint 20500 that employs a rotary drive assembly 20600 for transmitting rotary drive motions across the articulation joint 20500. In the illustrated example, the rotary drive assembly 20600 comprises nested universal joints that can permit the surgical end effector 20000 to roll distal to the articulation joint 20500. A two-side joint arrangement wherein each joint can angle approximately seventy degrees (one hundred forty degrees total) may be employed, for example.

Figure 64:
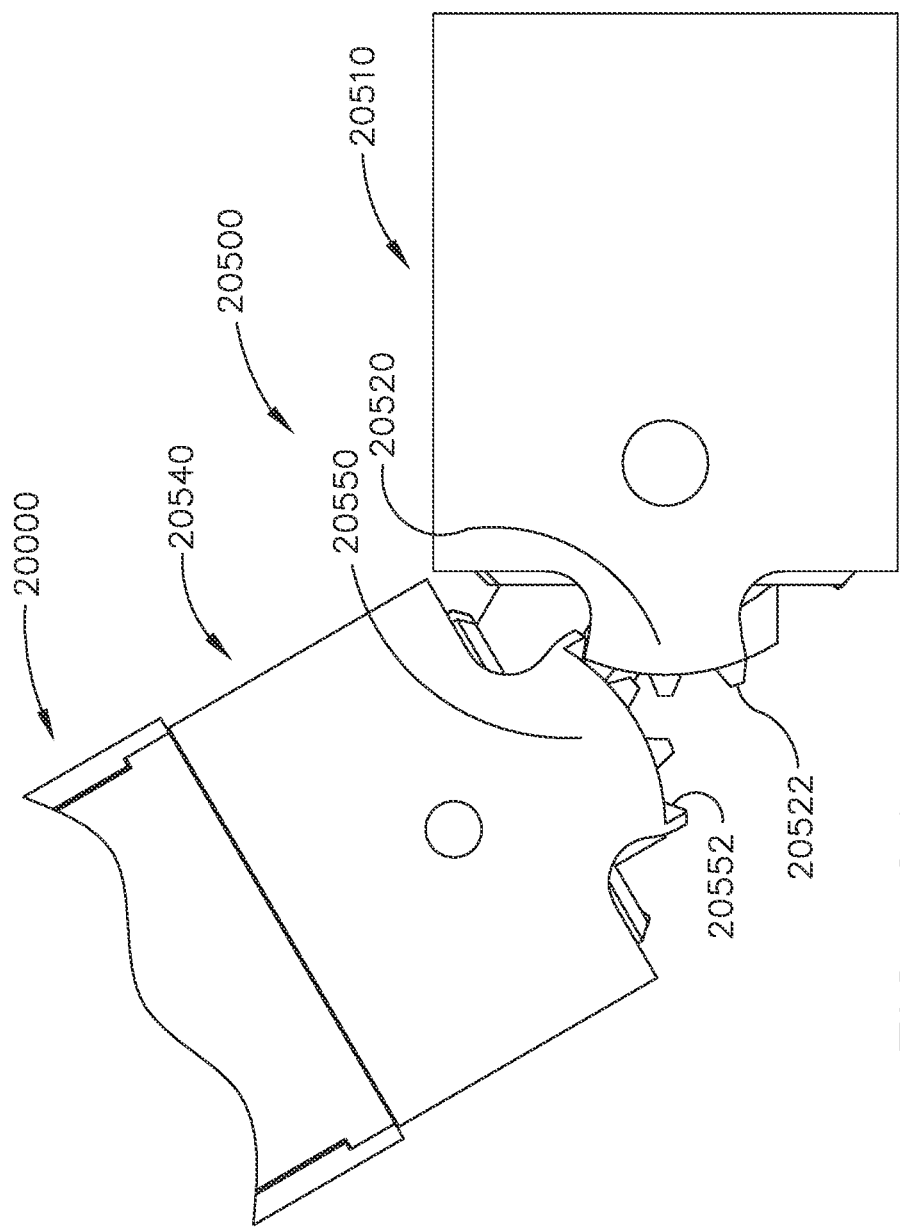
FIG. 64 is a top view of a distal joint portion of the articulation joint of FIG. 63 articulated relative to a proximal articulation joint portion of the articulation joint of FIG. 63.
Figure 65:
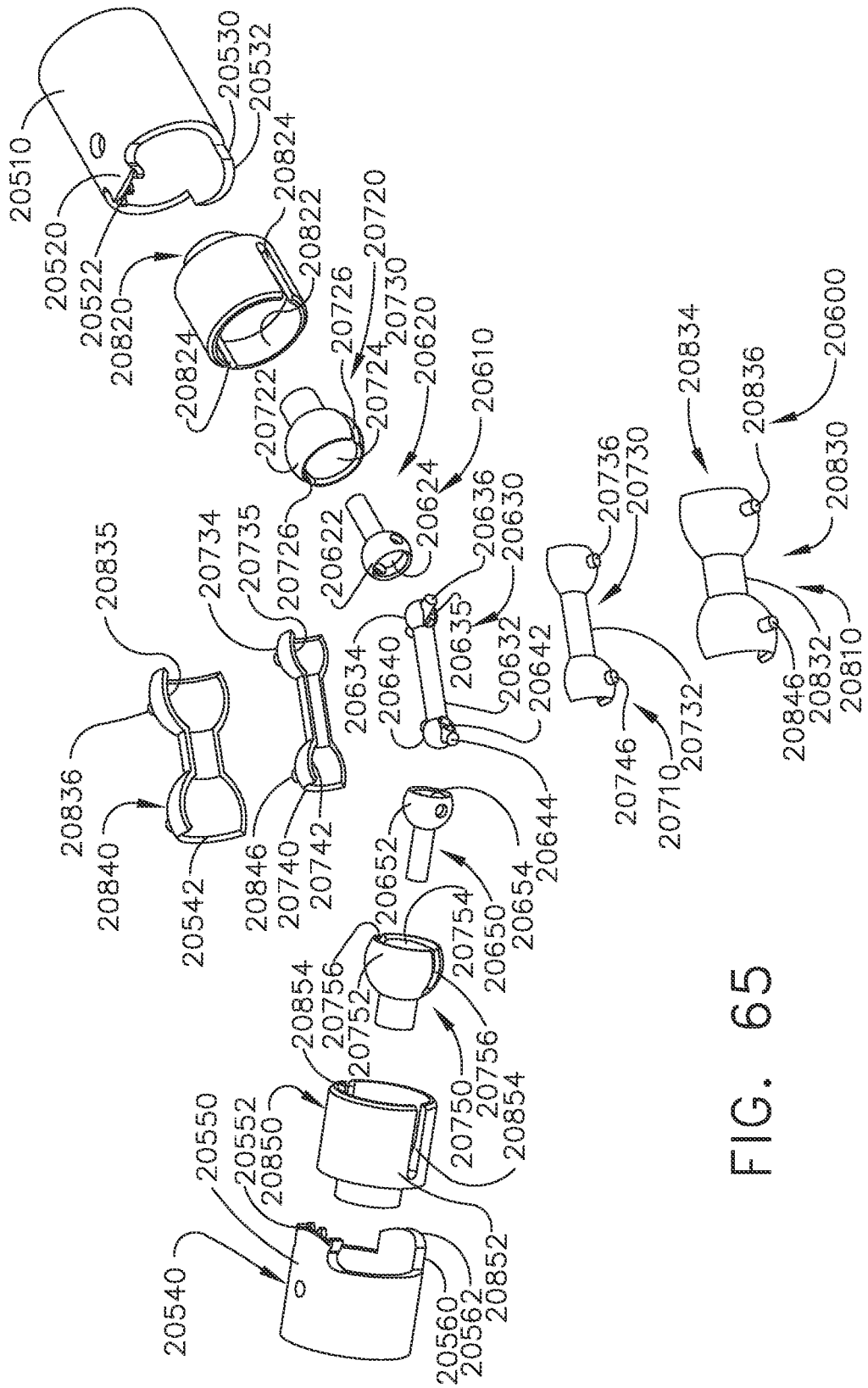
FIG. 65 is an exploded assembly view of the articulation joint of FIG. 63 and a rotary drive assembly.

In one arrangement, the articulation joint 20500 comprises a proximal joint member 20510 that may be attached to an outer tube member of an elongate shaft assembly that is coupled to or operably interfaces with a housing of a surgical instrument. In alternative arrangements, the proximal joint member 20510 may be integrally formed on a distal end of the outer tube member of the elongate shaft. As can be seen in FIGS. 63-65, the proximal joint member 20510 comprises a distally protruding upper pivot tang 20520 and a distally protruding lower pivot tang 20530. The articulation joint 20500 further comprises a distal joint member 20540 that is attached to the surgical end effector 20000. In one example, the distal joint member 20540 is attached to the proximal end of the elongate channel 20100 and includes a proximally protruding upper pivot tang 20550 and a proximally protruding lower pivot tang 20560. In the illustrated example, the distally protruding upper pivot tang 20520 is formed with a series of proximal articulation gear teeth 20522 and the proximally protruding upper pivot tang 20550 is formed with a series of distal articulation gear teeth 20552. The distally protruding lower pivot tang 20530 is formed with an arcuate proximal surface 20532 and the proximally protruding lower pivot tang 20560 is formed with an arcuate distal surface 20562. In one example, the rotary drive assembly 20600 extends through the articulation joint 20500 and serves to retain the proximal articulation gear teeth 20522 in meshing engagement with the distal articulation gear teeth 20552 to facilitate pivotal travel therebetween. In addition, in at least one arrangement, the arcuate distal surface 20562 and the arcuate proximal surface 20532 may be supported in rocking engagement with each other. Such arrangement permits the surgical end effector 20000 to articulate through a single articulation plane relative to the elongate shaft assembly upon application of articulation control motions to the surgical end effector 20000. Such articulation control motions may be applied to the surgical end effector by cables or other articulation members (not shown) that extend from control systems in the surgical instrument housing and span the articulation joint 20500 to operably interface with the surgical end effector.

Turning to FIG. 65, the rotary drive system 20600 comprises a series of nested shaft systems 20610, 20710, and 20810. As can be seen in FIG. 65, the centermost "first" shaft system 20610 comprises a first proximal shaft member 20620 that is attached to or otherwise operably interfaces with a corresponding first rotary drive system supported by the housing of the surgical instrument. For example, the first rotary drive system may comprise a corresponding motor/gear arrangement configured to rotate the first proximal shaft member 20620. The first shaft system 20610 further comprises a first central shaft 20630 that comprises a shaft body 20632 that has a first spherical proximal end 20634 that is rotatably supported in a first spherical proximal cup 20622 on the first proximal shaft member 20620. The first central shaft 20630 is movably pinned within a cavity 20624 in the first spherical proximal cup 20622 by a first proximal pin 20636 that extends through an arcuate slot 20635 in the first spherical proximal end 20634. The first central shaft 20630 further comprises a first spherical distal end 20640 that is rotatably supported in a first spherical distal cup 20652 that is attached to a first distal shaft member 20650. The first central shaft 20630 is movably pinned within a cavity 20654 in the first spherical distal cup 20652 by a first distal pin 20644 that extends through an arcuate slot 20642 in the first spherical distal end 20640. In one arrangement, for example, the first distal shaft member 20650 may be configured to apply rotary motions to the closure gear 20660 to apply rotary closure motions to the rotatable cam shaft 20420 in the manners described above. See FIGS. 59 and 60, for example. Thus, in at least one arrangement, actuation of the first rotary drive system to cause rotation of the first proximal shaft member 20620 will result in actuation of the closure system 20400 to move the anvil 20200 from an open position to a closed position.

Figure 66:
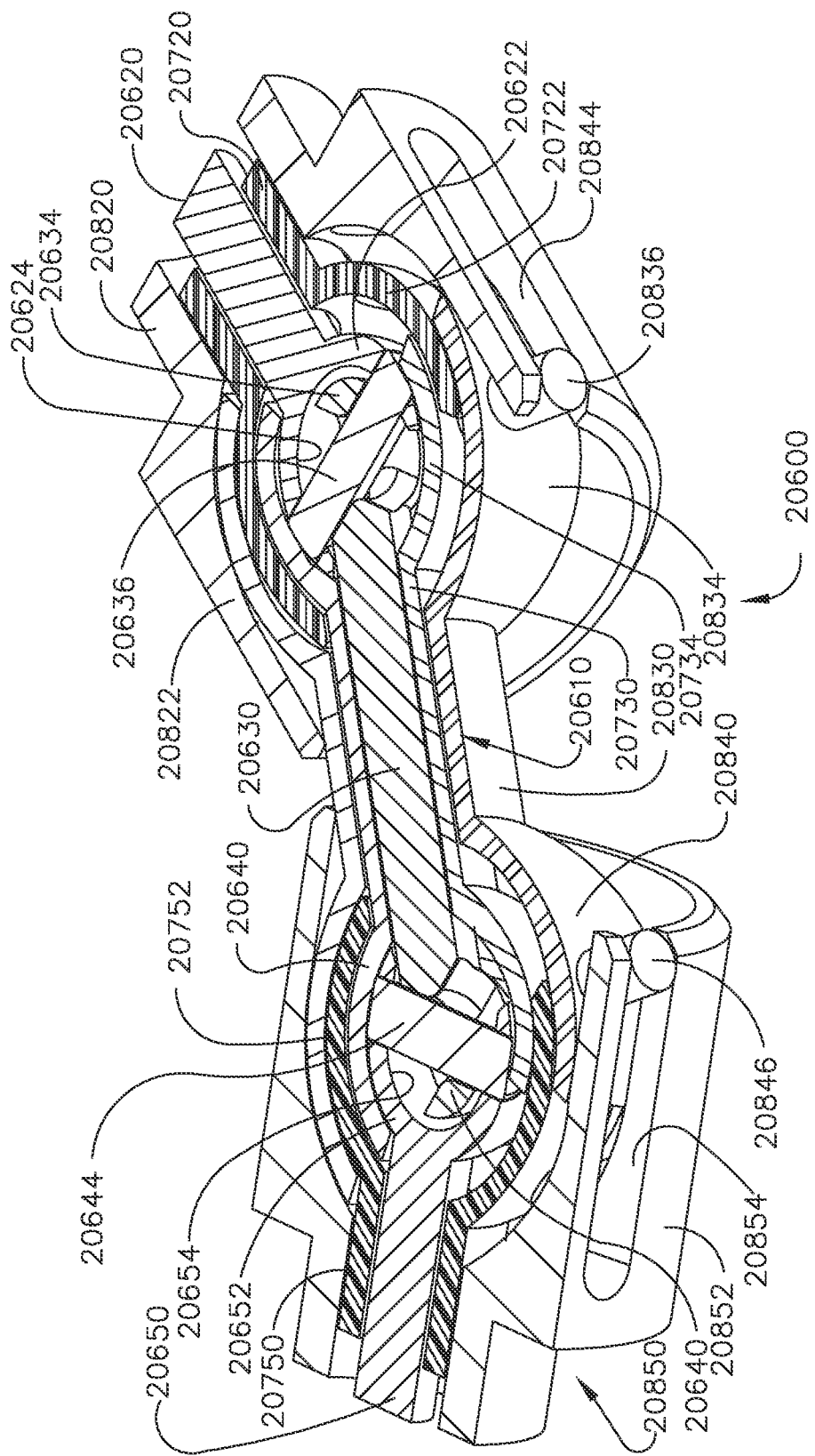
FIG. 66 is a cross-sectional view of the rotary drive assembly of FIG. 65.
Figure 67:
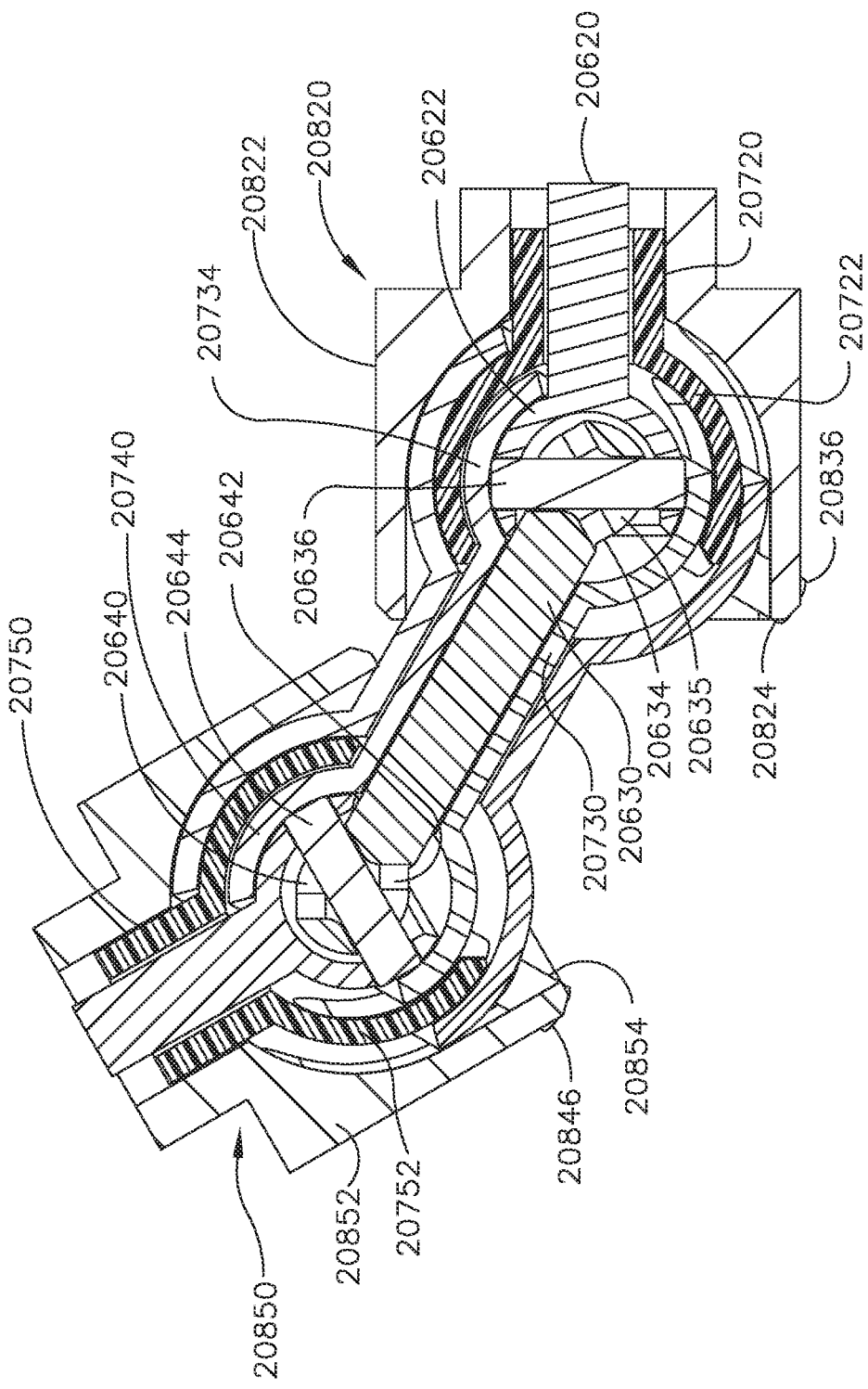
FIG. 67 is another cross-sectional view of the rotary drive assembly of FIG. 66.

Referring to FIGS. 65-67, the second shaft system 20710 comprises a second proximal shaft member 20720 that is attached to or otherwise operably interfaces with a corresponding second rotary drive system supported by the housing of the surgical instrument. For example, the second rotary drive system may comprise a corresponding motor/gear arrangement configured to rotate the second proximal shaft member 20720. The second shaft system 20710 further comprises a second hollow central shaft 20730 that comprises a hollow shaft body 20732 that has a second spherical proximal end 20734. In one arrangement, the second hollow central shaft 20730 may be fabricated in two segments that are welded or otherwise coupled together. The second spherical proximal end 20734 defines a second central proximal cavity 20735 that is configured to movably receive therein the first spherical proximal cup 20622 of the first proximal shaft member 20620 therein. The second spherical proximal end 20734 is configured to be rotatably supported in a second spherical proximal cup 20722 on the second proximal shaft member 20720. The second hollow central shaft 20730 is movably pinned within a cavity 20724 in the second spherical proximal cup 20722 by second proximal pin segments 20736 that extend from the second spherical proximal end 20734 to be movably received within corresponding arcuate slots 20726 in the second spherical proximal cup 20722 on the second proximal shaft member 20720. The second hollow central shaft 20730 further comprises a second spherical distal end 20740. The second spherical distal end 20740 defines a second central distal cavity 20742 that is configured to movably receive therein the first spherical distal cup 20652 of the first distal shaft member 20650 therein. The second hollow central shaft 20730 is movably pinned within a cavity 20754 in the second spherical distal cup 20752 by second distal pin segments 20746 that extend from the second spherical distal end 20740 to be movably received within corresponding arcuate slots 20756 in the second spherical distal cup 20752 on the second distal shaft member 20750.

Figure 68:
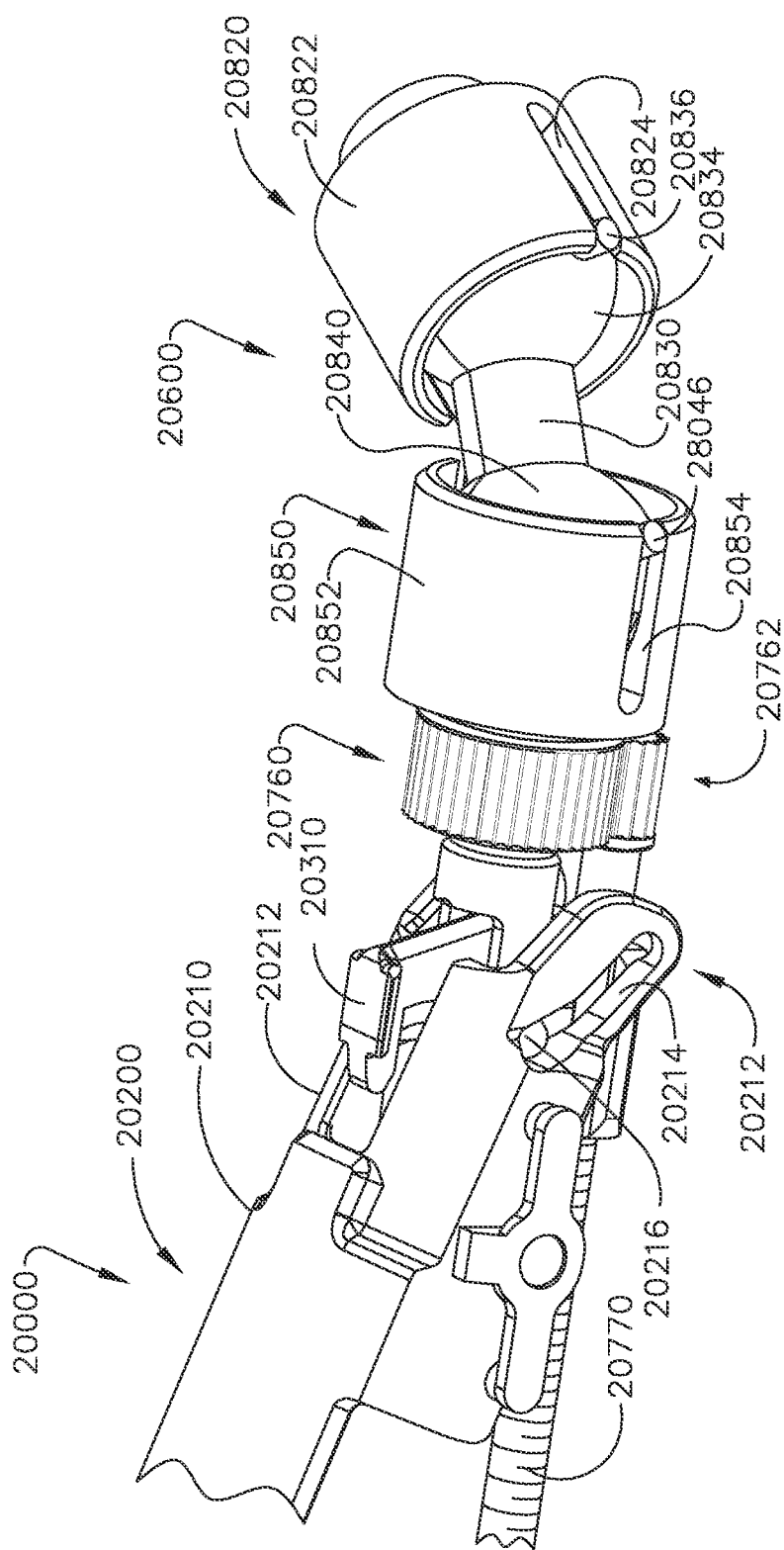
FIG. 68 is another perspective view of the surgical end effector and articulation joint of FIG. 63 with portions thereof omitted for clarity.

In one arrangement, the second distal shaft member 20750 may be configured to apply rotary motions to a first rotary drive gear 20760 that is in meshing engagement with a driven gear 20762 that is attached to a rotary drive shaft 20770 that is rotatably supported in the elongate channel 20100. See FIGS. 59, 60, and 68. As can be seen in FIGS. 59, 60, and 68, the surgical end effector 20000 further comprises a firing member 20310 that is in threaded engagement with the rotary drive shaft 20770. Rotation of the rotary drive shaft 20770 in a first rotary direction will cause the firing member 20310 to move distally from a starting position (FIG. 59) through the surgical end effector 20000 to an ending position. Rotation of the rotary drive shaft 20770 in an opposite rotary motion will drive the firing member 20310 from the ending position back to the starting position. Thus, in at least one arrangement, actuation of the second rotary drive system to cause rotation of the second proximal shaft member 20720 will result in actuation of the firing member 20310 to cut and staple tissue that is clamped between the anvil 20200 and the surgical staple cartridge 20300.

Referring to FIGS. 65-67, the third shaft system 20810 comprises a third proximal shaft member 20820 that is attached to or otherwise operably interfaces with a corresponding third rotary drive system supported by the housing of the surgical instrument. For example, the third rotary drive system may comprise a corresponding motor/gear arrangement configured to rotate the third proximal shaft member 20820. The third shaft system 20810 further comprises a third hollow central shaft 20830 that comprises a hollow shaft body 20832 that has a third spherical proximal end 20834. In one arrangement, the third hollow central shaft 20830 may be fabricated in two segments that are welded or otherwise coupled together. The third spherical proximal end 20834 defines a third proximal cavity 20835 that is configured to movably receive therein the second spherical proximal cup 20722 of the second proximal shaft member 20720 therein. The third spherical proximal end 20834 is configured to be movably supported in a third proximal socket 20824 in the third proximal shaft member 20820. The third spherical proximal end 20834 is axially movable within the third proximal socket 20824 and is attached thereto by third proximal pin segments 20836 that extend from the third spherical proximal end 20834 to be movably received within corresponding axial slots 20824 in the third proximal socket 20824 on the third proximal shaft member 20820. The third central shaft 20830 further comprises a third spherical distal end 20840. The third spherical distal end 20840 defines a third central distal cavity 20842 that is configured to movably receive therein the second spherical distal cup 20752 of the second distal shaft member 20750 therein. The third spherical distal end 20840 is movably pinned within a third distal socket 20852 on a third distal shaft 20850. The third spherical distal end 20840 is axially movable within the third distal socket 20852 and is attached thereto by third distal pin segments 20846 that extend from the third spherical distal end 20840 to be movably received within corresponding axial slots 20854 in the third distal socket 20850.

In one arrangement, the third distal shaft member 20850 may be configured to apply rotary motions to the surgical end effector 20000 to rotate the surgical end effector 20000 about the shaft axis SA. In one arrangement, for example, the third distal shaft member 20850 may be directly attached to (welded) the elongate channel 20100. Thus, in at least one arrangement, actuation of the third rotary drive system to cause rotation of the third proximal shaft member 20820 will result in rotation of the third distal shaft member 20850 and the surgical end effector 20000. In the illustrated arrangement, the intermeshing gear teeth 20522 and 20552 on the upper proximal pivot tang 20520 and upper distal pivot tang 20550 force the centers of the shaft systems to stay in the same center distance when undergoing articulation. Such shaft systems are very strong and robust while maintaining a tight articulation joint while also facilitating distal roll of the surgical end effector.

Figure 69:
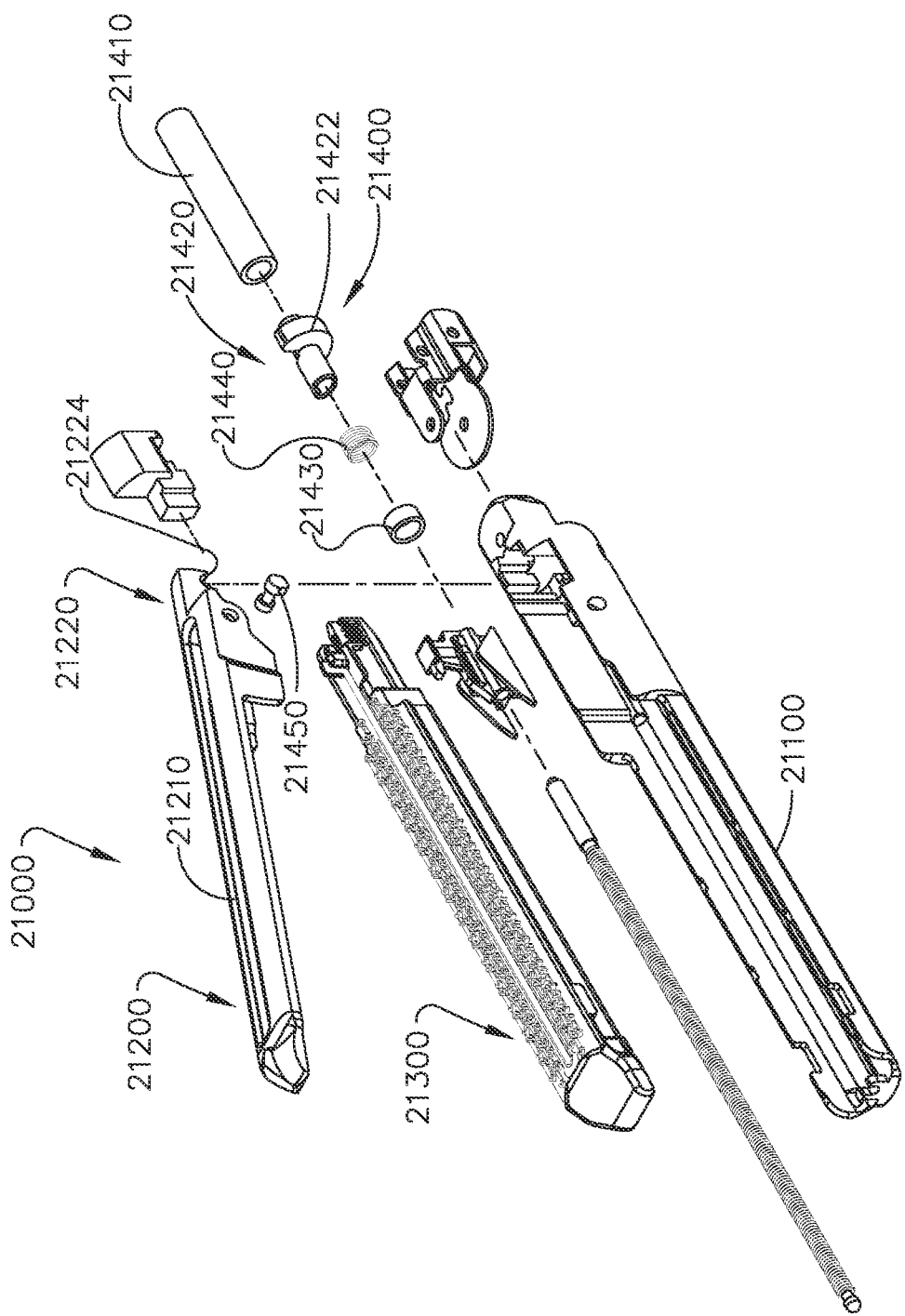
FIG. 69 is an exploded assembly view of another surgical end effector and rotary driven closure system.

Highly articulated robotic and handheld endo mechanical staplers need to generate a lot of force to clamp onto thick tissue. Moving forces through a highly articulated joint (sixty degrees and greater for example) is challenging. Many robotic and handheld motors are slow and their ability to produce sufficient torque is limited. FIGS. 69-75 illustrate a surgical end effector 21000 that can address many of not all of those challenges. As can be seen in FIG. 69, the surgical end effector 21000 comprises a first jaw 21100 that comprises an elongate channel 21110 that is configured to operably support a surgical staple cartridge 21300 therein. The surgical end effector 21000 further comprises a second jaw 21200 that comprises an anvil 21210 that is pivotally coupled to the elongate channel 21110 about a fixed pivot axis PA. The anvil 21210 is pivotable between an open position (FIG. 71) and a closed position (FIG. 70) by a rotary driven closure system 21400.

Figure 70:
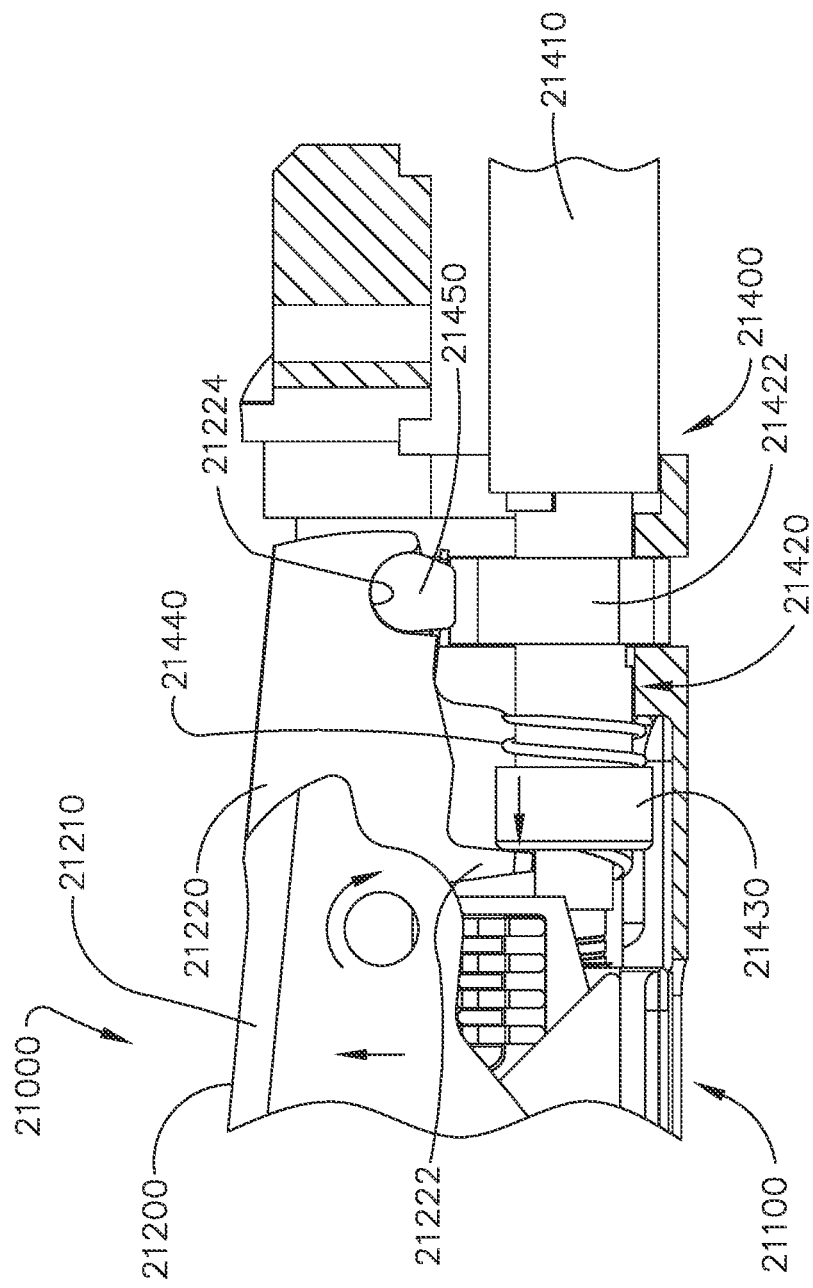
FIG. 70 is a partial side view of a portion of the surgical end effector and rotary drive closure system of FIG. 69 with the anvil in a closed orientation.
Figure 71:
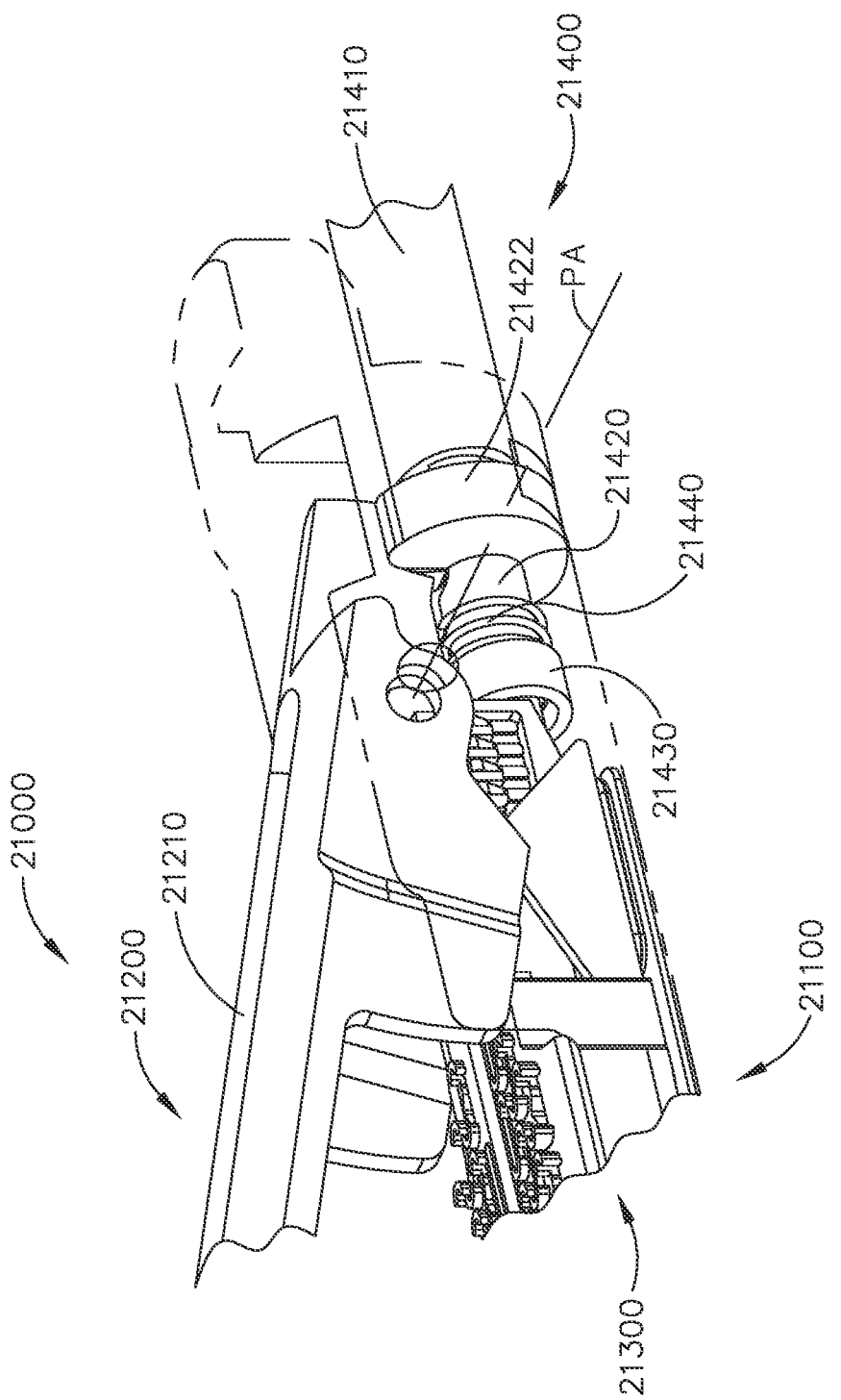
FIG. 71 is a partial perspective view of a portion of the surgical end effector and rotary drive system of FIG. 69 with the anvil in an open orientation.

In one arrangement, the closure system 21400 comprises a closure drive shaft 21410 that is configured to be rotated by a corresponding source of rotary motion (motor, etc.) in the housing of the surgical instrument to which the surgical end effector is attached. The closure drive shaft 21410 may comprises a flexible shaft arrangement that can flex while transferring torque through an articulation joint. The closure drive shaft 21410 is attached to a rotary cam shaft 21420 that has a closure cam lobe 21422 formed thereon. In one arrangement, an opening bushing 21430 is movably journaled on the rotary cam shaft 21420 and is configured to engage an opening tab 21222 on an anvil mounting portion 21220 of the anvil 21210. An opening spring 21440 is positioned on the rotary cam shaft 21420 to bias the opening bushing 21430 distally into contact with the opening tab 21222 on the anvil 21210. As can be seen in FIG. 70, as the opening bushing 21430 moves distally, it contacts the opening tab 21222 which causes the anvil 21210 to pivot about the pivot axis PA to the open position (FIG. 71).

Figure 75:
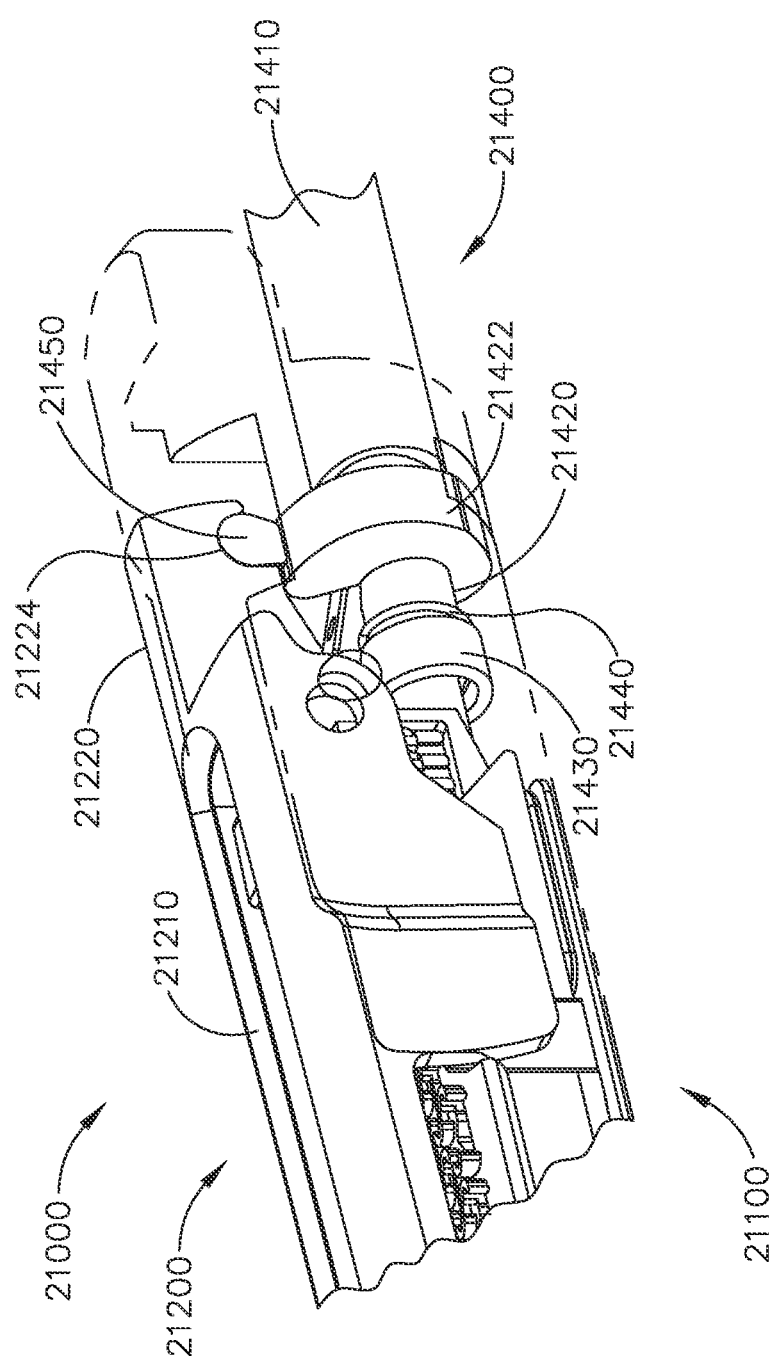
FIG. 75 is another perspective view of a portion of the surgical end effector and rotary drive system of FIG. 69 with the anvil in a closed position.

In one example, the anvil 21210 is pivoted from the open position to a closed position by rotating the rotary cam shaft 21420 from a first rotary position shown in FIG. 72 to a final rotary position shown in FIG. 74. As can be seen in FIGS. 69 and 70, the closure system 21400 further comprises a cam follower 21450 that is movably supported in the anvil mounting portion 21220 and is configured for movable engagement with the closure cam lobe 21422 on the rotary cam shaft 21420. FIGS. 71 and 72 illustrate the position of the closure cam lobe 21422 when the anvil 21210 is in the open position. When in that position, the anvil mounting portion 21220 has pivoted past the closure cam lobe 21422 such that the cam follower 21450 is not contacted by the closure cam lobe 21422. As the rotary cam shaft 21420 begins to rotate, the closure can lobe 21422 contacts the cam follower 21450 (FIG. 73) and cams the cam follower 21450 into contact with a pivot cradle 12224 in the anvil mounting portion 21220 (upward in FIG. 73) to the position shown in FIG. 74 wherein the cam follower 21452 has pivoted the anvil 21210 to the closed position (FIG. 75). As the anvil 21210 pivots to the closed position, the opening tab 21222 biases the opening bushing 21430 proximally on the rotary cam shaft 21420 against the bias of the opening spring 21440. Thus, when the rotary cam shaft 21420 is rotated in an opposite direction, the anvil opening spring 21440 biases the opening bushing 21430 distally into contact with the opening tab 21222 to pivot the anvil 21210 back to the open position.

Figure 76:
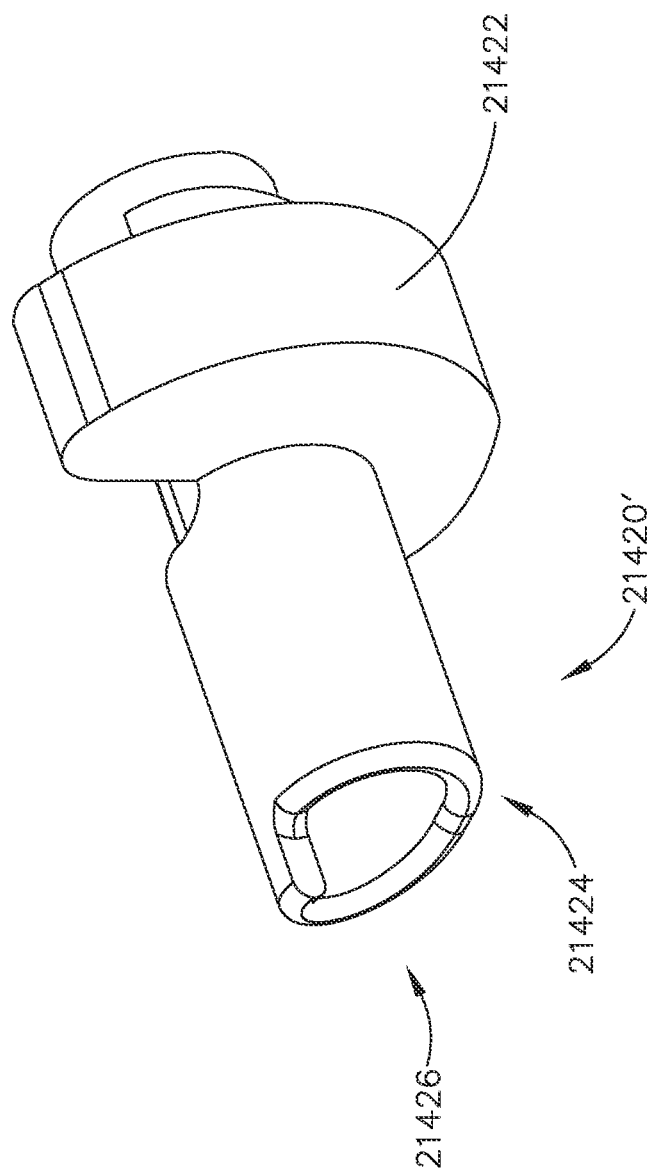
FIG. 76 is a perspective view of another rotary cam shaft.
Figure 77:
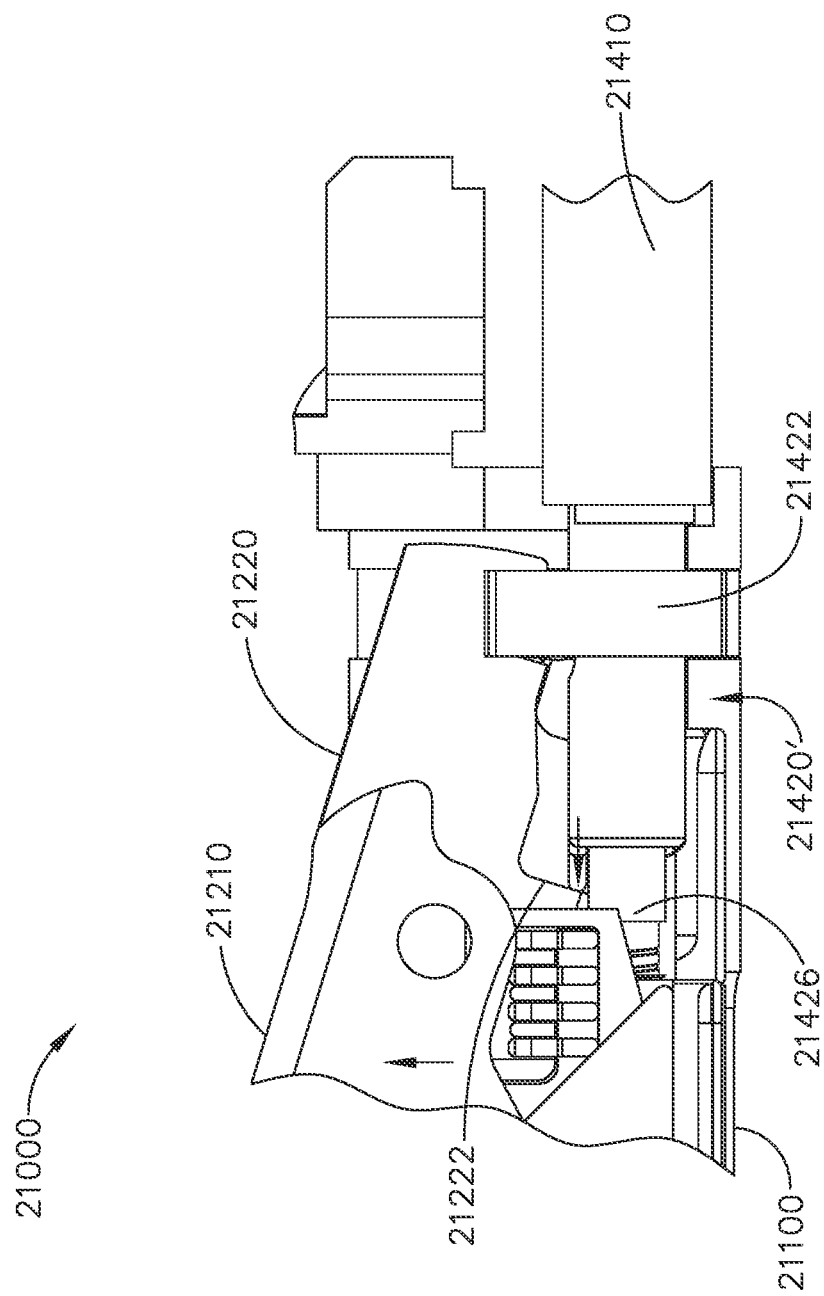
FIG. 77 is a partial side elevational view of a portion of the surgical end effector and rotary drive system of FIG. 69 employing the rotary cam shaft of FIG. 76 and with the anvil in an open position.

FIG. 76 illustrates another rotary cam shaft 21420' that is identical to the rotary cam shaft 21420 except that a distal end 21426 of the rotary cam shaft 21420' further comprises an opening cam 21426 that is configured to engage the opening tab 21222 on the anvil 21210 to move the anvil 21210 to an open position. Thus, when the rotary cam shaft 21420' is in a first rotary position, the opening cam 21426 has cammed the anvil opening tab 21222 to pivot the anvil 21210 to the open position. See FIG. 77. To close the anvil, the rotary cam shaft 21420' is rotated in a closure direction to cause the cam lobe 21422 to cam the cam follower 21450 upward to pivot the anvil 21210 into the closed position. The anvil 21210 can then be returned to the open position by rotating the rotary cam shaft 21420' back to the first rotary position. In alternative arrangements, the opening bushing 21430 and opening spring 21440 may be used in conjunction with the rotary cam shaft 21420'.

It will be appreciated that the foregoing embodiments of the closure system 21400 facilitates the application of relatively quick closure and opening motions to the anvil 21210. In various arrangements, the cam profile(s) may be formed to establish a low mechanical advantage at the start and a relatively high mechanical advantage at the end when the anvil 21210 starts to compress tissue. Such closure system arrangement employs fewer components than many other closure system designs. This arrangement also provides additional space at the proximal end of the end effector to accommodate electronics and other mechanisms in the end effector.

Example 1—A surgical instrument comprising a shaft assembly that defines a shaft axis. The surgical instrument further comprises a surgical end effector that defines an end effector axis and is coupled to the shaft assembly by an articulation joint that is configured to facilitate articulation of the surgical end effector relative to the shaft assembly in an articulation plane between an unarticulated position wherein the end effector axis is axially aligned with the shaft axis and articulated positions wherein the end effector axis is not axially aligned with the shaft axis. The articulation joint comprises a proximal joint member that is coupled to the shaft assembly and a distal joint member that is coupled to the surgical end effector. The articulation joint further comprises an articulation linkage assembly that comprising a plurality of links. Each link is configured to operably interface with the proximal joint member for movable travel relative thereto in a first proximal travel path and a second proximal travel path that is transverse to the first proximal travel path. Each link is further configured to operably interface with the distal joint member for movable travel relative thereto in a first distal travel path and a second distal travel path that is transverse to the first distal travel path. The articulation linkage assembly defines a central passage that extends between the plurality of links. The surgical instrument further comprises a drive member that extends through the proximal joint member, the central passage and the distal joint member to operably interface with the surgical end effector. At least two flexible actuator members span the articulation joint and operably interface with the distal joint member to apply articulation motions thereto.

Example 2—The surgical instrument of Example 1, wherein the plurality of links comprises three links.

Example 3—The surgical instrument of Example 2, wherein the three links comprises a first link that is configured to operably interface with the proximal joint member for movable travel relative thereto in a first proximal travel path and another first proximal travel path that is transverse to the first proximal travel path. The first link is further configured to operably interface with the distal joint member for movable travel relative thereto in a first distal travel path and another first distal travel path that is transverse to the first distal travel path. The three links further comprise a second link that is configured to operably interface with the proximal joint member for movable travel relative thereto in a second proximal travel path and another second proximal travel path that is transverse to the second proximal travel path. The second link is configured to operably interface with the distal joint member for movable travel relative thereto in a second distal travel path and another second distal travel path that is transverse to the second distal travel path. The three links further comprise a third link that is configured to operably interface with the proximal joint member for movable travel relative thereto in a third proximal travel path and another third travel path that is transverse to the third proximal travel path. The third link is further configured to operably interface with the distal joint member for movable travel relative thereto in a third distal travel path and another third distal travel path that is transverse to the third distal travel path.

Example 4—The surgical instrument of Examples 1, 2 or 3, wherein each link comprises a proximal saddle that is configured to movably interface with a corresponding proximal mounting lug on the proximal joint member and a distal saddle that is configured to movably interface with a corresponding distal mounting lug on the distal joint member.

Example 5—The surgical instrument of Example 4, wherein each proximal mounting lug defines an arcuate proximal pivot surface. Each proximal saddle comprises a U-shaped proximal pivot surface that is configured to movably interface with the arcuate proximal pivot surface on the proximal mounting lug to facilitate travel of the link in the first proximal travel path and the second proximal travel path on the proximal mounting lug. Each distal mounting lug defines an arcuate distal pivot surface. Each distal saddle comprises a U-shaped distal pivot surface that is configured to movably interface with the arcuate distal pivot surface on the distal mounting lug to facilitate travel of the link in the first distal travel path and the second distal travel path on the distal mounting lug.

Example 6—The surgical instrument of Example 5, wherein each proximal mounting lug defines a proximal lug axis and wherein the first proximal travel path comprises a first arcuate proximal travel path along the proximal lug axis. The second proximal travel path comprises a second arcuate proximal travel path around the proximal lug axis. Each distal mounting lug defines a distal lug axis and wherein the first distal travel path comprises a first arcuate distal travel path along the distal lug axis. The second distal travel path comprises a second arcuate distal travel path around said distal lug axis.

Example 7—The surgical instrument of Examples 1, 2, 3, 4 or 6, wherein a portion of the drive member that extends through the articulation joint is flexible.

Example 8—The surgical instrument of Examples 1, 2, 3, 4, 5, 6 or 7, wherein the drive member comprises a proximal drive shaft that includes a distal end that is operably supported in the proximal joint member. A distal drive shaft comprises a proximal end that is operably supported in the distal joint member. A central drive shaft spans between the proximal joint member and the distal joint member distal and comprises a proximal end that is configured to operably interface with the distal end of the proximal drive shaft. The central drive shaft further comprises a distal end that is configured to operably interface with the proximal end of the distal drive shaft.

Example 9—The surgical instrument of Example 8, wherein the proximal drive shaft is configured to apply rotary drive motions to the central drive shaft.

Example 10—The surgical instrument of Examples 1, 2, 3, 4, 5, 6, 7, 8 or 9, wherein the at least two flexible actuator members comprises four cables that span the articulation joint and operably interface with the distal articulation joint member to apply articulation motions thereto.

Example 11—The surgical instrument of Examples 1, 2, 3, 4, 5, 6, 7, 8, 9 or 10, wherein each link is not attached to the proximal joint member and the distal joint member.

Example 12—The surgical instrument of Examples 1, 2, 3, 4, 5, 6, 7, 8, 9, 10 or 11, wherein each link is retained in movable contact with the proximal joint member and the distal joint member.

Example 13—A surgical instrument comprising a shaft assembly that defines a shaft axis and a surgical end effector that defines an end effector axis. The surgical end effector is coupled to the shaft assembly by an articulation joint that is configured to facilitate articulation of the surgical end effector relative to the shaft assembly in an articulation plane between an unarticulated position wherein the end effector axis is axially aligned with the shaft axis in the articulation plane and articulated positions wherein the end effector axis is not axially aligned with the shaft axis. The articulation joint comprises a proximal joint member that is coupled to the shaft assembly and a distal joint member that is coupled to the surgical end effector. The articulation joint further comprises an articulation linkage assembly that comprises a first link that is configured to operably interface with the proximal joint member for movable travel relative thereto in a first proximal travel path and another first proximal travel path that is transverse to the first proximal travel path. The first link is further configured to operably interface with the distal joint member for movable travel relative thereto in a first distal travel path and another first distal travel path that is transverse to the first distal travel path. The articulation linkage assembly further comprises a second link that is configured to operably interface with the proximal joint member for movable travel relative thereto in a second proximal travel path and another second proximal travel path that is transverse to the second proximal travel path. The second link is further configured to operably interface with the distal joint member for movable travel relative thereto in a second distal travel path and another second distal travel path that is transverse to the second distal travel path. The articulation linkage assembly further comprises a third link that is configured to operably interface with the proximal joint member for movable travel relative thereto in a third proximal travel path and another third travel path that is transverse to the third proximal travel path. The third link is further configured to operably interface with the distal joint member for movable travel relative thereto in a third distal travel path and another third distal travel path that is transverse to the third distal travel path. The surgical instrument further comprises at least two flexible actuator members that span the articulation joint and operably interface with the distal joint member to apply articulation motions thereto.

Example 14—The surgical instrument of Example 13, wherein the first link defines a first link axis. The second link defines a second link axis. The third link defines a third link axis. The first link axis, the second link axis, and the third link axis are transverse to each other.

Example 15—The surgical instrument of Examples 13 or 14, wherein the first link, the second link, and the third link are arranged relative to each other to define a central passage that extends between the first link, the second link, and the third link and is configured to operably support a drive member therein.

Example 16—The surgical instrument of Examples 13, 14 or 15, wherein the first link comprises a first proximal saddle that is configured to movably interface with a corresponding first proximal mounting lug on the proximal joint and a first distal saddle that is configured to movably interface with a corresponding first distal mounting lug on the distal joint. The second link comprises a second proximal saddle that is configured to movably interface with a corresponding second proximal mounting lug on the proximal joint and a second distal saddle that is configured to movably interface with a corresponding second distal mounting lug on the distal joint. The third link comprises a third proximal saddle that is configured to movably interface with a corresponding third proximal mounting lug on the proximal joint and a third distal saddle that is configured to movably interface with a corresponding third distal mounting lug on the distal joint.

Example 17—The surgical instrument of Example 16, wherein the first proximal mounting lug defines a first arcuate proximal pivot surface. The first proximal saddle comprises a first U-shaped proximal pivot surface that is configured to movably interface with the first arcuate proximal pivot surface on the first proximal mounting lug to facilitate travel of the first link in the first proximal travel path and another first proximal travel path on the first proximal mounting lug. The second proximal mounting lug defines a second arcuate proximal pivot surface. The second proximal saddle comprises a second U-shaped proximal pivot surface that is configured to movably interface with the second arcuate proximal pivot surface on the second proximal mounting lug to facilitate travel of the second link in the second proximal travel path and another second proximal travel path on the second proximal mounting lug. The third proximal mounting lug defines a third arcuate proximal pivot surface. The third proximal saddle comprises a third U-shaped proximal pivot surface that is configured to movably interface with the third arcuate proximal pivot surface on the third proximal mounting lug to facilitate travel of the third link in the third proximal travel path and another third proximal travel path on the third proximal mounting lug.

Example 18—The surgical instrument of Example 17, wherein the first distal mounting lug defines a first arcuate distal pivot surface. The first distal saddle comprises a first U-shaped distal pivot surface that is configured to movably interface with the first arcuate distal pivot surface on the first distal mounting lug to facilitate travel of the first link in the first distal travel path and another first distal travel path on the first distal mounting lug. The second distal mounting lug defines a second arcuate distal pivot surface. The second distal saddle comprises a second U-shaped distal pivot surface that is configured to movably interface with the second arcuate distal pivot surface on the second distal mounting lug to facilitate travel of the second link in the second distal travel path and another second distal travel path on the second distal mounting lug. The third distal mounting lug defines a third arcuate distal pivot surface. The third distal saddle comprises a third U-shaped distal pivot surface that is configured to movably interface with the third arcuate distal pivot surface on the third distal mounting lug to facilitate travel of the third link in the third distal travel path and another third distal travel path on the third distal mounting lug.

Example 19—The surgical instrument of Example 18, wherein the first proximal mounting lug defines a first proximal lug axis. The first proximal travel path comprises a first arcuate proximal travel path along the first proximal lug axis and the another first proximal travel path comprises another first proximal arcuate travel path that extends around the first proximal lug axis. The second proximal mounting lug defines a second proximal lug axis. The second proximal travel path comprises a second arcuate proximal travel path along the second proximal lug axis and the another second proximal travel path comprises another second proximal arcuate travel path that extends around the second proximal lug axis. The third proximal mounting lug defines a third proximal lug axis. The third proximal travel path comprises a third arcuate proximal travel path that extends along the third proximal lug axis. The another third proximal travel path comprises another third proximal arcuate travel path that extends around the third proximal lug axis. The first distal mounting lug defines a first distal lug axis. The first distal travel path comprises a first arcuate distal travel path that extends along said first distal lug axis. The another first distal travel path comprises another first distal arcuate travel path that extends around the first distal lug axis. The second distal mounting lug defines a second distal lug axis. The second distal travel path comprises a second arcuate distal travel path that extends along the second distal lug axis. The another second distal travel path comprises another second distal arcuate travel path that extends along the second distal lug axis. The third distal mounting lug defines a third distal lug axis. The third distal travel path comprises a third arcuate distal travel path that extends along the third distal lug axis. The another third distal travel path comprises another third distal arcuate travel path that extends around the third distal lug axis.

Example 20—The surgical instrument of Example 19, wherein the first proximal lug axis, the second proximal lug axis, and the third proximal lug axis are transverse to each other and wherein the first distal lug axis, the second distal lug axis, and the third distal lug axis are transverse to each other.

As used in any aspect herein, the term "control circuit" may refer to, for example, hardwired circuitry, programmable circuitry (e.g., a computer processor including one or more individual instruction processing cores, processing unit, processor, microcontroller, microcontroller unit, controller, digital signal processor (DSP), programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein "control circuit" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

While several forms have been illustrated and described, it is not the intention of Applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures or characteristics may be combined in any suitable manner in one or more aspects.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

The surgical instrument systems described herein have been described in connection with the deployment and deformation of staples; however, the embodiments described herein are not so limited. Various embodiments are envisioned which deploy fasteners other than staples, such as clamps or tacks, for example. Moreover, various embodiments are envisioned which utilize any suitable means for sealing tissue. For instance, an end effector in accordance with various embodiments can comprise electrodes configured to heat and seal the tissue. Also, for instance, an end effector in accordance with certain embodiments can apply vibrational energy to seal the tissue.

Many of the surgical instrument systems described herein are motivated by an electric motor; however, the surgical instrument systems described herein can be motivated in any suitable manner. In various instances, the surgical instrument systems described herein can be motivated by a manually-operated trigger, for example. In certain instances, the motors disclosed herein may comprise a portion or portions of a robotically controlled system. Moreover, any of the end effectors and/or tool assemblies disclosed herein can be utilized with a robotic surgical instrument system. U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535, for example, discloses several examples of a robotic surgical instrument system in greater detail.

The entire disclosures of:
U.S. Pat. No. 5,403,312, entitled ELECTROSURGICAL HEMOSTATIC DEVICE, which issued on Apr. 4, 1995;
U.S. Pat. No. 7,000,818, entitled SURGICAL STAPLING INSTRUMENT HAVING SEPARATE DISTINCT CLOSING AND FIRING SYSTEMS, which issued on Feb. 21, 2006;
U.S. Pat. No. 7,422,139, entitled MOTOR-DRIVEN SURGICAL CUTTING AND FASTENING INSTRUMENT WITH TACTILE POSITION FEEDBACK, which issued on Sep. 9, 2008;
U.S. Pat. No. 7,464,849, entitled ELECTRO-MECHANICAL SURGICAL INSTRUMENT WITH CLOSURE SYSTEM AND ANVIL ALIGNMENT COMPONENTS, which issued on Dec. 16, 2008;
U.S. Pat. No. 7,670,334, entitled SURGICAL INSTRUMENT HAVING AN ARTICULATING END EFFECTOR, which issued on Mar. 2, 2010;
U.S. Pat. No. 7,753,245, entitled SURGICAL STAPLING INSTRUMENTS, which issued on Jul. 13, 2010;
U.S. Pat. No. 8,393,514, entitled SELECTIVELY ORIENTABLE IMPLANTABLE FASTENER CARTRIDGE, which issued on Mar. 12, 2013;
U.S. patent application Ser. No. 11/343,803, entitled SURGICAL INSTRUMENT HAVING RECORDING CAPABILITIES, now U.S. Pat. No. 7,845,537;
U.S. patent application Ser. No. 12/031,573, entitled SURGICAL CUTTING AND FASTENING INSTRUMENT HAVING RF ELECTRODES, filed Feb. 14, 2008;
U.S. patent application Ser. No. 12/031,873, entitled END EFFECTORS FOR A SURGICAL CUTTING AND STAPLING INSTRUMENT, filed Feb. 15, 2008, now U.S. Pat. No. 7,980,443;
U.S. patent application Ser. No. 12/235,782, entitled MOTOR-DRIVEN SURGICAL CUTTING INSTRUMENT, now U.S. Pat. No. 8,210,411;
U.S. patent application Ser. No. 12/235,972, entitled MOTORIZED SURGICAL INSTRUMENT, now U.S. Pat. No. 9,050,083;
U.S. patent application Ser. No. 12/249,117, entitled POWERED SURGICAL CUTTING AND STAPLING APPARATUS WITH MANUALLY RETRACTABLE FIRING SYSTEM, now U.S. Pat. No. 8,608,045;
U.S. patent application Ser. No. 12/647,100, entitled MOTOR-DRIVEN SURGICAL CUTTING INSTRUMENT WITH ELECTRIC ACTUATOR DIRECTIONAL CONTROL ASSEMBLY, filed Dec. 24, 2009, now U.S. Pat. No. 8,220,688;
U.S. patent application Ser. No. 12/893,461, entitled STAPLE CARTRIDGE, filed Sep. 29, 2012, now U.S. Pat. No. 8,733,613;
U.S. patent application Ser. No. 13/036,647, entitled SURGICAL STAPLING INSTRUMENT, filed Feb. 28, 2011, now U.S. Pat. No. 8,561,870;
U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535;
U.S. patent application Ser. No. 13/524,049, entitled ARTICULATABLE SURGICAL INSTRUMENT COMPRISING A FIRING DRIVE, filed on Jun. 15, 2012, now U.S. Pat. No. 9,101,358;

U.S. patent application Ser. No. 13/800,025, entitled STAPLE CARTRIDGE TISSUE THICKNESS SENSOR SYSTEM, filed on Mar. 13, 2013, now U.S. Pat. No. 9,345,481;

U.S. patent application Ser. No. 13/800,067, entitled STAPLE CARTRIDGE TISSUE THICKNESS SENSOR SYSTEM, filed on Mar. 13, 2013, now U.S. Patent Application Publication No. 2014/0263552, now abandoned;

U. S. Patent Application Publication No. 2007/0175955, entitled SURGICAL CUTTING AND FASTENING INSTRUMENT WITH CLOSURE TRIGGER LOCKING MECHANISM, filed Jan. 31, 2006, now abandoned; and U. S. Patent Application Publication No. 2010/0264194, entitled SURGICAL STAPLING INSTRUMENT WITH AN ARTICULATABLE END EFFECTOR, filed Apr. 22, 2010, now U.S. Pat. No. 8,308,040, are hereby incorporated by reference herein.

Although various devices have been described herein in connection with certain embodiments, modifications and variations to those embodiments may be implemented. Particular features, structures, or characteristics may be combined in any suitable manner in one or more embodiments. Thus, the particular features, structures, or characteristics illustrated or described in connection with one embodiment may be combined in whole or in part, with the features, structures or characteristics of one or more other embodiments without limitation. Also, where materials are disclosed for certain components, other materials may be used. Furthermore, according to various embodiments, a single component may be replaced by multiple components, and multiple components may be replaced by a single component, to perform a given function or functions. The foregoing description and following claims are intended to cover all such modification and variations.

The devices disclosed herein can be designed to be disposed of after a single use, or they can be designed to be used multiple times. In either case, however, a device can be reconditioned for reuse after at least one use. Reconditioning can include any combination of the steps including, but not limited to, the disassembly of the device, followed by cleaning or replacement of particular pieces of the device, and subsequent reassembly of the device. In particular, a reconditioning facility and/or surgical team can disassemble a device and, after cleaning and/or replacing particular parts of the device, the device can be reassembled for subsequent use. Those skilled in the art will appreciate that reconditioning of a device can utilize a variety of techniques for disassembly, cleaning/replacement, and reassembly. Use of such techniques, and the resulting reconditioned device, are all within the scope of the present application.

The devices disclosed herein may be processed before surgery. First, a new or used instrument may be obtained and, when necessary, cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, and/or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta radiation, gamma radiation, ethylene oxide, plasma peroxide, and/or steam.

While this invention has been described as having exemplary designs, the present invention may be further modified within the spirit and scope of the disclosure. This application is therefore intended to cover any variations, uses, or adaptations of the invention using its general principles.

What is claimed is:

1. A surgical instrument, comprising:
   (a) a shaft defining a shaft axis;
   (b) an end effector operatively coupled with the shaft, wherein the end effector defines an end effector axis and is configured to clamp and staple tissue with a plurality of staples; and
   (c) an articulation joint that interconnects the end effector with the shaft and is configured to facilitate articulation of the end effector relative to the shaft in an articulation plane between an unarticulated position in which the end effector axis is axially aligned with the shaft axis in the articulation plane and articulated positions in which the end effector axis is not axially aligned with the shaft axis, wherein the articulation joint comprises:
      (1) a proximal joint portion coupled to the shaft;
      (2) a distal joint portion coupled to the end effector; and
      (3) a plurality of links,
   wherein each link is configured to contact and move relative to the proximal joint portion along a first proximal travel path and a second proximal travel path non-parallel to the first proximal travel path,
   wherein each link is configured to contact and move relative to the distal joint portion along a first distal travel path and a second distal travel path non-parallel to the first distal travel path.

2. The surgical instrument of claim 1, wherein the plurality of links comprises at least three links.

3. The surgical instrument of claim 2, wherein the plurality of links comprises:
   a first link configured to operably interface with the proximal joint portion for movable travel relative thereto in a pair of first proximal travel paths that are transverse to one another, and wherein the first link is configured to operably interface with the distal joint portion for movable travel relative thereto in a pair of first distal travel paths that are transverse to one another;
   a second link configured to operably interface with the proximal joint portion for movable travel relative thereto in a pair of second proximal travel paths that are non-parallel to one another, and wherein the second link is configured to operably interface with the distal joint portion for movable travel relative thereto in a pair of second distal travel paths that are non-parallel to one another; and
   a third link configured to operably interface with the proximal joint portion for movable travel relative thereto in a pair of third proximal travel paths that are non-parallel to one another, and wherein the third link is configured to operably interface with the distal joint portion for movable travel relative thereto in a pair of third distal travel paths that are non-parallel to one another.

4. The surgical instrument of claim 1, wherein each link comprises:
   a proximal saddle configured to movably interface with a corresponding proximal mounting lug on the proximal joint portion; and a distal saddle configured to movably interface with a corresponding distal mounting lug on the distal joint portion.

5. The surgical instrument of claim 4, wherein the links define a central passage therebetween, wherein each proximal mounting lug defines an arcuate proximal pivot surface, wherein each proximal saddle comprises a U-shaped proximal pivot surface configured to movably interface with the arcuate proximal pivot surface on the proximal mounting lug to facilitate travel of the link in the first proximal travel path and the second proximal travel path on the proximal mounting lug, wherein each distal mounting lug defines an arcuate distal pivot surface, wherein each distal saddle comprises a U-shaped distal pivot surface configured to movably interface with the arcuate distal pivot surface on the distal mounting lug to facilitate travel of the link in the first distal travel path and the second distal travel path on the distal mounting lug.

6. The surgical instrument of claim 5, wherein each proximal mounting lug defines a proximal lug axis, wherein the first proximal travel path comprises a first arcuate proximal travel path along the proximal lug axis, wherein the second proximal travel path comprises a second arcuate proximal travel path around the proximal lug axis, wherein each distal mounting lug defines a distal lug axis, wherein the first distal travel path comprises a first arcuate distal travel path along the distal lug axis, and wherein the second distal travel path comprises a second arcuate distal travel path around the distal lug axis.

7. The surgical instrument of claim 1, wherein the surgical instrument further comprises a driver extending through the proximal joint portion, wherein a portion of the driver is flexible.

8. The surgical instrument of claim 1, wherein the surgical instrument further comprises a driver extending through the proximal joint portion and the distal joint portion to operably interface with the end effector, wherein the driver comprises:
a proximal drive shaft comprising a distal end operably supported in the proximal joint portion;
a distal drive shaft comprising a proximal end operably supported in the distal joint portion; and
a central drive shaft spanning between the proximal joint portion and the distal joint portion, wherein the central drive shaft comprises a proximal end configured to operably interface with the distal end of the proximal drive shaft, and wherein the central drive shaft further comprises a distal end configured to operably interface with the proximal end of the distal drive shaft.

9. The surgical instrument of claim 8, wherein the proximal drive shaft is configured to apply rotary drive motions to the central drive shaft.

10. The surgical instrument of claim 1, further comprising four cables spanning the articulation joint and operably interfacing with the distal joint portion to apply articulation motions thereto.

11. The surgical instrument of claim 1, wherein each link of the plurality of links is unattached to each of the proximal joint portion and the distal joint portion.

12. The surgical instrument of claim 11, wherein each the link of the plurality of links is retained in movable contact with the proximal joint portion and the distal joint portion.

13. A surgical instrument, comprising:
(a) a shaft defining a shaft axis;
(b) an end effector operatively coupled with the shaft, wherein the end effector defines an end effector axis and is configured to clamp tissue; and
(c) an articulation joint that interconnects the end effector with the shaft and is configured to facilitate articulation of the end effector relative to the shaft in an articulation plane between an unarticulated position in which the end effector axis is axially aligned with the shaft axis in the articulation plane and articulated positions in which the end effector axis is not axially aligned with the shaft axis, wherein the articulation joint comprises:
(1) a proximal joint portion coupled to the shaft;
(2) a distal joint portion coupled to the end effector; and
(3) an articulation linkage assembly comprising:
(A) a first link configured to operably interface with contact and move relative to the proximal joint portion for movable along a first proximal travel path, wherein the first link is configured to contact and move relative to the distal joint portion along a first distal travel path;
(B) a second link configured to contact and move relative to the proximal joint portion along a second proximal travel path, wherein the second link is configured to contact and move relative to the distal joint portion for along a second distal travel path; and
(C) a third link configured to contact and move relative to the proximal joint portion along a third proximal travel path, wherein the third link is configured to operably contact and move relative to the distal joint portion along a third distal travel path.

14. The surgical instrument of claim 13, wherein the first link defines a first link axis, wherein the second link defines a second link axis, wherein the third link defines a third link axis, and wherein each of the first link axis, the second link axis, and the third link axis is non-parallel to the others of the first link axis, the second link axis, and the third link axis.

15. The surgical instrument of claim 14, wherein the first link, the second link, and the third link are arranged relative to each other to define a central passage that extends between the first link, the second link, and the third link, wherein the central passage is configured to operably support a driver therein.

16. The surgical instrument of claim 13, wherein the first link comprises:
a first proximal saddle configured to movably interface with a corresponding first proximal mounting lug on the proximal joint portion; and
a first distal saddle configured to movably interface with a corresponding first distal mounting lug on the distal joint portion, wherein the second link comprises:
a second proximal saddle configured to movably interface with a corresponding second proximal mounting lug on the proximal joint portion; and
a second distal saddle configured to movably interface with a corresponding second distal mounting lug on the distal joint portion, and wherein the third link comprises:
a third proximal saddle configured to movably interface with a corresponding third proximal mounting lug on the proximal joint portion; and
a third distal saddle configured to movably interface with a corresponding third distal mounting lug on the distal joint portion.

17. The surgical instrument of claim 16, wherein the first proximal mounting lug defines a first arcuate proximal pivot surface, wherein the first proximal saddle comprises a first U-shaped proximal pivot surface configured to movably interface with the first arcuate proximal pivot surface on the first proximal mounting lug to facilitate travel of the first link in the first proximal travel path on the first proximal mounting lug, wherein the second proximal mounting lug defines a second arcuate proximal pivot surface, wherein the second proximal saddle comprises a second U-shaped proximal pivot surface configured to movably interface with the second arcuate proximal pivot surface on the second proximal mounting lug to facilitate travel of the second link in the second proximal travel path on the second proximal mounting lug, and wherein the third proximal mounting lug defines a third arcuate proximal pivot surface, wherein the third proximal saddle comprises a third U-shaped proximal pivot surface configured to movably interface with the third arcuate proximal pivot surface on the third proximal mounting lug to facilitate travel of the third link in the third proximal travel path on the third proximal mounting lug.

18. The surgical instrument of claim 17, wherein the first distal mounting lug defines a first arcuate distal pivot surface, wherein the first distal saddle comprises a first U-shaped distal pivot surface configured to movably interface with the first arcuate distal pivot surface on the first distal mounting lug to facilitate travel of the first link in the first distal travel path on the first distal mounting lug, wherein the second distal mounting lug defines a second arcuate distal pivot surface, wherein the second distal saddle comprises a second U-shaped distal pivot surface configured to movably interface with the second arcuate distal pivot surface on the second distal mounting lug to facilitate travel of the second link in the second distal travel path on the second distal mounting lug, and wherein the third distal mounting lug defines a third arcuate distal pivot surface, wherein the third distal saddle comprises a third U-shaped distal pivot surface configured to movably interface with the third arcuate distal pivot surface on the third distal mounting lug to facilitate travel of the third link in the third distal travel path on the third distal mounting lug.

19. The surgical instrument of claim 18, wherein the first proximal mounting lug defines a first proximal lug axis, wherein the first proximal travel path comprises a first arcuate proximal travel path along the first proximal lug axis, wherein the second proximal mounting lug defines a second proximal lug axis, wherein the second proximal travel path comprises a second arcuate proximal travel path along the second proximal lug axis, wherein the third proximal mounting lug defines a third proximal lug axis, wherein the third proximal travel path comprises a third arcuate proximal travel path along the third proximal lug axis, wherein the first distal mounting lug defines a first distal lug axis, wherein the first distal travel path comprises a first arcuate distal travel path along the first distal lug axis, wherein the second distal mounting lug defines a second distal lug axis, wherein the second distal travel path comprises a second arcuate distal travel path along the second distal lug axis, wherein the third distal mounting lug defines a third distal lug axis, wherein the third distal travel path comprises a third arcuate distal travel path along the third distal lug axis.

20. A surgical instrument, comprising:
(a) a shaft defining a shaft axis;
(b) an end effector operatively coupled with the shaft, wherein the end effector defines an end effector axis and is configured to clamp tissue;
(c) an articulation joint that interconnects the end effector with the shaft and is configured to facilitate articulation of the end effector relative to the shaft in an articulation plane between an unarticulated position in which the end effector axis is axially aligned with the shaft axis in the articulation plane and articulated positions in which the end effector axis is not axially aligned with the shaft axis, wherein the articulation joint comprises:
(1) a proximal joint portion coupled to the shaft;
(2) a distal joint portion coupled to the end effector; and
(3) an articulation linkage assembly comprising:
 (A) a first link configured to operably interface with and move relative to each of the proximal joint portion and the distal joint portion;
 (B) a second link configured to operably interface with and move relative to each of the proximal joint portion and the distal joint portion; and
 (C) a third link configured to operably interface with and move relative to each of the proximal joint portion and the distal joint portion; and
(d) a rotary driver extending through the articulation joint and configured to actuate the end effector.

* * * * *